United States Patent
Yokota et al.

(10) Patent No.: US 11,034,955 B2
(45) Date of Patent: *Jun. 15, 2021

(54) CHIMERIC DOUBLE-STRANDED NUCLEIC ACID

(71) Applicants: National University Corporation Tokyo Medical and Dental University, Tokyo (JP); Osaka University, Osaka (JP)

(72) Inventors: Takanori Yokota, Tokyo (JP); Kazutaka Nishina, Tokyo (JP); Satoshi Obika, Osaka (JP); Hidehiro Mizusawa, Tokyo (JP)

(73) Assignees: National University Corporation Tokyo Medical and Dental University, Tokyo (JP); Osaka University, Osaka (JP)

( * ) Notice: Subject to any disclaimer, the term of this patent is extended or adjusted under 35 U.S.C. 154(b) by 53 days.

This patent is subject to a terminal disclaimer.

(21) Appl. No.: 16/410,803

(22) Filed: May 13, 2019

(65) Prior Publication Data

US 2019/0270996 A1 Sep. 5, 2019

Related U.S. Application Data

(60) Continuation of application No. 15/725,845, filed on Oct. 5, 2017, now Pat. No. 10,337,006, which is a division of application No. 14/303,989, filed on Jun. 13, 2014, now Pat. No. 9,816,089, which is a continuation-in-part of application No. PCT/JP2012/083180, filed on Dec. 17, 2012.

(30) Foreign Application Priority Data

Dec. 16, 2011 (JP) .............................. JP2011-275488

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 2310/11* (2013.01); *C12N 2310/15* (2013.01); *C12N 2310/3181* (2013.01); *C12N 2310/3231* (2013.01); *C12N 2310/341* (2013.01); *C12N 2310/3513* (2013.01); *C12N 2310/3515* (2013.01); *C12N 2310/53* (2013.01); *C12N 2320/52* (2013.01)

(58) Field of Classification Search
CPC ..... C12N 15/11; C12N 15/111; C12N 15/115; C12N 2310/11; C12N 2310/3515
USPC .... 435/6.1, 91.1, 91.31, 455, 458; 536/23.1, 536/24.5

See application file for complete search history.

(56) References Cited

U.S. PATENT DOCUMENTS

| | | | |
|---|---|---|---|
| 10,337,006 B2 * | 7/2019 | Yokota | A61P 43/00 |
| 2002/0068708 A1 | 6/2002 | Wengel et al. | |
| 2003/0104401 A1 | 6/2003 | Lin | |
| 2005/0215497 A1 | 9/2005 | Harel-Bellan et al. | |
| 2006/0281696 A1 | 12/2006 | Hecker et al. | |
| 2007/0161587 A1 | 7/2007 | Collins et al. | |
| 2007/0167387 A1 | 7/2007 | Imanishi et al. | |
| 2008/0199960 A1 | 8/2008 | Juliano et al. | |
| 2009/0005332 A1 | 1/2009 | Hauser et al. | |
| 2009/0082300 A1 | 3/2009 | Brown-Driver et al. | |
| 2009/0306005 A1 | 12/2009 | Bhanot et al. | |
| 2009/0326043 A1 | 12/2009 | Moelling | |
| 2010/0041047 A1 | 2/2010 | Vickers et al. | |
| 2010/0151458 A1 | 6/2010 | Crooke | |
| 2010/0216864 A1 | 8/2010 | Straarup et al. | |
| 2011/0135647 A1 | 6/2011 | Nakamura et al. | |
| 2012/0283312 A1 | 11/2012 | Dobie et al. | |
| 2013/0079382 A1 | 3/2013 | Smith | |

(Continued)

FOREIGN PATENT DOCUMENTS

| | | |
|---|---|---|
| DE | 10240417 A1 | 3/2004 |
| EP | 2133425 A1 | 12/2009 |
| JP | 09-110894 A | 4/1997 |

(Continued)

OTHER PUBLICATIONS

Abe et al., "Specific inhibition of influenza virus RNA polymerase and nucleoprotein gene expression by circular dumbbell RNA/DNA chimeric oligonucleotides containing antisense phosphodiester oligonucleotides," FEBS Letters, 1998, 425:91-96.

(Continued)

*Primary Examiner* — Jane J Zara
(74) *Attorney, Agent, or Firm* — Foley & Lardner LLP

(57) ABSTRACT

A method of reducing the level of a transcription product in a cell comprising contacting with the cell a composition comprising a double-stranded nucleic acid complex comprising a first nucleic acid strand annealed to a second nucleic acid strand, wherein: (i) the first nucleic acid strand hybridizes to the transcription product and comprises (a) a region consisting of at least 4 consecutive nucleotides that are recognized by RNase H when the strand is hybridized to the transcription product, (b) one or more nucleotide analogs located on 5' terminal side of the region, (c) one or more nucleotide analogs located on 3' terminal side of the region and (d) a total number of nucleotides and nucleotide analogs ranging from 8 to 35 nucleotides and (ii) the second nucleic acid strand comprises (a) nucleotides and optionally nucleotide analogs and (b) at least 4 consecutive RNA nucleotides.

14 Claims, 41 Drawing Sheets

Specification includes a Sequence Listing.

(56) References Cited

U.S. PATENT DOCUMENTS

2015/0167005 A1 6/2015 Freier et al.
2018/3200181 11/2018 Yokota et al.

FOREIGN PATENT DOCUMENTS

| JP | 10-195098 A | 7/1998 |
|---|---|---|
| JP | 10-304889 A | 11/1998 |
| JP | 2002-521310 A | 7/2002 |
| JP | 2006-522586 A | 10/2006 |
| JP | 2010-500003 A | 1/2010 |
| WO | WO 03/042385 A2 | 5/2003 |
| WO | WO 2004/044181 A2 | 5/2004 |
| WO | WO 2005/021570 A1 | 3/2005 |
| WO | WO 2005/113571 A2 | 12/2005 |
| WO | WO 2006/074108 A2 | 7/2006 |
| WO | WO 2007/143315 A2 | 12/2007 |
| WO | WO 2008/029619 A1 | 3/2008 |
| WO | WO 2008/043753 A2 | 4/2008 |
| WO | WO 2008/111908 A1 | 9/2008 |

OTHER PUBLICATIONS

Bennett et al., "RNA Targeting Therapeutics: Molecular Mechanisms of Antisense Oligonucleotides as a Therapeutic Platform," Annu. Rev. Pharmacol. Toxicol., Feb. 1, 2010, 50(1):259-293.
Bramsen et al., "Improved silencing properties using small internally segmented interfering RNAs," Nucleic Acids Research, Jan. 1, 2007, 35(17):5886-5897.
European Office Action dated Sep. 28, 2015, in EP 12815856.5.
Far et al., "The activity of siRNA in mammalian cells is related to structural target accessibility: a comparison with antisense oligonucleotides," Nucleic Acids Research, Aug. 1, 2003, 31(15):4417-4424.
Freier et al., "The ups and downs of nucleic acid duplex stability: structure-stability studies on chemically-modified DNA:RNA duplexes," Nucleic Acids Research, Jan. 1, 1997, 25(22):4429-4443.
Gen Bank, NCBI Reference Sequence NM_018963.4, "*Homo sapiens* bromodomain and WD repeat domain containing 1 (BRWD1) transcript variant 1, mRNA," Nov. 23, 2000, last revised Dec. 29, 2017, 15 pages.
Jekerle et al., "Functional comparison of single- and double-stranded *mdr1* antisense oligodeoxynucleotides in human ovarian cancer cell lines," J. Pharm. Pharmaceut. Sci., Jan. 1, 2005, 8(3):516-527.
Jepsen et al., "LNA-Antisense rivals siRNA for gene silencing," Current Opinion in Drug Discovery & Development, 2004, 7(2):188-194.
Karkare et al., "Promising nucleic acid analogs and mimics: characteristic features and applications of PNA, LNA, and morpholino," Appl. Microbiol. Biotechnol., May 9, 2006, 71(5):575-586.
Lamberton et al., "Varying the Nucleic Acid Composition of siRNA Molecules Dramatically Varies the Duration and Degree of Gene Silencing," Molecular Biotechnology, Jun. 1, 2003, 24(2):111-119.
Nishina et al. "Efficient In Vivo Delivery of siRNA to the Liver by Conjugation of α-Tocopherol," Feb. 12, 2008, 16(4):734-740.
Office Action dated Mar. 6, 2018, in JP 2017-044034.
Office Action dated Nov. 1, 2016, in JP 2014-528740.
Peer et al., Systemic Leukocyte-Directed siRNA Delivery Revealing Cyclin D1 as an Anti-Inflammatory Target, 2008, 319:627-630.
Soutschek et al., "Therapeutic silencing of an endogenous gene by systemic administration of modified siRNAs," Nature, Nov. 11, 2004, 432:173-178.
Yamakawa et al., "Properties of Nicked and Circular Dumbbell RNA/DNA Chimeric Oligonucleotides Containing Antisense Phosphodiester Oligodeoxynucleotides," Bioorganic & Medicinal Chemistry, Jul. 1, 1998, 6(7):1025-1032.
Zhou et al., "Fine Tuning of Electrostatics around the Internucleotidic Phosphate through Incorporation of Modified 2',4'-Carbocyclic-LNAs and -ENAs Leads to Signification Modulation of Antisense Properties," J. Org. Chem., Jan. 2009, 74(1,2):118-134.

\* cited by examiner

FIG. 7A
FIG. 7B
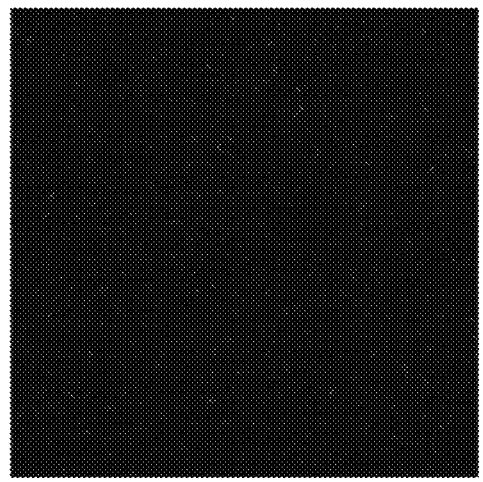
Cy3-ASO
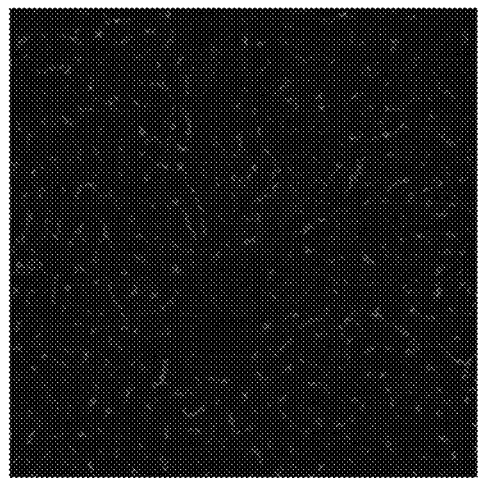
Cy3-Chol-ASO

Lane M: marker
Lane 1: ss-ASO
Lane 2: ds-ASO/cRNA(o)
Lane 3: ds-ASO/cRNA(G)
Lane 4: ds-ASO/cRNA(m/s)

CHIMERIC DOUBLE-STRANDED NUCLEIC ACID

CROSS REFERENCE

This is a Continuation of U.S. application Ser. No. 15/725,845, filed Oct. 5, 2017, which is a Divisional of U.S. application Ser. No. 14/303,989, filed Jun. 13, 2014, which is a Continuation-in-part of International Application No. PCT/JP2012/083180 filed on Dec. 17, 2012, designating the U.S. and claims the benefit of Japanese Patent Application No. JP2011-275488 filed on Dec. 16, 2011. The entire disclosures of the prior applications are hereby incorporated by reference herein in their entirety.

The instant application contains a Sequence Listing which has been submitted in ASCII format via EFS-WEB and is hereby incorporated by reference in its entirety. The ASCII copy, created on May 13, 2019, is named sequence.txt and is 15,124 bytes.

BACKGROUND OF THE INVENTION

Field of the Invention

The present application relates to a double-stranded nucleic acid having an activity of suppressing the expression of a target gene by means of an antisense effect, and more particularly, to a double-stranded nucleic acid including an antisense nucleic acid that is complementary to the transcription product of a target gene and contains a region comprising four or more contiguous bases, and a nucleic acid that is complementary to the foregoing nucleic acid.

Related Background Art

In recent years, oligonucleotides have been a subject of interest in the on-going development of pharmaceutical products called nucleic acid drugs, and particularly, from the viewpoints of high selectivity of target gene and low toxicity, the development of nucleic acid drugs utilizing an antisense method is actively underway. The antisense method is a method of selectively inhibiting the expression of a protein that is encoded by a target gene, by introducing into a cell an oligonucleotide (antisense oligonucleotide (ASO)) which is complementary to a partial sequence of the mRNA (sense strand) of a target gene.

As illustrated in FIG. 1 (upper portion), when an oligonucleotide comprising an RNA is introduced into a cell as an ASO, the ASO binds to a transcription product (mRNA) of the target gene, and a partial double strand is formed. It is known that this double strand plays a role as a cover to prevent translation by a ribosome, and thus the expression of the protein encoded by the target gene is inhibited.

On the other hand, when an oligonucleotide comprising a DNA is introduced into a cell as an ASO, a partial DNA-RNA hetero-duplex is formed. Since this structure is recognized by RNase H, and the mRNA of the target gene is thereby decomposed, the expression of the protein encoded by the target gene is inhibited. (FIG. 1, lower portion). Furthermore, it has been also found that in many cases, the gene expression suppressing effect is higher in the case of using a DNA as an ASO (RNase H-dependent route), as compared with the case of using an RNA.

On the occasion of utilizing an oligonucleotide as a nucleic acid drug, various nucleic acid analogs such as Locked Nucleic Acid (LNA) (registered trademark), other bridged nucleic acids, and the like have been developed in consideration of an enhancement of the binding affinity to a target RNA, stability in vivo, and the like.

As illustrated in FIG. 2, since the sugar moiety of a natural nucleic acid (RNA or DNA) has a five-membered ring with four carbon atoms and one oxygen atom, the sugar moiety has two kinds of conformations, an N-form and an S-form. It is known that these conformations swing from one to the other, and thereby, the helical structure of the nucleic acid also adopts different forms, an A-form and a B-form. Since the mRNA that serves as the target of the aforementioned ASO adopts a helical structure in the A-form, with the sugar moiety being mainly in the N-form, it is important for the sugar moiety of the ASO to adopt the N-form from the viewpoint of increasing the affinity to RNA. A product that has been developed under this concept is a modified nucleic acid such as a LNA (2'-O,4'-C-methylene-bridged nucleic acid (2',4'-BNA)). For example, in the LNA, as the oxygen at the 2'-position and the carbon at the 4'-position are bridged by a methylene group, the conformation is fixed to the N-form, and there is no more fluctuation between the conformations. Therefore, an oligonucleotide synthesized by incorporating several units of LNA has very high affinity to RNA and very high sequence specificity, and also exhibits excellent heat resistance and nuclease resistance, as compared with oligonucleotides synthesized with conventional natural nucleic acids (see JP 10-304889 A). Since other artificial nucleic acids also have such characteristics, much attention has been paid to artificial nucleic acids in connection with the utilization of an antisense method and the like (see JP 10-304889 A, WO 2005/021570, JP 10-195098 A, JP 2002-521310 W, WO 2007/143315, WO 2008/043753 and WO 2008/029619).

Furthermore, when n oligonucleotide is applied to a drug, it is important that the relevant oligonucleotide can be delivered to the target site with high specificity and high efficiency. In addition, as methods for delivering an oligonucleotide, a method of utilizing lipids such as cholesterol and vitamin E (Kazutaka Nishina et al., Molecular Therapy, Vol. 16, 734-740 (2008) and Jurgen Soutscheck et al., Nature, Vol. 432, 173-178 (2004)), a method of utilizing a receptor-specific peptide such as RVG-9R (Kazutaka Nishina et al., Molecular Therapy, Vol. 16, 734-740 (2008)), and a method of utilizing an antibody specific to the target site (Dan Peer et al., Science, Vol. 319, 627-630 (2008)) have been developed.

SUMMARY OF THE INVENTION

In certain embodiments, a double-stranded nucleic acid complex comprises an antisense nucleic acid which suppresses the expression of a target gene, or more generally, suppresses the level of an RNA transcription product. It is a further object that the double-stranded nucleic acid complex delivers the antisense nucleic acid strand to a target site with high specificity and high efficiency.

For the purpose of studying how to enhance the stability of an ASO, the activity of suppressing the expression of a target gene in vivo (antisense effect), and the specificity and efficiency in the delivery of an ASO to a target site (delivery properties) in an antisense method, the inventors prepared an ASO comprising a LNA and a DNA (LNA/DNA gapmer), to which a lipid (cholesterol) was directly bound, and the inventors evaluated the delivery properties and the antisense effect by intravenously administering this ASO to a mouse. As a result, it was found that when cholesterol is bound to the ASO, the delivery properties of the ASO to the liver are enhanced, however, the antisense effect was lost.

Thus, the inventors conducted thorough investigations in order to develop a nucleic acid which has a high antisense effect while increasing the delivery properties of an ASO, and as a result, the inventors conceived of a new double-stranded nucleic acid complex produced, in one embodiment, by annealing a LNA/DNA gapmer to an RNA strand complementary to the gapmer, and first evaluated the antisense effect. As a result, it was found that the antisense effect of the double-stranded nucleic acid is typically better than that of a single-stranded LNA/DNA gapmer, and is rather enhanced depending on the strand length of the ASO used. The inventors also produced a double-stranded nucleic acid in which tocopherol is bound to the complementary strand comprising RNA, intravenously administered the double-stranded nucleic acid to a mouse, and evaluated its antisense effect. As a result, it was found that the double-stranded nucleic acid containing the complementary strand bound to tocopherol has a very high antisense effect. In addition, the inventors also found that the antisense effect of a LNA/DNA gapmer produced by annealing with a complementary strand comprising PNA (peptide nucleic acid) instead of RNA is at least similar to or better than that of a single-stranded LNA/DNA gapmer, and furthermore the PNA provides a way to indirectly associate the ASO with a peptide, protein, or antibody that can direct delivery of the ASO to a particular site.

That is, the application relates to a double-stranded nucleic acid having an activity of suppressing the expression of a target gene by means of an antisense effect.

In certain embodiments, the following are provided.

1. A method of reducing the level of a transcription product in a cell comprising contacting with the cell a composition comprising:
a double-stranded nucleic acid complex comprising a first nucleic acid strand annealed to a second nucleic acid strand, wherein:
(i) the first nucleic acid strand hybridizes to the transcription product and comprises (a) a region consisting of at least 4 consecutive nucleotides that are recognized by RNase H when the strand is hybridized to the transcription product, (b) one or more nucleotide analogs located on 5' terminal side of the region, (c) one or more nucleotide analogs located on 3' terminal side of the region and (d) a total number of nucleotides and nucleotide analogs ranging from 8 to 35 nucleotides and
(ii) the second nucleic acid strand comprises (a) nucleotides and optionally nucleotide analogs and (b) at least 4 consecutive RNA nucleotides.

2. The method according to the item 1, wherein the total number of nucleotides and nucleotide analogs in the first nucleic acid strand and the total number of nucleotides and nucleotide analogs in the second nucleic acid strand are the same.

3. The method according to the item 1, wherein the total number of nucleotides and nucleotide analogs in the first nucleic acid strand and the total number of nucleotides and nucleotide analogs in the second nucleic acid strand are different.

4. The method according to any one of the items 1 to 3, wherein the nucleotide analogs in the first nucleic acid strand are bridged nucleotides.

5. The method according to any one of the items 1 to 4, wherein at least one of the nucleotides and the nucleotide analogs in the first nucleic acid strand is phosphorothioated.

6. The method according to any one of the items 1 to 5, wherein the second nucleic acid strand comprises one or more phosphorothioated nucleotides located 5' and/or 3' to the at least 4 consecutive RNA nucleotides.

7. The method according to any one of the items 1 to 6, wherein the second nucleic acid strand further comprises a functional moiety having a function selected from a labeling function, a purification function, and a targeted delivery function.

8. The method according to any one of the items 3 to 7, wherein the double stranded nucleic acid complex further comprises a third nucleic acid strand annealed to the second nucleic acid.

9. The method according to any one of the items 3 to 8, wherein the third nucleic strand hybridizes to the transcription product and comprises (a) a region consisting of at least 4 consecutive nucleotides that are recognized by RNase H when the strand is hybridized to a second transcription product, (b) one or more nucleotide analogs located on 5' terminal side of the region, (c) one or more nucleotide analogs located on 3' terminal side of the region and (d) a total number of nucleotides and nucleotide analogs ranging from 8 to 35 nucleotides.

10. The method according to any one of the items 3 to 8, wherein the third nucleic strand hybridizes to another transcription product and comprises (a) a region consisting of at least 4 consecutive nucleotides that are recognized by RNase H when the strand is hybridized to the another transcription product, (b) one or more nucleotide analogs located on 5' terminal side of the region, (c) one or more nucleotide analogs located on 3' terminal side of the region and (d) a total number of nucleotides and nucleotide analogs ranging from 8 to 35 nucleotides.

11. The method according to any one of the items 8 to 10, wherein the third nucleic acid strand further comprises a functional moiety having a function selected from a labeling function, a purification function, and a targeted delivery function.

12. A composition comprising a double-stranded nucleic acid complex comprising a first nucleic acid strand annealed to a second nucleic acid strand, wherein:
(i) the first nucleic acid strand hybridizes to the transcription product and comprises (a) a region consisting of at least 4 consecutive nucleotides that are recognized by RNase H when the strand is hybridized to the transcription product, (b) one or more nucleotide analogs located on 5' terminal side of the region, (c) one or more nucleotide analogs located on 3' terminal side of the region and (d) a total number of nucleotides and nucleotide analogs ranging from 8 to 35 nucleotides and
(ii) the second nucleic acid strand comprises (a) nucleotides and optionally nucleotide analogs and (b) at least 4 consecutive RNA nucleotides.

13. The composition according to the item 12, wherein the total number of nucleotides and nucleotide analogs in the first nucleic acid strand and the total number of nucleotides and nucleotide analogs in the second nucleic acid strand are the same.

14. The composition according to item 12, wherein the total number of nucleotides and nucleotide analogs in the first nucleic acid strand and the total number of nucleotides and nucleotide analogs in the second nucleic acid strand are different.

15. The composition according to any one of the items 12 to 14, wherein the nucleotide analogs in the first nucleic acid strand are bridged nucleotides.

16. The composition according to any one of the items 12 to 15, wherein at least one of the nucleotides and the nucleotide analogs in the first nucleic acid strand is phosphorothioated.

17. The composition of according to any one of the items 12 to 16, wherein the second nucleic acid strand comprises one or more phosphorothioated nucleotides located 5' and/or 3' to the at least 4 consecutive RNA nucleotides.

18. The composition according to any one of the items 12 to 17, wherein the second nucleic acid strand further comprises a functional moiety having a function selected from a labeling function, a purification function, and a targeted delivery function.

19. The composition according to any one of the items 14 to 18, wherein the double stranded nucleic acid complex further comprises a third nucleic acid strand annealed to the second nucleic acid strand.

20. The composition according to the item 19, wherein the third nucleic strand hybridizes to the transcription product and comprises (a) a region consisting of at least 4 consecutive nucleotides that are recognized by RNase H when the strand is hybridized to the transcription product, (b) one or more nucleotide analogs located on 5' terminal side of the region, (c) one or more nucleotide analogs located on 3' terminal side of the region and (d) a total number of nucleotides and nucleotide analogs ranging from 8 to 35 nucleotides.

21. The composition according to the item 19, wherein the third nucleic strand hybridizes to another transcription product and comprises (a) a region consisting of at least 4 consecutive nucleotides that are recognized by RNase H when the strand is hybridized to the another transcription product, (b) one or more nucleotide analogs located on 5' terminal side of the region, (c) one or more nucleotide analogs located on 3' terminal side of the region and (d) a total number of nucleotides and nucleotide analogs ranging from 8 to 35 nucleotides.

22. The composition according to any one of the items 19 to 21, wherein the third nucleic acid strand further comprises a functional moiety having a function selected from a labeling function, a purification function, and a targeted delivery function.

In other embodiments of the present invention, the following are provided.

(1) A double-stranded nucleic acid having an activity of suppressing the expression of a target gene by means of an antisense effect, the double-stranded nucleic acid comprising nucleic acids of the following items (a) and (b):

(a) an antisense nucleic acid that is complementary to the transcription product of the target gene and contains a region comprising a DNA of four or more contiguous bases, and (b) a nucleic acid that is complementary to the nucleic acid of (a).

(2) The double-stranded nucleic acid described in the item (1), in which the nucleic acid of (a) further contains a region comprising a modified nucleic acid, which is disposed on at least any one of the 5'-terminal side and the 3'-terminal side of the region comprising a DNA of four or more contiguous bases.

(3) The double-stranded nucleic acid described in the item (2), in which the region comprising a modified nucleic acid of the nucleic acid of (a) is a region comprising a modified nucleic acid, which is disposed on the 5'-terminal side and the 3'-terminal side of the region comprising a DNA of four or more contiguous bases, and the modified nucleic acid is a LNA.

(4) The double-stranded nucleic acid described in any one of the items (1) to (3), in which the nucleic acid of (b) is an RNA or a PNA.

(5) The double-stranded nucleic acid described in any one of the items (1) to (3), in which the nucleic acid of (b) is an RNA, the region complementary to the region comprising a modified nucleic acid of the nucleic acid of (a) is modified, and the modification has an effect of suppressing the decomposition caused by a ribonuclease (RNase).

(6) The double-stranded nucleic acid described in the item (5), in which the modification is 2'-O-methylation and/or phosphorothioation.

(7) The double-stranded nucleic acid described in any one of the items (1) to (6), in which a functional moiety is bonded to the nucleic acid of (b).

(8) The double-stranded nucleic acid described in any one of the items (1) to (7), in which the strand lengths of the nucleic acids of (a) and (b) are the same.

(9) The double-stranded nucleic acid described in any one of the items (1) to (7), in which the strand lengths of the nucleic acids of (a) and (b) are different.

(10) The double-stranded nucleic acid described in the item (9), further including a nucleic acid of the following item (c):

(c) a nucleic acid that is complementary to a region in the nucleic acid having a longer strand length between the nucleic acids of (a) and (b), which is protruding relative to the other nucleic acid.

(11) The double-stranded nucleic acid described in the item (10), in which the nucleic acid of (c) is a PNA.

(12) The double-stranded nucleic acid described in the item (10) or (11), in which a functional moiety is bonded to the nucleic acid of (c).

(13) The double-stranded nucleic acid described in the item (7) or (12), in which the functional moiety is a molecule having an activity of delivering the double-stranded nucleic acid to a target site.

(14) A composition for suppressing the expression of a target gene by means of an antisense effect, the composition containing the double-stranded nucleic acid described in any one of the items (1) to (13) as an active ingredient.

(15) A method of reducing the level of a transcription product in a cell comprising contacting with the cell a composition comprising:

(a) a double-stranded nucleic acid complex comprising a first nucleic acid strand annealed to a second nucleic acid strand, wherein:

the first nucleic acid strand (i) comprises nucleotides and optionally nucleotide analogs, and the total number of nucleotides and optionally nucleotide analogs in the first nucleic acid strand is from 8 to 100, (ii) comprises at least 4 consecutive nucleotides that are recognized by RNase H when the first nucleic acid strand is hybridized to the transcription product, and (iii) the first nucleic acid strand hybridizes to the transcription product; and the second nucleic acid strand comprises nucleotides and optionally nucleotide analogs.

(16) A method of reducing the expression level of a gene in a mammal comprising the step of administering an effective amount to the mammal of a pharmaceutical composition comprising:

(a) a double-stranded nucleic acid complex comprising a first nucleic acid strand annealed to a second nucleic acid strand, wherein:

the first nucleic acid strand (i) comprises nucleotides and optionally nucleotide analogs, and the total number of nucleotides and optionally nucleotide analogs in the first nucleic acid strand is from 8 to 100, (ii) comprises at least 4 consecutive nucleotides that are recognized by RNase H when the first nucleic acid strand is hybridized to a transcription product of the gene, and (iii) the first nucleic acid strand hybridizes to the transcription product; and the second nucleic acid strand comprises nucleotides and optionally nucleotide analogs; and (b) a pahrmaceutically acceptable carrier.

(17) A purified or isolated double stranded nucleic acid complex comprising a first nucleic acid strand annealed to a second nucleic acid strand, wherein:
the first nucleic acid strand (i) comprises nucleotides and optionally nucleotide analogs, and the total number of nucleotides and nucleotide analogs in the first nucleic acid strand is from 8 to 100, (ii) comprises at least 4 consecutive nucleotides that are recognized by RNase H when the first nucleic acid strand is hybridized to a transcription product, (iii) comprises at least one non-natural nucleotide, and (iv) the first nucleic acid strand hybridizes to the transcription product; and
the second nucleic acid strand comprises nucleotides and optionally nucleotide analogs.

(18) A pharmaceutical composition for treating a mammal comprising the double stranded nucleic acid complex of item (17), wherein the transcription product is a mammalian transcription product, and a pharmaceutically acceptable carrier.

In other embodiments of the present invention, the following are provided.

<1> A purified or isolated double stranded nucleic acid complex comprising a first nucleic acid strand annealed to a second nucleic acid strand, wherein:
the first nucleic acid strand comprises DNA nucleotides and optionally nucleotide analogs, wherein a 5' wing region comprising one or more nuclease-resistant nucleotides is located at the 5' terminus and/or a 3' wing region comprising one or more nuclease-resistant nucleotides is located at the 3' terminus, the first nucleic acid strand includes at least 4 consecutive DNA nucleotides, and the total number of DNA nucleotides and nucleotide analogs in the first nucleic acid strand is from 10 to 100 nucleotides;
the first nucleic acid strand further comprises a sequence of at least 10 consecutive nucleotides complementary to a portion of a sequence of a transcription product; and
the second nucleic acid strand comprises:
(i) RNA nucleotides and optionally nucleotide analogs, and optionally a DNA nucleotide; or
(ii) DNA nucleotides and/or nucleotide analogs; or
(iii) PNA nucleotides;
wherein a 5' wing region comprising one or more nuclease-resistant nucleotides is located at the 5' terminus and/or a 3' wing region comprising one or more nuclease-resistant nucleotides is located at the 3' terminus, and where the total number of RNA nucleotides, DNA nucleotides, nucleotide analogs, and PNA nucleotides in the second nucleic acid strand is from 10 to 100 nucleotides.

<2> The double stranded nucleic acid complex of item <1>, wherein the transcription product is a protein-coding transcription product.

<3> The double stranded nucleic acid complex of <1>, wherein the transcription product is a non-protein-coding transcription product.

<4> The double stranded nucleic acid complex of any one of items <1>-<3>, wherein the number of nucleotides in the first nucleic acid strand and the second nucleic acid strand are the same.

<5> The double stranded nucleic acid complex of any one of items <1>-<3>, wherein the number of nucleotides in the first nucleic acid strand and the second nucleic acid strand are different.

<6> The double stranded nucleic acid complex of item <5>, wherein the number of nucleotides in the second nucleic acid strand is greater than the number of nucleotides in the first nucleic acid strand.

<7> The double stranded nucleic acid complex of any one of items <1>-<6>, wherein the first nucleic acid strand comprises a total number of nucleotides ranging from 10 to 35 nucleotides.

<8> The double stranded nucleic acid complex of any one of items <1>-<7>, wherein the nucleotides of the first nucleic acid strand are all nuclease-resistant nucleotides.

<9> The double stranded nucleic acid complex of any one of items <1>-<8>, wherein the 5' wing region of the first nucleic acid strand comprises one or more nucleotide analogs and/or the 3' wing region of the first nucleic acid strand comprises one or more nucleotide analogs located at the 3' terminus.

<10> The double stranded nucleic acid complex of any one of items <1>-<9>, wherein the first strand comprises a 5' wing region of at least 2 consecutive nucleotide analogs at the 5'-terminus and a 3' wing region of at least 2 consecutive nucleotide analogs at the 3'-terminus.

<11> The double stranded nucleic acid complex of item <10>, wherein the 5' wing region and the 3' wing region independently consist of 2 to 10 nucleotide analogs.

<12> The double stranded nucleic acid complex of claim 11, wherein the 5' wing region and the 3' wing region independently consist of 2-3 nucleotide analogs.

<13> The double stranded nucleic acid complex of any one of items <1>-<12>, wherein the first nucleic acid strand comprises at least one nucleotide analog that is a bridged nucleotides.

<14> The double stranded nucleic acid complex of any one of items <1>-<13>, wherein the nucleotide analogs contained in the first nucleic acid strand are bridged nucleotides.

<15> The double stranded nucleic acid complex of item <14>, wherein the bridged nucleotides of the first nucleic acid strand are independently selected from LNA, cEt-BNA, amideBNA (AmNA), and cMOE-BNA.

<16> The double stranded nucleic acid complex of claim <14>, wherein the bridged nucleotides of the second nucleic acid strand are selected from a ribonucleotide in which the carbon atom at the 2'-position and the carbon atom at the 4'-position are bridged by 4'-$(CH_2)_p$—O-2',4'-$(CH_2)_p$—S-2', 4'-$(CH_2)_p$—OCO-2',4'-$(CH_2)_n$—N($R_3$)—O—$(CH_2)_m$-2',
where p, m and n represent an integer from 1 to 4, an integer from 0 to 2, and an integer from 1 to 3, respectively, and $R_3$ represents a hydrogen atom, an alkyl group, an alkenyl group, a cycloalkyl group, an aryl group, an aralkyl group, an acyl group, a sulfonyl group, a fluorescent or chemiluminescent label, a functional group with nucleic acid cleavage activity, or an intracellular or intranuclear localization signal peptide.

<17> The double stranded nucleic acid complex of any one of items <1>-<16>, wherein the DNA nucleotides in first nucleic acid strand are phosorothioated.

<18> The double stranded nucleic acid complex of any one of items <1>-<17>, wherein the nucleotide analogs in the first nucleic acid strand are phosphorothioated.

<19> The double stranded nucleic acid complex of any one of items <1>-<18>, wherein the first nucleic acid strand includes a segment of 4-20 consecutive DNA nucleotides.

<20> The double stranded nucleic acid complex of any one of items <1>-<19>, wherein the first strand comprises (i) a 5' wing region of at least 2 consecutive nucleotide analogs at the 5'-terminus, (ii) a 3' wing region of at least 2 consecutive nucleotide analogs at the 3'-terminus, and (iii) at least 4 consecutive DNA nucleotides.

<21> The double stranded nucleic acid complex of any one of items <1>-<19>, wherein the first strand comprises (i) a 5' wing region of at least 2 consecutive nucleotide analogs at the 5'-terminus, (ii) a 3' wing region of at least 2 consecutive nucleotide analogs at the 3'-terminus, wherein said nucleotide analogs in the 5' wing region and 3' wing region are bridged nucleotides; and (iii) at least 4 consecutive DNA nucleotides; wherein said bridged nucleotides and said DNA nucleotides are phosphorothioated.

<22> The double stranded nucleic acid of any one of items <1>-<21>, wherein the first nucleic acid strand has a length of 12-25 nucleotides.

<23> The double stranded nucleic acid complex of any one of items <1>-<22>, wherein the second nucleic acid strand comprises RNA nucleotides and/or nucleotide analogs, and optionally a DNA nucleotide.

<24> The double stranded nucleic acid complex of item <23>, wherein the 5' wing region of the second nucleic acid strand comprises at least one nucleotide analog, the 3' wing region of the second nucleic acid strand comprises at least one nucleotide analog, and the second nucleic acid strand comprises at least 4 consecutive RNA nucleotides.

<25> The double stranded nucleic acid complex of item <23>, wherein the 5' wing region of the second nucleic acid strand comprises at least one phosphorothioated nucleotide, the 3' wing region of the second nucleic acid strand comprises at least one phosphorothioated nucleotide, and the second nucleic acid strand comprises at least 4 consecutive RNA nucleotides.

<26> The double stranded nucleic acid complex of item <24> or <25>, wherein all nucleotides of the 5' wing and the 3' wing region of the second nucleic acid strand are phosphorothioated.

<27> The double stranded nucleic acid complex of any one of claims <24>-<26>, wherein the nuclease-resistant nucleotides of the second nucleic acid strand are independently selected from a bridged nucleotide and a 2'-O-methylated RNA.

<28> The double stranded nucleic acid complex of item <27>, wherein the bridged nucleotides of the second nucleic acid strand are independently selected from LNA, cEt-BNA, amideBNA (AmNA), and cMOE-BNA.

<29> The double stranded nucleic acid complex of item <27>, wherein the bridged nucleotides of the second nucleic acid strand are selected from a ribonucleotide in which the carbon atom at the 2'-position and the carbon atom at the 4'-position are bridged by 4'-$(CH_2)_p$—O-2',4'-$(CH_2)_p$—S-2', 4'-$(CH_2)_p$-oco-2',4'-$(CH_2)_n$—$N(R_3)$—O—$(CH_2)_m$-2', where p, m and n represent an integer from 1 to 4, an integer from 0 to 2, and an integer from 1 to 3, respectively, and R3 represents a hydrogen atom, an alkyl group, an alkenyl group, a cycloalkyl group, an aryl group, an aralkyl group, an acyl group, a sulfonyl group, a fluorescent or chemiluminescent label, a functional group with nucleic acid cleavage activity, or an intracellular or intranuclear localization signal peptide.

<30> The double stranded nucleic acid complex of item <24>, wherein the second nucleic acid strand comprises (i) a 5' wing region of at least 2 phosphorothioated, 2'-O-methylated RNA nucleotides at the 5'-terminus, (ii) a 3' wing region of at least 2 phosphorothioated, 2'-O-methylated RNA nucleotides at the 3'-terminus, and (iii) at least 4 consecutive natural RNA nucleotides that, independently, are optionally phophorothioated.

<31> The double stranded nucleic acid complex of item <24>, wherein the second nucleic acid strand comprises (i) a 5' wing region of at least 2 phosphorothioated, bridged nucleotides at the 5'-terminus, (ii) a 3' wing region of at least 2 phosphorothioated, bridged nucleotides at the 3'-terminus, and (iii) at least 4 consecutive natural RNA nucleotides that, independently, are optionally phophorothioated.

<32> The double stranded nucleic acid complex of any of items <1>-<22>, wherein the second nucleic acid strand comprises PNA nucleotides.

<33> The double stranded nucleic complex of any of items <23>-<32>, wherein the second nucleic acid strand further comprises a functional moiety having a function selected from a labeling function, a purification function, and a targeted delivery function.

<34> The double stranded nucleic acid complex according to any one of items <1> to <3> and <5> to <33>, wherein the double stranded nucleic acid complex further comprises a third nucleic acid strand annealed to the second nucleic acid strand.

<35> The double stranded nucleic acid according to item <34>, wherein the third nucleic acid strand comprises DNA nucleotides and optionally nucleotide analogs, and includes at least 4 consecutive DNA nucleotides, where the total number of nucleotides is from 10 to 100 nucleotides, said third nucleic acid strand further comprising a sequence of at least 10 consecutive nucleotides complementary to a portion of a sequence of a transcription product.

<36> The double stranded nucleic acid according to item <35>, wherein the third strand comprises (i) a 5' wing region of at least 2 consecutive nucleotide analogs at the 5'-terminus, (ii) a 3' wing region of at least 2 consecutive nucleotide analogs at the 3'-terminus, wherein said nucleotide analogs in the 5' wing region and 3' wing region are bridged nucleotides; and (iii) at least 4 consecutive DNA nucleotides; wherein said bridged nucleotides and said DNA nucleotides are phosphorothioated.

<37> The double stranded nucleic acid according to item <34>, wherein the third nucleic acid strand comprises PNA nucleotides.

<38> The double stranded nucleic complex of any of items <34>-<37>, wherein the third nucleic acid strand further comprises a functional moiety having a function selected from a labeling function, a purification function, and a targeted delivery function.

<39> The double stranded nucleic acid complex according to item 33 or 38, wherein said functional moiety is a molecule selected from a lipid, a peptide, and a protein.

<40> The double stranded nucleic acid complex according to item <39>, wherein the functional moiety is joined to the 3'-terminal nucleotide or the 5'-terminal nucleotide.

<41> The double stranded nucleic acid complex according to item <39> or <40>, wherein the functional moiety is a lipid.

<42> The double stranded nucleic acid complex according to item <41>, wherein the functional moiety is a lipid selected from cholesterol, a fatty acid, a lipid-soluble vitamin, a glycolipid, and a glyceride.

<43> The double stranded nucleic acid complex according to item <41>, wherein the functional moiety is a lipid selected from cholesterol, a tocopherol, and a tocotrienol.

<44> The double stranded nucleic acid complex according to item <39> or <40>, wherein the functional molecule is a peptide or protein selected from a receptor ligand and an antibody.

<45> A pharmaceutical composition comprising a pharmaceutically acceptable carrier and the double stranded nucleic acid complex of any one of items <1> to <44>.

<46> Use of the double stranded nucleic acid complex of any one of items <1> to <44> for the preparation of a medicament for reducing the expression of a gene in a mammal.

<47> Use of the double stranded nucleic acid complex of any one of items <1> to <44> for reducing expression of a gene in a mammal.

<48> A method of reducing expression of a gene in a mammal comprising the step of administering an effective amount to the mammal of a pharmaceutical composition comprising:
a purified or isolated double stranded nucleic acid complex comprising a first nucleic acid strand annealed to a second nucleic acid strand, wherein:
the first nucleic acid strand comprises DNA nucleotides and optionally nucleotide analogs, and includes at least 4 consecutive DNA nucleotides, where the total number of DNA nucleotides and nucleotide analogs in the first nucleic acid strand is from 10 to 100 nucleotides;
the first nucleic acid strand further comprises a sequence of at least 10 consecutive nucleotides complementary to a portion of a sequence of a mammalian transcription product; and
the second nucleic acid strand comprises:
(i) RNA nucleotides and optionally nucleotide analogs, and optionally a DNA nucleotide; or
(ii) DNA nucleotides and/or nucleotide analogs; or
(iii) PNA nucleotides;
where the total number of RNA nucleotides, DNA nucleotides, nucleotide analogs, and PNA nucleotides in the second nucleic acid strand is from 10 to 100 nucleotides; and a pharmaceutically acceptable carrier.

<49> The method of item <48>, wherein the route of administration is enteral.

<50> The method of item <48>, wherein the route of administration is parenteral.

<51> The method of any one of items <48>-<50>, wherein the dosage ranges from 0.001 mg/kg/day to 50 mg/kg/day of the double stranded nucleic acid complex.

<52> The method of any one of items <48>-<51>, wherein the mammal is a human.

According to the above-mentioned embodiments, an antisense nucleic acid can be delivered in a double-stranded complex and the expression of a target gene or the level of a transcription product can be selectively and very effectively suppressed by the antisense nucleic acid. In some embodiments, the double-stranded complex can be delivered to a target site with high specificity and high efficiency by associating a delivery moiety with the complex.

BRIEF DESCRIPTION OF THE DRAWINGS

FIGS. 3A-B are schematic diagrams illustrating examples of suitable embodiments of double-stranded nucleic acid complexes. The 5'-LNA-DNA-LNA-3' strands are antisense nucleic acids complementary to the targeted transcription product. In the diagram, "(s)" represents nucleic acids with phosphorothioate linkages; "(o)" represents nucleic acids with natural phosphorothioate linkages; and "(m/s)" represents RNA that has been phosphorothioated and 2'-O-methylated. Furthermore, "X" represents a functional moiety, and may independently represent a lipid (for example, cholesterol or tocopherol), a sugar or the like, or a protein, a peptide (for example, an antibody) or the like.

FIGS. 7A-B are fluorescence microscopic photographs illustrating the results of observing the liver of a mouse to which fluorescently (Cy3)-labeled "LNA" (in accordance with FIG. 6A) or fluorescently (Cy3)-labeled "chol-LNA" (in accordance with FIG. 6B) has been administered.

FIG. 22 is a graph illustrating the results obtained by evaluating the antisense effect of the double-stranded nucleic acid complex composed of three strands: the antisense strand, a complementary strand comprising RNA, and a PNA strand for binding to a peptide or the like.

DETAILED DESCRIPTION OF THE PREFERRED EMBODIMENTS

Double-stranded nucleic acid complexes including an antisense nucleic acid and a nucleic acid complementary to the antisense nucleic acid.

Certain embodiments include a double-stranded nucleic acid complex comprising a first nucleic acid strand annealed to a second nucleic acid strand, wherein:
(i) the first nucleic acid strand hybridizes to the transcription product and comprises (a) a region consisting of at least 4 consecutive nucleotides that are recognized by RNase H when the strand is hybridized to the transcription product, (b) one or more nucleotide analogs located on 5' terminal side of the region, (c) one or more nucleotide analogs located on 3' terminal side of the region and (d) a total number of nucleotides and nucleotide analogs ranging from 8 to 35 nucleotides and
(ii) the second nucleic acid strand comprises (a) nucleotides and optionally nucleotide analogs and (b) at least 4 consecutive RNA nucleotides.

Other embodiments include a purified or isolated double-stranded nucleic acid complex comprising a first nucleic acid annealed to a second nucleic acid, which has an activity of suppressing the expression of a target gene or more generally the level of a transcription product, by means of an antisense effect.

The first nucleic acid strand (i) comprises nucleotides and optionally nucleotide analogs, and the total number of nucleotides and nucleotide analogs in the first nucleic acid strand is from 8 to 100, (ii) comprises at least 4 consecutive nucleotides that are recognized by RNase H when the first nucleic acid strand is hybridized to a transcription product, (iii) comprises at least one non-natural nucleotide, and (iv) the first nucleic acid strand hybridizes to the transcription product; and the second nucleic acid strand comprises nucleotides and optionally nucleotide analogs, and
the second nucleic acid strand can anneal to the first nucleic acid strand The second nucleic acid strand comprises:
(i) an RNA nucleotide and optionally a nucleotide analog, and optionally a DNA nucleotide; or
(ii) a DNA nucleotide and/or a nucleotide analog; or
(iii) PNA nucleotides.

As used herein, "first nucleic acid strand", "second nucleic acid strand" and "third nucleic acid strand" are also referred to "first strand", "second strand" and "third strand" respectively.

Figure 1:
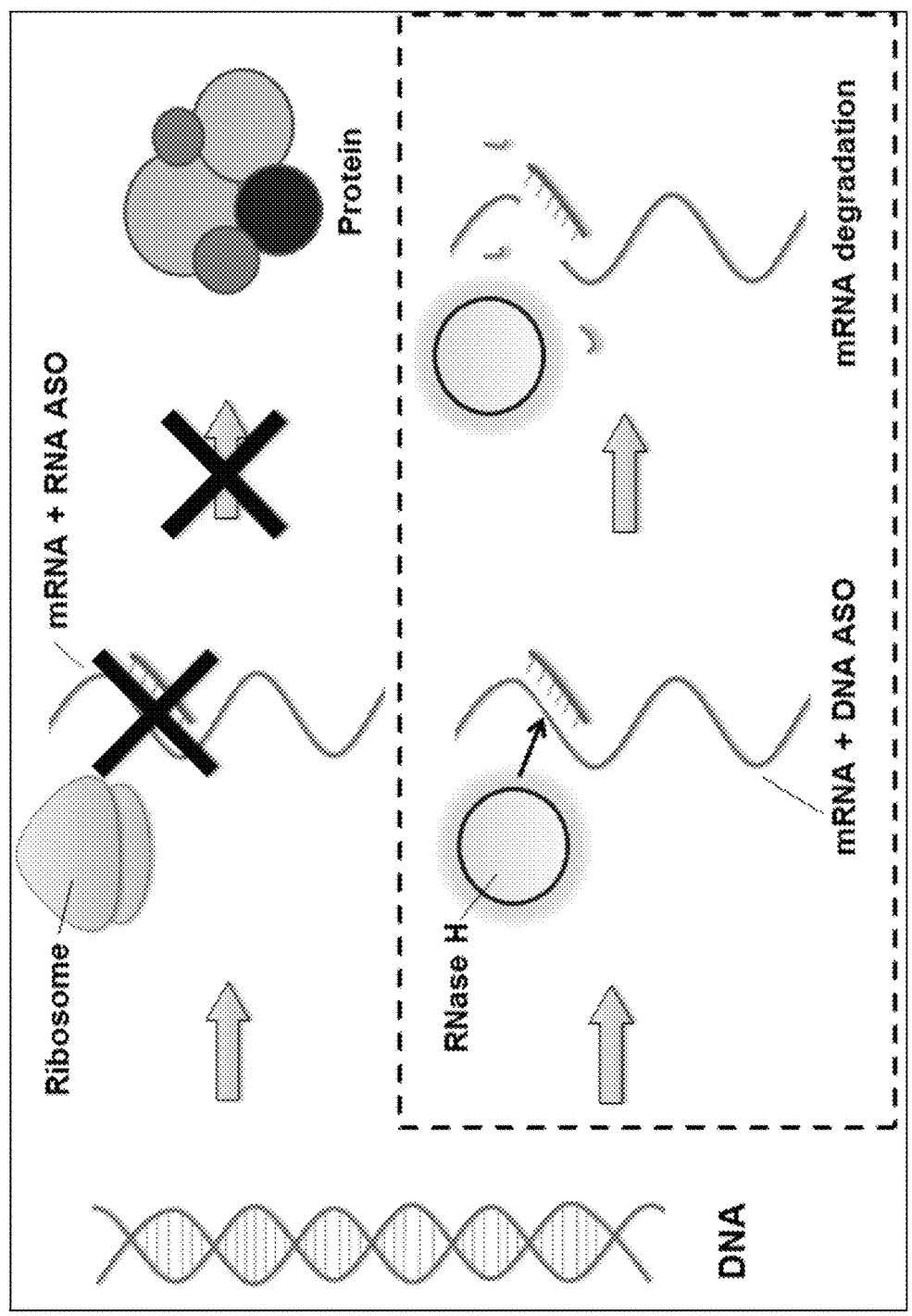
FIG. 1 is a diagram illustrating the general mechanisms of certain antisense methods. As illustrated in the diagram, when an oligonucleotide (antisense oligonucleotide (ASO)) ("DNA" in the diagram) that is complementary to a partial sequence of the mRNA of a target gene is introduced into a cell, the expression of a protein that is encoded by the target gene is selectively inhibited. In the dashed box, a degradation mechanism is shown in which RNase H cleaves mRNA at a location at which it is hybridized to an ASO. As a result of RNase H cleavage, the mRNA generally will not be translated to produce a functional gene expression product.
Figure 2:
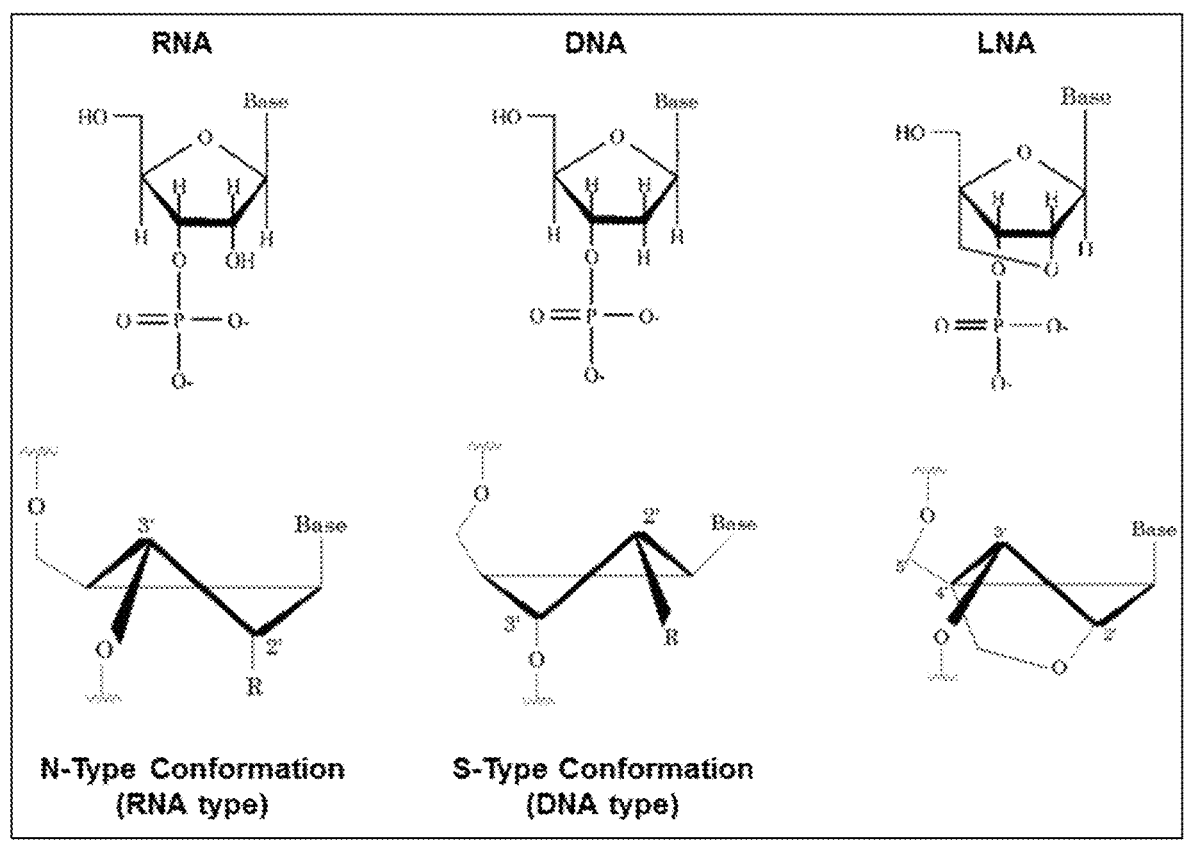
FIG. 2 is a schematic diagram illustrating the structures of RNA, DNA, and an LNA nucleotide.

The "antisense effect" means suppressing the expression of a target gene or the level of a targeted transcription product, which occurs as a result of hybridization of the targeted transcription product (RNA sense strand) with, for example, a DNA strand, or more generally strand designed to cause the antisense effect, complementary to a partial sequence of the transcription product or the like, wherein in certain instances inhibition of translation or a splicing function modifying effect such as exon skipping (see the description in the upper part outside the area surrounded by dotted lines in FIG. 1) may be caused by covering of the transcription product by the hybridization product, and/or decomposition of the transcription product may occur as a result of recognition of the hybridized portion (see the description within the area surrounded by dotted lines in FIG. 1).

The "target gene" or "targeted transcription product" whose expression is suppressed by the antisense effect is not particularly limited, and examples thereof include genes whose expression is increased in various diseases. Also, the "transcription product of the target gene" is a mRNA transcribed from the genomic DNA that encodes the target gene, and also includes a mRNA that has not been subjected to base modification, a mRNA precursor that has not been spliced, and the like. More generally, the "transcription product" may be any RNA synthesized by a DNA-dependent RNA polymerase.

The term "purified or isolated double-stranded nucleic acid complex" as used herein means a nucleic acid complex that comprises at least one nucleic strand that does not occur in nature, or is essentially free of naturally occurring nucleic acid materials.

The term "complementary" as used herein means a relationship in which so-called Watson-Crick base pairs (natural type base pair) or non-Watson-Crick base pairs (Hoogsteen base pairs and the like) can be formed via hydrogen bonding. It is not necessary that the base sequence of the targeted transcription product, e.g., the transcription product of a target gene, and the base sequence of the first nucleic acid strand be perfectly complementary, and it is acceptable if the base sequences have a complementary of at least 70% or higher, preferably 80% or higher, and more preferably 90% or higher (for example, 95%, 96%, 97%, 98%, or 99% or higher). The complementary of sequences can be determined by using a BLAST program or the like. A first strand can be "annealed" to a second strand when the sequences are complementary. A person of ordinary skill in the art can readily determine the conditions (temperature, salt concentration, etc.) under which two strands can be annealed. Also, a person having ordinary skill in the art can easily design an antisense nucleic acid complementary to the targeted transcription product based on the information of the base sequence of, e.g., the target gene.

The first nucleic acid strand according to certain embodiments is an antisense nucleic acid complementary to a transcription product, such as that of a target gene, and is a nucleic acid containing a region comprising at least 4 consecutive nucleotides that are recognized by RNase H when the first nucleic acid strand is hybridized to the transcription product.

As used herein, the term "nucleic acid" may refer to a monomeric nucleotide or nucleoside, or may mean an oligonucleotide consisting of plural monomers. The term "nucleic acid strand" is also used herein to refer to an oligonucleotide. Nucleic acid strands may be prepared in whole or in part by chemical synthesis methods, including using a automated synthesizer or by enzymatic processes, including but not limited to polymerase, ligase, or restriction reactions.

The strand length of the first nucleic acid strand is not particularly limited, but the strand length is usually at least 8 bases, at least 10 bases, at least 12 bases, or at least 13 bases. The strand length may be up to 20 bases, 25 bases, or 35 bases. The strand length may even be as long as about 100 bases. Ranges of the length may be 8 to 35 bases, 10 to 35 bases, 12 to 25 bases, or 13 to 20 bases. In certain instances, the choice of length generally depends on a balance of the strength of the antisense effect with the specificity of the nucleic acid strand for the target, among other factors such as cost, synthetic yield, and the like.

The "at least four consecutive nucleotides that are recognized by RNase H" is usually a region comprising 4 to 20 consecutive bases, a region comprising 5 to 16 consecutive bases, or a region comprising 6 to 12 consecutive bases. Furthermore, nucleotides that may be used in this region are those that, like natural DNA, are recognized by RNase H when hybridized to RNA nucleotides, wherein the RNase H cleaves the RNA strand. Suitable nucleotides, such as modified DNA nucleotides and other bases are know in the art. Nucleotides that contain a 2'-hydroxy group, like an RNA nucleotide are known to not be suitable. One of skill in the art can readily determine the suitability of a nucleotide for use in this region of "at least four consecutive nucleotides."

In certain embodiments, the first nucleic acid strand comprises "nucleotides and optionally nucleotide analogs." This term means that the first strand includes DNA nucleotides, RNA nucleotides, and optionally may further include nucleotide analogs in the strand.

As used herein, "DNA nucleotide" means a naturally occurring DNA nucleotide, or a DNA nucleotide with a modified base, sugar, or phosphate linkage subunit. Similarly, "RNA nucleotide" means a naturally occurring RNA nucleotide, or an RNA nucleotide with a modified base, sugar, or phosphate linkage subunit. A modified base, sugar, or phosphate linkage subunit is one in which a single substituent has been added or substituted in a subunit, and the subunit as a whole has not been replaced with a different chemical group. From the viewpoint that a portion or the entirety of the region comprising the nucleotide has high resistance to deoxyribonuclease and the like, the DNA may be a modified nucleotide. Examples of such modification include 5-methylation, 5-fluorination, 5-bromination, 5-iodination, and N4-methylation of cytosine; 5-demethylation, 5-fluorination, 5-bromination, and 5-iodination of thymidine; N6-methylation and 8-bromination of adenine; N2-methylation and 8-bromination of guanine; phosphorothioation, methylphosphonation, methylthiophosphonation, chiral methylphosphonation, phosphorodithioation, phosphoroamidation, 2'-O-methylation, 2'-methoxyethyl(MOE)ation, 2'-aminopropyl(AP)ation, and 2'-fluorination. However, from the viewpoint of having excellent pharmacokinetics, phosphorothioation is preferred. Such modification may be carried out such that the same DNA may be subjected to plural kinds of modifications in combination. And, as discussed below, RNA nucleotides may be modified to achieve a similar effect.

In certain instances, the number of modified DNA's and the position of modification may affect the antisense effect and the like provided by the double-stranded nucleic acid of the as disclosed herein. Since these embodiments may vary with the sequence of the target gene and the like, it may depend on cases, but a person having ordinary skill in the art can determine suitable embodiments by referring to the descriptions of documents related to antisense methods. Furthermore, when the antisense effect possessed by a double-stranded nucleic acid complex after modification is measured, if the measured value thus obtained is not significantly lower than the measured value of the double-stranded nucleic acid complex before modification (for example, if the measured value obtained after modification is lower by 30% or more than the measured value of the double-stranded nucleic acid complex before modification), the relevant modification can be evaluated. The measurement of the antisense effect can be carried out, as indicated in the Examples below, by introducing a nucleic acid compound under test into a cell or the like, and measuring the amount of expression (amount of mRNA, amount of cDNA, amount of a protein, or the like) of the target gene in the cell in which the expression is suppressed by the antisense effect provided by the nucleic acid compound under test, by appropriately using known techniques such as Northern Blotting, quantitative PCR, and Western Blotting.

As used herein, "nucleotide analog" means a non-naturally occurring nucleotide, wherein the base, sugar, or phosphate linkage subunit has more than one substituent added or substituted in a subunit, or that the subunit as a whole has been replaced with a different chemical group. An example of an analog with more than one substitution is a bridged nucleic acid, wherein a bridging unit has been added by virtue of two substitutions on the sugar ring, typically linked to the 2' and 4' carbon atoms. In regard to the first nucleic acid strand according to certain embodiments, from the viewpoint of increasing the affinity to a partial sequence of the transcription product of the target gene and/or the resistance of the target gene to a nuclease, the first nucleic acid strand further comprises a nucleotide analog. The "nucleotide analog" may be any nucleic acid in which, owing to the modifications (bridging groups, substituents, etc.), the affinity to a partial sequence of the transcription product of the target gene and/or the resistance of the nucleic acid to a nuclease is enhanced, and examples thereof include nucleic acids that are disclosed to be suitable for use in antisense methods, in JP 10-304889 A, WO 2005/021570, JP 10-195098 A, JP 2002-521310 W, WO 2007/143315, WO 2008/043753, WO 2008/029619, and WO 2008/049085 (hereinafter, these documents will be referred to as "documents related to antisense methods"). That is, examples thereof include the nucleic acids disclosed in the documents described above: a hexitol nucleic acid (HNA), a cyclohexane nucleic acid (CeNA), a peptide nucleic acid (PNA), a glycol nucleic acid (GNA), a threose nucleic acid (TNA), a morpholino nucleic acid, a tricyclo-DNA (tcDNA), a 2'-O-methylated nucleic acid, a 2'-MOE (2'-O-methoxyethyl)lated nucleic acid, a 2'-AP (2'-O-aminopropyl)lated nucleic acid, a 2'-fluorinated nucleic acid, a 2'-F-arabino-nucleic acid (2'-F-ANA), and a BNA (bridged nucleic acid).

The BNA according to certain embodiments may be any ribonucleotide or deoxyribonucleotide in which the 2' carbon atom and 4' carbon atom are bridged by two or more atoms. Examples of bridged nucleic acids are known to those of skill in the art. One subgroup of such BNA's can be described as having the carbon atom at the 2'-position and the carbon atom at the 4'-position bridged by 4'-$(CH_2)_p$—O-2',4'-$(CH_2)_p$—S-2',4'-$(CH_2)_p$—OCO-2',4'-$(CH_2)_n$—N($R_3$)—O—$(CH_2)_m$-2' (here, p, m and n represent an integer from 1 to 4, an integer from 0 to 2, and an integer from 1 to 3, respectively; and R3 represents a hydrogen atom, an alkyl group, an alkenyl group, a cycloalkyl group, an aryl group, an aralkyl group, an acyl group, a sulfonyl group, and a unit substituent (a fluorescent or chemiluminescent labeling molecule, a functional group having nucleic acid cleavage activity, an intracellular or intranuclear localization signal peptide, or the like)). Furthermore, in regard to the BNA according certain embodiments, in the $OR_2$ substituent on the carbon atom at the 3'-position and the $OR_1$ substituent on the carbon atom at the 5'-position, $R_1$ and $R_2$ are typically hydrogen atoms, but may be identical with or different from each other, and may also be a protective group of a hydroxyl group for nucleic acid synthesis, an alkyl group, an alkenyl group, a cycloalkyl group, an aryl group, an aralkyl group, an acyl group, a sulfonyl group, a silyl group, a phosphoric acid group, a phosphoric acid group protected by a protective group for nucleic acid synthesis, or —$P(R_4)R_5$ (here, $R_4$ and $R_5$, which may be identical with or different from each other, each represent a hydroxyl group, a hydroxyl group protected by a protective group for nucleic acid synthesis, a mercapto group, a mercapto group protected by a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 5 carbon atoms). Non-limiting examples of such a BNA include α-L-methyleneoxy(4'-$CH_2$—O-2') BNA or β-D-methyleneoxy(4'-$CH_2$—O-2')BNA, which are also known as LNA (Locked Nucleic Acid (registered trademark), 2',4'-BNA), ethyleneoxy(4'-$CH_2$)2-O-2')BNA which is also known as ENA, β-D-thio(4'-$CH_2$—S-2')BNA, aminooxy(4'-$CH_2$—O—N($R_3$)-2')BNA, oxyamino(4'-$CH_2$—N($R_3$)—O-2')BNA which is also known as 2',4'-BNANC, 2',4'-BNACOC, 3'-amino-2',4'-BNA, 5'-methyl BNA, (4'-$CH(CH_3)$—O-2')BNA, which is also known as cEt-BNA, (4'-$CH(CH_2OCH_3)$—O-2')BNA, which is also known as cMOE-BNA, amideBNA (4'-C(O)—N(R)-2')BNA (R=H, Me), which is also known as AmNA, and other BNA's known to those of skill in the art.

Furthermore, in the nucleotide analog, according to certain embodiments, a base moiety may be modified. Examples of the modification at a base moiety include 5-methylation, 5-fluorination, 5-bromination, 5-iodination, and N4-methylation of cytosine; 5-demethylation, 5-fluorination, 5-bromination, and 5-iodination of thymidine; N6-methylation and 8-bromination of adenine; and N2-methylation and 8-bromination of guanine. Furthermore, in the modified nucleic acid according to certain embodiments, a phosphoric acid diester binding site may be modified. Examples of the modification of the phosphoric acid diester binding site include phosphorothioation, methylphosphonation, methylthiophosphonation, chiral methylphosphonation, phosphorodithioation, and phosphoroamidation. However, from the viewpoint of having excellent pharmacokinetics, phosphorothioation may be used. Also, such modification of a base moiety or modification of a phosphoric acid diester binding site may be carried out such that the same nucleic acid may be subjected to plural kinds of modifications in combination.

Generally, modified nucleotides and modified nucleotide analogs are not limited to those exemplified herein. Numerous modified nucleotides and modified nucleotide analogs are known in art, such as, for example those disclosed in U.S. Pat. No. 8,299,039 to Tachas et al., particularly at col. 17-22, and may be used in the embodiments of this application.

A person having ordinary skill in the art can appropriately select and use a nucleotide analog among such modified nucleic acids while taking consideration of the antisense effect, affinity to a partial sequence of the transcription product of the target gene, resistance to a nuclease, and the like. However, the nucleotide analog in some embodiments is a LNA represented by the following formula (1):

[Chem. 1]

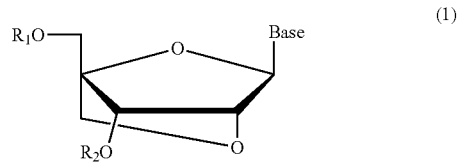

(1)

In formula (1), "Base" represents an aromatic heterocyclic group or aromatic hydrocarbon ring group which may be substituted, for example, a base moiety (purine base or pyrimidine base) of a natural nucleoside, or a base moiety of a non-natural (modified) nucleoside, while examples of modification of the base moiety include those described above; and $R_1$ and $R_2$, which may be identical with or different from each other, each represent a hydrogen atom, a protective group of a hydroxyl group for nucleic acid synthesis, an alkyl group, an alkenyl group, a cycloalkyl group, an aryl group, an aralkyl group, an acyl group, a sulfonyl group, a silyl group, a phosphoric acid group, a phosphoric acid group protected by a protective group for nucleic acid synthesis, or —$P(R_4)R_5$ [here, $R_4$ and $R_5$, which may be identical or different from each other, each represent a hydroxyl group, a hydroxyl group protected by a protective group for nucleic acid synthesis, a mercapto group, a mercapto group protected by a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 5 carbon atoms.

The compounds shown by the above chemical formulas are represented as nucleosides, but the "LNA" and more generally, the BNA according to certain embodiments include nucleotide forms in which a phosphoric acid derived group is bound to the relevant nucleoside (nucleotide). In other words, BNA's, such as LNA, are incorporated as nucleotides in the nucleic strands that comprise the double stranded nucleic acid complex.

The "wing region comprising one or more nucleotide analogs" according to certain embodiments is located on the 5'-terminal side and/or the 3'-terminal side of the region comprising at least four consecutive DNA nucleotides (hereinafter, also called "DNA gap region").

The region comprising a nucleotide analog that is disposed to the 5'-terminus of the DNA gap region (hereinafter, also called "5' wing region") and the region comprising a nucleotide analog that is disposed to the 3'-terminus of the DNA gap region (hereinafter, also called "3' wing region") may each independently comprise at least one kind of a nucleotide analog that is discussed in the documents related to antisense methods, and may further comprise a natural nucleic acid (DNA or RNA) in addition to such a nucleotide analog. Furthermore, the strand lengths of the 5' wing region and the 3' wing region are independently usually 1 to 10 bases, 1 to 7 bases, or 2 to 5 bases. Preferably, the numbers of the nucleotide analogs comprised in each wing region are at least 2 bases.

Furthermore, there are suitable embodiments of the number of kinds and position of the nucleotide analog and the natural nucleotide in the 5' wing region and the 3' wing region, since the number and the position of those nucleic acids may affect the antisense effect and the like provided by the double-stranded nucleic acid complex in certain embodiments. Since these suitable embodiments may vary with the sequence and the like, it may depend on cases, but a person having ordinary skill in the art can determine the suitable embodiments by referring to the descriptions of documents related to antisense methods. Furthermore, when the antisense effect possessed by a double-stranded nucleic acid after modification is measured in the same manner as in the case of the region comprising "at least four consecutive DNA nucleotides," if the measured value thus obtained is not significantly lower than that of a double-stranded nucleic acid before modification, the relevant modification can be evaluated as a preferred embodiment.

Meanwhile, antisense methods involving an RNA or a LNA only that have been traditionally attempted have suppressed translation through binding to a target mRNA; however, their effects are typically insufficient. On the other hand, in antisense methods involving a DNA only, since a double-stranded structure composed of a DNA and an RNA is obtained once the DNA binds to a target gene transcript, a strong target gene expression suppressing effect could be expected to be obtained by making the DNA-RNA heteroduplex a target of RNase H and thereby cleaving the mRNA. However, since the binding of DNA itself to the target RNA is weak, the actual effect has also typically been insufficient.

Therefore, when a DNA having a strand length of at least four or more bases is disposed at the center of a first nucleic acid strand, and a LNA (or other BNA) having a strong binding affinity to RNA (i.e., to the targeted transcription product) is disposed at both ends of this first strand, such a composite strand thereby promotes cleavage of the target RNA by RNase H. The "DNA having a strand length of four" is not however limited to just DNA nucleotides. It is contemplated that the first nucleic acid strand comprises at least 4 consecutive nucleotides that are recognized by RNase H when the first nucleic acid strand is hybridized to a transcription product. From the viewpoint that the antisense effect occurring as a result of heteroduplex formation with the targeted transcription product is excellent, the optional inclusion of nucleotide analogs according to certain embodiments in regions comprising a modified nucleic acid disposed on the 5' side and the 3' side of the region comprising at least four consecutive nucleotides that are recognized by RNase H when the first nucleic acid strand is hybridized to a transcription product, is desirable. The nucleotide analog may be a BNA, such as, e.g., LNA.

The second nucleic acid strand according to some embodiments of is a nucleic acid complementary to the first nucleic acid strand described above. It is not necessary that the base sequence of the second nucleic acid strand and the base sequence of the first nucleic acid strand be perfectly complementary to each other, and the base sequences may have a complementary of at least 70% or higher, preferably 80% or higher, and more preferably 90% or higher (for example, 95%, 96%, 97%, 98%, 99% or higher).

The second nucleic acid strand is an oligonucleotide comprising at least one kind of nucleic acid selected from RNA, DNA, PNA (peptide nucleic acid) and BNA (e.g., LNA). More specifically, the second nucleic acid strand may comprise (a) nucleotides and optionally nucleotide analogs and (b) at least 4 consecutive RNA nucleotides; or (i) an RNA nucleotide and optionally a nucleotide analog, and optionally a DNA nucleotide; or (ii) a DNA nucleotide and/or a nucleotide analog; or (iii) PNA nucleotides.

The term "nucleotides and optionally nucleotide analogs." means that the second nucleic acid strand includes DNA nucleotides, RNA nucleotides, and optionally may further include nucleotide analogs in the strand.

The term "RNA nucleotides and optionally nucleotide analogs, and optionally a DNA nucleotide" means that the second strand includes RNA nucleotides, and optionally may further include nucleotide analogs in the strand, and optionally may further include DNA nucleotides in the strand. The term "DNA nucleotides and/or nucleotide analogs" means that the second strand may include either DNA nucleotides or nucleotide analogs, or may include both DNA nucleotides and nucleotide analogs. The term "PNA nucleotides" means that the second strand may be composed of PNA nucleotides.

However, as will be described in the Examples that follow, from the viewpoint that when the double-stranded nucleic acid complex of certain embodiments is recognized by RNase H in the cell and the second nucleic acid strand is decomposed, the antisense effect of the first nucleic acid strand is readily exhibited, the second nucleic acid strand comprises RNA nucleotides. Furthermore, from the viewpoint that a functional molecule such as a peptide can be easily bound to the double-stranded nucleic acid complex of some embodiments, the second nucleic acid strand is a PNA.

As used herein, "RNA nucleotide" means a naturally occurring RNA nucleotide, or an RNA nucleotide with a modified base, sugar, or phosphate linkage subunit. A modified base, sugar, or phosphate linkage subunit is one in which a single substituent has been added or substituted in a subunit, and the subunit as a whole has not been replaced with a different chemical group.

In regard to the second nucleic acid strand, a portion or the entirety of the nucleic acid may be a modified nucleotide, from the viewpoint of having high resistance to a nuclease such as a ribonuclease (RNase). Examples of such modification include 5-methylation, 5-fluorination, 5-bromination, 5-iodination and N4-methylation of cytosine; 5-demethylation, 5-fluorination, 5-bromination, and 5-iodination of thymidine; N6-methylation and 8-bromination of adenine; N2-methylation and 8-bromination of guanine; phosphorothioation, methylphosphonation, methylthiophosphonation, chiral methylphosphonation, phosphorodithioation, phosphoroamidation, 2'-O-methylation, 2'-methoxyethyl(MOE)ation, 2'-aminopropyl(AP)lation, and 2'-fluorination. Also, an RNA nucleotide with a thymidine base substituted for a uracil base is also contemplated. However, from the viewpoint of having excellent pharmacokinetics, phosphorothioation is used. Furthermore, such modification may be carried out such that the same nucleic acid may be subjected to plural kinds of modifications in combination. For example, as used in the Examples described below, the same RNA may be subjected to phosphorothioation and 2'-O-methylation in order to provide resistance to enzymatic cleavage. However, where it is expected or desired for an RNA nucleotide to be cleaved by RNase H, then only either phosphorothioation or 2'-O-methylation can be applied.

There are suitable embodiments of the number of nucleotide analogs and the position of modification with regard to the second nucleic acid strand, since the number and the position of modification may affect the antisense effect and the like provided by the double-stranded nucleic acid complex in certain embodiments. Since these suitable embodiments may vary with the type, sequence and the like of the nucleic acid to be modified, it may depend on cases, but the type, sequence and the like can be characterized by measuring the antisense effect possessed by the double-stranded nucleic acid after modification in the same manner as in the case of the first nucleic acid strand described above. According to such a suitable embodiment, from the viewpoint that while the decomposition by a ribonuclease such as RNase A is suppressed until the second nucleic acid strand is delivered into the nucleus of a particular cell, the second nucleic acid strand can easily exhibit the antisense effect by being decomposed by RNase H in the particular cell, the second nucleic acid strand is an RNA, a region complementary to the region of the first nucleic acid strand comprising a nucleotide analog (i.e., 5' wing region and/or 3' wing region) is a modified nucleic acid or is a nucleotide analog, and the modification or the analog has an effect of suppressing decomposition by enzymes, such as a ribonuclease. According to certain embodiments, the modification is 2'-O-methylation and/or phosphorothioation of RNA. Furthermore, in this case, the entire region that is complementary to the region of the first nucleic acid strand comprising a nucleotide analog may be modified, or a portion of the region that is complementary to the region comprising a modified nucleic acid of the first nucleic acid strand may be modified. In addition, the region that is modified may be longer than the region comprising a modified nucleic acid of the first nucleic acid strand, or may be shorter, as long as the region that is modified comprises that portion. Preferably, the second nucleic acid strand comprises one or more phosphorothioated nucleotides located 5' and/or 3' to the at least 4 consecutive RNA nucleotides.

In the double-stranded nucleic acid complex of certain embodiments, a functional moiety may be bonded to the second nucleic acid strand. The bonding between the second nucleic acid strand and the functional moiety may be direct bonding, or may be indirect bonding mediated by another material. However, in certain embodiments, it is preferable that a functional moiety be directly bonded to the second nucleic acid strand via covalent bonding, ionic bonding, hydrogen bonding or the like, and from the viewpoint that more stable bonding may be obtained, covalent bonding is more preferred.

There are no particular limitations on the structure of the "functional moiety" according to certain embodiments, provided it imparts the desired function to the double-stranded nucleic acid complex and/or the strand to which it is bound. The desired functions include a labeling function, a purification function, and a delivery function. Examples of moieties that provide a labeling function include compounds such as fluorescent proteins, luciferase, and the like. Examples of moieties that provide a purification function include compounds such as biotin, avidin, a His tag peptide, a GST tag peptide, a FLAG tag peptide, and the like.

Furthermore, from the viewpoint of delivering the first nucleic acid strand to a target site with high specificity and high efficiency, and thereby suppressing very effectively the expression of a target gene by the relevant nucleic acid, it is preferable that a molecule having an activity of delivering the double-stranded nucleic acid complex of some embodiments to a "target site" within the body, be bonded as a functional moiety to the second nucleic acid strand.

The moiety having a "targeted delivery function" may be, for example, a lipid, from the viewpoint of being capable of delivering the double-stranded nucleic acid complex of certain embodiments to the liver or the like with high specificity and high efficiency. Examples of such a lipid include lipids such as cholesterol and fatty acids (for example, vitamin E (tocopherols, tocotrienols), vitamin A, and vitamin D); lipid-soluble vitamins such as vitamin K (for example, acylcarnitine); intermediate metabolites such as acyl-CoA; glycolipids, glycerides, and derivatives thereof. However, among these, from the viewpoint of having higher safety, in certain embodiments, cholesterol and vitamin E (tocopherols and tocotrienols) are used. Furthermore, from the viewpoint of being capable of delivering the double-stranded nucleic acid complex of certain embodiments to the brain with high specificity and high efficiency, examples of the "functional moiety" according to the certain embodiments include sugars (for example, glucose and sucrose). Also, from the viewpoint of being capable of delivering the double-stranded nucleic acid complex of certain embodiments to various organs with high specificity and high efficiency by binding to the various proteins present on the cell surface of the various organs, examples of the "functional moiety" according to certain embodiments include peptides or proteins such as receptor ligands and antibodies and/or fragments thereof.

Figure 3A:
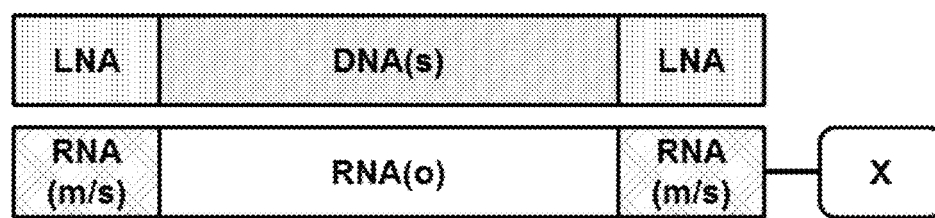
Figure 3B:
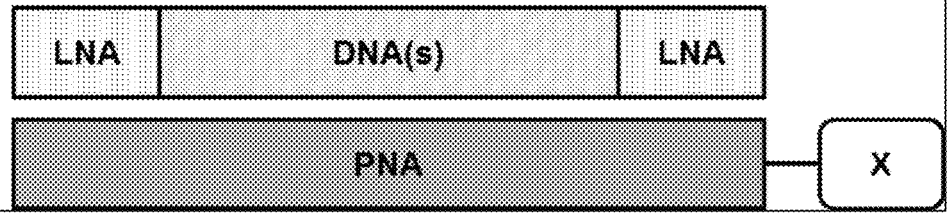

In regard to the double-stranded nucleic acid complex of certain embodiments, the strand length of the first nucleic acid strand and the strand length of the second nucleic acid strand may be identical or may be different. As the double-stranded nucleic acid complex of some embodiments in which the first and second nucleic acid strands have the same strand length, for example, the double-stranded nucleic acids illustrated in FIGS. 3A-B are an example of such embodiments.

Furthermore, as the double-stranded nucleic acid of some embodiments in which the first and second nucleic acid strands have different strand lengths, for example, the double-stranded nucleic acids illustrated in FIGS. 4A-B and FIGS. 5A-B are examples of such embodiments. That is, some embodiments can provide a double-stranded nucleic acid which further comprises a third nucleic acid strand in addition to the first and second nucleic acid strands described above.

The third nucleic acid strand is complementary to a region of whichever is the longer of the first and second nucleic acid strands, which region is protruding relative to the other nucleic acid.

The third nucleic acid strand according to some embodiments can serve as an antisense oligonucleotide, like the first nucleic acid strand. As such, the third strand can target the same sequence or a different sequence than the first strand. Thus the structure and nucleotide composition discussed in relation to the first strand can be similarly applied to the structure and composition of the third strand.

More specifically, the third nucleic strand may hybridize to the transcription product and may comprise (a) a region consisting of at least 4 consecutive nucleotides that are recognized by RNase H when the strand is hybridized to the transcription product, (b) one or more nucleotide analogs located on 5' terminal side of the region, (c) one or more nucleotide analogs located on 3' terminal side of the region and (d) a total number of nucleotides and nucleotide analogs ranging from 8 to 35 nucleotides.

Here, "the transcription product" means the transcription product to which the first nucleic acid strand hybridizes.

In addition, the third nucleic strand may hybridize to another transcription product and may comprise (a) a region consisting of at least 4 consecutive nucleotides that are recognized by RNase H when the strand is hybridized to the another transcription product, (b) one or more nucleotide analogs located on 5' terminal side of the region, (c) one or more nucleotide analogs located on 3' terminal side of the region and (d) a total number of nucleotides and nucleotide analogs ranging from 8 to 35 nucleotides.

As used herein, "another transcription product" means a different transcription product than the first strand hybridizes.

Furthermore, similarly to the second nucleic acid strand, by causing the functional moieties described above to be directly or indirectly bonded to the third nucleic acid strand, various functions can be imparted to the third nucleic acid strand, for example, it can be made to function as a delivery agent of the complex.

Figure 4A:
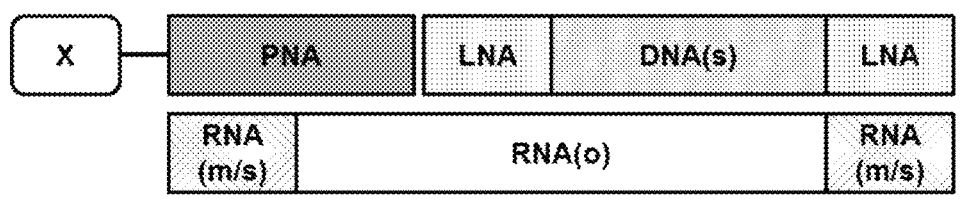
FIGS. 4A-B are schematic diagrams illustrating examples of suitable embodiments of a double-stranded nucleic acid complexes that contain three strands: a first ASO nucleic acid strand and a second complementary nucleic acid strand, that have different strand lengths, and a third nucleic acid strand comprising a PNA to which is bound a functional molecule such as a peptide, an antibody, or the like. Symbols in the diagram have the same meanings as those defined in FIGS. 3A-B.
Figure 4B:
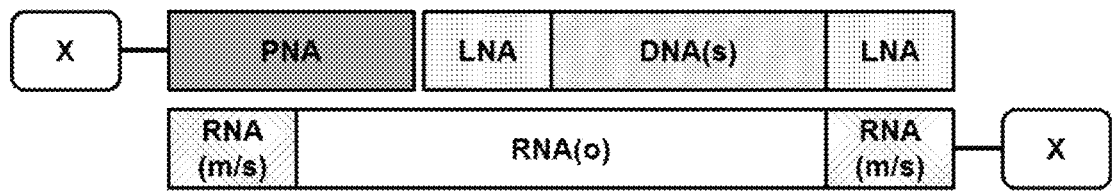
Figure 5A:
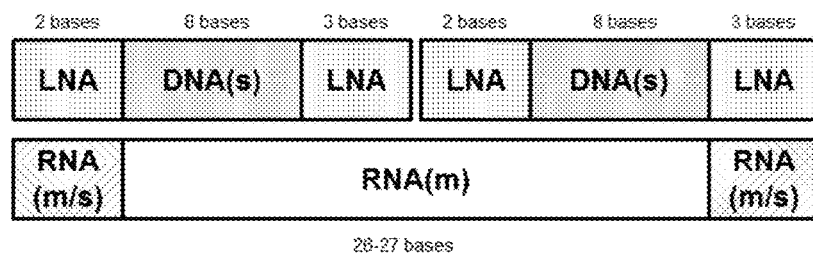
FIGS. 5A-B are schematic diagrams illustrating examples of suitable embodiments of a double-stranded nucleic acid complex that have at least a first ASO nucleic acid strand and a second complementary nucleic acid strand that have different chain lengths. In these embodiments, either (A) the nucleic acid further comprises a third nucleic acid strand complementary to the second nucleic acid strand or (B) the second nucleic acid strand further comprises a self-complementary region of phosphorothioated DNA attached to the second nucleic acid strand by a hairpin linker. Furthermore, in the diagram, "(m)" represents a 2'-O-methylated RNA. Other symbols have the same meanings as those defined in FIGS. 3A-B.
Figure 5B:
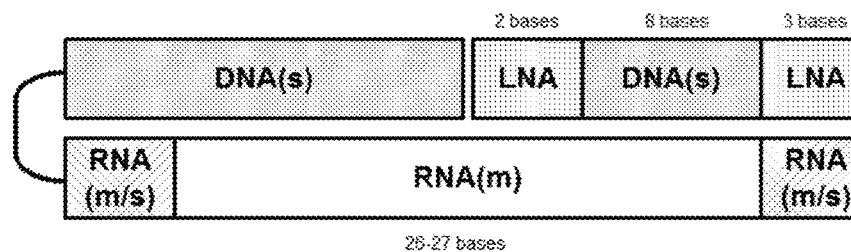

For example, as illustrated in FIGS. 4A-B, when a PNA is used as the third nucleic acid strand, since the PNA and a protein (amino acid) can be bonded through a peptide bond, a double-stranded nucleic acid complex of some embodiments having a functional moiety comprising a protein or the like can be easily prepared. Furthermore, since the PNA of the double-stranded nucleic acid illustrated in FIGS. 4A-B has a shorter strand length than that of the RNA of the double-stranded nucleic acid of some embodiments illustrated in the lower part of FIGS. 3A-B, and there is no need to match the PNA to the base sequence of the target gene, mass production can be achieved. Generally, since synthesis of a PNA is a cost-consuming process, the double-stranded nucleic acid illustrated in FIGS. 4A-B is a preferred embodiment from the viewpoint that a relatively inexpensive double-stranded nucleic acid can be provided. Particularly, since the double-stranded nucleic acid illustrated in the lower part of FIGS. 4A-B has not only a first functional moiety comprising a protein or the like, but also a second functional moiety, which may comprise a lipid or the like, the double-stranded nucleic acid complex can be delivered to a target site with higher specificity and higher efficiency.

Furthermore, in general, when a compound is enterally administered (peroral administration or the like), the compound is diffused in the body not through the blood vessels but through the lymphatic vessels. However, in order to reach the lymphatic vessels, the molecular weight of the compounds typically should be 11,000 Daltons to 17,000 Daltons or more. Furthermore, since an enterally administered compound is exposed to RNase A in the intestinal tube, it is typically preferable that a nucleic acid drug containing RNA have all the portions of RNA modified by 2'-O-methylation or the like. Therefore, the double-stranded nucleic acid illustrated in FIGS. 5A-B, which has a molecular weight of about 18,000 Daltons and has all the RNA parts 2'-O-methylated, can be suitably used for perenteral administration. Furthermore, the double-stranded nucleic acid illustrated in the lower part of FIGS. 5A-B has a DNA strand (third nucleic acid strand) and a hairpin loop nucleic acid (preferably, a nucleic acid comprising 4 to 9 bases) that links the DNA strand and a complementary strand comprising RNA (second nucleic acid strand).

Thus, some suitable exemplary embodiments of the double-stranded nucleic acid complex of some embodiments have been described, but the double-stranded nucleic acid of some embodiments is not intended to be limited to the exemplary embodiments described above. Furthermore, any person having ordinary skill in the art can produce the first nucleic acid strand, the second nucleic acid strand, and the third nucleic acid strand according to some embodiments by appropriately selecting a known method. For example, the nucleic acids according to some embodiments can be produced by designing the respective base sequences of the nucleic acids on the basis of the information of the base sequence of the targeted transcription product (or, in some cases, the base sequence of a targeted gene), synthesizing the nucleic acids by using a commercially available automated nucleic acid synthesizer (products of Applied Biosystems, Inc.; products of Beckman Coulter, Inc.; and the like), and subsequently purifying the resulting oligonucleotides by using a reverse phase column or the like. Nucleic acids produced in this manner are mixed in an appropriate buffer solution and denatured at about 90° C. to 98° C. for several minutes (for example, for 5 minutes), subsequently the nucleic acids are annealed at about 30° C. to 70° C. for about 1 to 8 hours, and thus the double-stranded nucleic acid complex of some embodiments can be produced. Furthermore, a double-stranded nucleic acid complex to which a functional moiety is bonded can be produced by using a nucleic acid species to which a functional moiety has been bonded in advance, and performing synthesis, purification and annealing as described above. Numerous methods for joining functional moieties to nucleic acids are well-known in the art.

Thus, suitable exemplary embodiments of the double-stranded nucleic acids of the present invention have been described, but as will be disclosed in the following Examples, the "second nucleic acid strand" according to some embodiments is excellent from the viewpoint that an antisense nucleic acid can be delivered to a target site with high efficiency, without causing a decrease in the antisense effect. Therefore, the double-stranded nucleic acids of some embodiments are not intended to be limited to the exemplary embodiments described above, and for example, an embodiment that includes the following antisense nucleic acid instead of the first nucleic acid strand described above, can also be provided:

A double-stranded nucleic acid complex having an activity of suppressing the expression of a target gene by means of the antisense effect, the double-stranded nucleic acid complex comprising (i) an antisense nucleic acid that is complementary to the transcription product of the target gene, wherein the nucleic acid does not comprise DNA, and (ii) a nucleic acid that is complementary to the foregoing nucleic acid (i).

That is, in certain embodiments, an antisense nucleic acid has a non-RNase H-dependent antisense effect. The "non-RNase H-dependent antisense effect" means an activity of suppressing the expression of a target gene that occurs as a result of inhibition of translation or a splicing function modifying effect such as exon skipping when a transcription product of the target gene (RNA sense strand) and a nucleic acid strand that is complementary to a partial sequence of the transcription product are hybridized (see the description of the upper part outside the area surrounded by dotted lines in FIG. 1).

The "nucleic acid that does not comprise DNA" means an antisense nucleic acid that does not comprise natural DNA and modified DNA, and an example thereof may be a PNA or a nucleic acid comprising morpholino nucleic acid. Furthermore, in regard to the "nucleic acid that does not comprise DNA," similarly to the first nucleic acid strand or the second nucleic acid strand, a portion or the entirety of the nucleic acid may be composed of modified nucleotides, from the viewpoint that the resistance to nucleases is high. Examples of such modification include those described above, and the same nucleic acid may be subjected to plural kinds of modifications in combination. Furthermore, preferred embodiments related to the number of modified nucleic acids and the position of modification can be characterized by measuring the antisense effect possessed by the double-stranded nucleic acid after modification, as in the case of the first nucleic acid strand described above.

It is not necessary that the base sequence of the "nucleic acid that does not comprise DNA" and the base sequence of a nucleic acid that is complementary to the nucleic acid or the base sequence of the transcription product of a target gene be perfectly complementary to each other, and the base sequences may have a complementarity of at least 70% or higher, preferably 80% or higher, and more preferably 90% or higher (for example, 95%, 96%, 97%, 98%, 99% or higher).

There are no particular limitations on the strand length of the "nucleic acid that does not comprise DNA," but the strand length is as described above in regard to the first nucleic acid, and is usually 8 to 35 bases, 10 to 35 bases, 12 to 25 bases, or 13 to 20 bases.

The "nucleic acid that is complementary to a nucleic acid that does not comprise DNA" according to some embodiments is the same as the second nucleic acid strand described above. Furthermore, in the case where the strand length of the nucleic acid that does not comprise DNA and the strand length of the nucleic acid that is complementary to the nucleic acid are different, this embodiment may also comprise a third nucleic acid strand. Furthermore, this embodiment may also have the functional moieties described above bonded to the "nucleic acid that is complementary to the nucleic acid that does not comprise DNA" and/or the third nucleic acid strand.

Composition for suppressing expression of target gene or level of targeted transcription product by means of antisense effect.

The double-stranded nucleic acid complex of some embodiments can be delivered to a target site with high specificity and high efficiency and can very effectively suppress the expression of a target gene or the level of a transcription product, as will be disclosed in the Examples described below. Therefore, some embodiments can provide a composition which contains the double-stranded nucleic acid complex of some embodiments as an active ingredient and is intended to suppress, e.g., the expression of a target gene by means of an antisense effect. Particularly, the double-stranded nucleic acid complex of some embodiments can give high efficacy even when administered at a low concentration, and by suppressing the distribution of the antisense nucleic acid in organs other than the delivery-targeted area, adverse side effects can be reduced. Therefore, some embodiments can also provide a pharmaceutical composition intended to treat and prevent diseases that are associated with, e.g., increased expression of a target gene, such as metabolic diseases, tumors, and infections. More concrete examples of target organs and diseases relating to each organ in the present invention are shown in Table 1.

TABLE 1

| Target Organs | Related Diseases |
| --- | --- |
| Heart | Arrhythmias, Diabetic cardiomyopathy, Dilated cardiomyopathies (DCMs), Heart failure (HF), Heart failure (HF), Hyperglycemia-induced myocardial apoptosis, Hypertension, Hypertrophic cardiomyopathy (HCM), Myocardial infarction, Myocardial ischaemia |
| Skeletal Muscle | Duchenne muscular dystrophy (DMD), Facioscapulohumeral muscular dystrophy (FSHD), Myotonic dystrophy type 1 (DM1), Myotonic dystrophy type 2 (DM2), Polymyositis |

TABLE 1-continued

| Target Organs | Related Diseases |
| --- | --- |
| Lung | Acinetobactor infection, Acute lung injury (ALI), influenza A virus, Lung adenocarcinoma, non-small cell lung cancer (NSCLC), Pulmonary fibrosis |
| Adrenal grand | Adrenocortical carcinoma (ACC), Congenital adrenal hyperplasia (CAH), Macronodular Adrenal Hyperplasia (MAH), Nephrotic syndrome, Pheochromocytoma |
| Kidney | Chronic kidney disease (CKD), Diabetes, Renal cell carcinoma (RCC), Toxic acute tubular injury |
| Choroid plexus, Brain Capillary endotherial cells | Alzheimer disease, Amyotrophic lateral sclerosis (ALS), Brain tumor, Cerebral ischemia, Multiple sclerosis, Parkinson disease, Spinal muscular atrophy (SMA) |
| DRG | Neurogenic pain, Paraneoplastic neurological syndrome, Sjogren syndrome |

The composition containing the double-stranded nucleic acid complex of some embodiments can be formulated by known pharmaceutical methods. For example, the composition can be used enterally (perorally or the like) in the form of capsules, tablets, pills, liquids, powders, granules, fine granules, film-coating agents, pellets, troches, sublingual agents, peptizers, buccal preparations, pastes, syrups, suspensions, elixirs, emulsions, coating agents, ointments, plasters, cataplasms, transdermal preparations, lotions, inhalers, aerosols, injections and suppositories, or non-enterally.

In regard to the formulation of these preparations, pharmacologically acceptable carriers or carriers acceptable as food and drink, specifically sterilized water, physiological saline, vegetable oils, solvents, bases, emulsifiers, suspending agents, surfactants, pH adjusting agents, stabilizers, flavors, fragrances, excipients, vehicles, antiseptics, binders, diluents, isotonizing agents, soothing agents, extending agents, disintegrants, buffering agents, coating agents, lubricating agents, colorants, sweetening agents, thickening agents, corrigents, dissolution aids, and other additives can be appropriately incorporated.

On the occasion of formulation, as disclosed in Non-Patent Document 1, the double-stranded nucleic acid complex of some embodiments to which a lipid is bound as a functional moiety may be caused to form a complex with a lipoprotein, such as chylomicron or chylomicron remnant. Furthermore, from the viewpoint of increasing the efficiency of enteral administration, complexes (mixed micelles and emulsions) with substances having a colonic mucosal epithelial permeability enhancing action (for example, medium-chain fatty acids, long-chain unsaturated fatty acids, or derivatives thereof (salts, ester forms or ether forms)) and surfactants (nonionic surfactants and anionic surfactants) may also be used, in addition to the lipoproteins.

There are no particular limitations on the preferred form of administration of the composition of some embodiments, and examples thereof include enteral (peroral or the like) or non-enteral administration, more specifically, intravenous administration, intraarterial administration, intraperitoneal administration, subcutaneous administration, intracutaneous administration, tracheobronchial administration, rectal administration, and intramuscular administration, and administration by transfusion.

The composition of some embodiments can be used for animals including human beings as subjects. However, there are no particular limitations on the animals excluding human beings, and various domestic animals, domestic fowls, pets, experimental animals and the like can be the subjects of some embodiments.

When the composition of some embodiments is administered or ingested, the amount of administration or the amount of ingestion may be appropriately selected in accordance with the age, body weight, symptoms and health condition of the subject, type of the composition (pharmaceutical product, food and drink, or the like), and the like. However, the effective amount of ingestion of the composition according to the certain embodiments is 0.001 mg/kg/day to 500 mg/kg/day of the double stranded nucleic acid complex.

The double-stranded nucleic acid complex of some embodiments can be delivered to a target site with high specificity and high efficiency, and can suppress the expression of a target gene or the level of a transcription product very effectively, as will be disclosed in the Examples that follow. Therefore, some embodiments can provide a method of administering the double-stranded nucleic acid complex of some embodiments to a subject, and suppressing the expression of a target gene or transcription product level by means of an antisense effect. Furthermore, a method of treating or preventing various diseases that are associated with, e.g., increased expression of target genes, by administering the composition of some embodiments to a subject can also be provided.

As described above, the present invention makes it possible to reduce the level of a transcription product in a cell by contacting with the cell the composition of the present invention. Thus, the present invention also makes it possible to provide a method of reducing the level of a transcription product in a cell comprising contacting with the cell a composition comprising:
a double-stranded nucleic acid complex comprising a first nucleic acid strand annealed to a second nucleic acid strand, wherein:
(i) the first nucleic acid strand hybridizes to the transcription product and comprises (a) a region consisting of at least 4 consecutive nucleotides that are recognized by RNase H when the strand is hybridized to the transcription product, (b) one or more nucleotide analogs located on 5' terminal side of the region, (c) one or more nucleotide analogs located on 3' terminal side of the region and (d) a total number of nucleotides and nucleotide analogs ranging from 8 to 35 nucleotides and
(ii) the second nucleic acid strand comprises (a) nucleotides and optionally nucleotide analogs and (b) at least 4 consecutive RNA nucleotides.

EXAMPLES

Hereinafter, some embodiments will be described more specifically by way of Examples and Comparative Examples, but the embodiments not intended to be limited to the following Examples. Meanwhile, the mice supplied to the experiments described below were 4 to 6-week old female ICR mice with body weights of 20 to 25 g. Unless particularly stated otherwise, the experiments using mice were all carried out with n=3 to 4. Furthermore, the BNA used in the present Examples was a LNA represented by the above formula (1). In addition, Sequences described in Comparative Example 1 and Examples 1-15 are presented in Tables 2-4.

TABLE 2

| SEQ ID SEQUENCE | SYMBOL | Strand | Ex. |
|---|---|---|---|
| SEQ ID NO: 1<br>5'-$G_sC_sa_st_st_sg_sg_st_sa_st_sT_sC$-3' | Up: LNA;<br>lo: DNA;<br>S: phosphorothioate | AS/12 | CE1: has two forms,<br>5' Cy3 and 5' Cy3/3' Chol;<br>1 (plain); 2; 3; 7 (plain);<br>8 (plain); 9 (plain) |
| SEQ ID NO: 2<br>5'-GAAUACCAAUGC-3' | Up: RNA; | c/12 | 1: (o) 2 |
| SEQ ID NO: 3<br>5'-$g_sa_sAUACCAAU_sg_sc$-3' | Up: RNA;<br>lo: OMe-RNA;<br>S: phosphorothioate | c/12 | 1: (G); 2;<br>3 (has two forms,<br>plain and 5' Toc); 7 |
| SEQ ID NO: 4<br>5'-$g_sa_sa_su_sa_sc_sc_sa_sa_su_sg_sc$-3' | Up: RNA;<br>lo: OMe-RNA;<br>S: phosphorothioate | c/12 | 1: (m/s)<br>2 |
| SEQ ID NO: 5<br>5'-$G_sC_sa_st_st_sg_sg_st_sa_st_sT_sC_sA$-3' | Up: LNA;<br>lo: DNA;<br>S: phosphorothioate | AS/13 | 3; 4; 5; 6; 10 |
| SEQ ID NO: 6<br>5'-$A_sG_sC_sa_st_st_sg_sg_st_sa_st_sT_sC_sA$-3' | Up: LNA;<br>lo: DNA;<br>S: phosphorothioate | AS/14 | 3 |
| SEQ ID NO: 7<br>5'-$u_sg_sa_sAUACCAAU_sg_sc$-3' | Up: RNA;<br>lo: OMe-RNA;<br>S: phosphorothioate | c/13 | 3 (has two forms, plain and 5' Toc)<br>4 (5' Toc form only);<br>5 (5' Toc form only)<br>6 (plain and 5' Toc);<br>10 (5' Toc form only)<br>11 (5' Toc form only);<br>15 (5' Toc form only) |
| SEQ ID NO: 8<br>5'-$u_sg_sa_sAUACCAAU_sg_sc_su$-3' | Up: RNA;<br>lo: OMe-RNA;<br>S: phosphorothioate | c/14 | 3(has two forms, plain and 5' Toc) |

TABLE 3

| SEQ ID | SEQUENCE | SYMBOL | Strand | Ex. |
|---|---|---|---|---|
| SEQ ID NO: 9 | 5'-g$_s$a$_s$auaccaau$_s$g$_s$c-3' | Up: RNA; lo: OMe-RNA; S: phosphorothioate | c/12 | 7 (cRNA(G)-OM) |
| SEQ ID NO: 10 | 5'-u$_s$u$_s$cGCACCAGAAUACCAAu$_s$g$_s$c-3' | Up: RNA; lo: OMe-RNA; S: phosphorothioate | c/21 | 8 |
| SEQ ID NO: 11 | N'-<u>TGGTGCGAA</u>-C' | Und: PNA | 3$^{rd}$/9 | 8 |
| SEQ ID NO: 12 | N'-<u>GAAUACCAAUGC</u>-C' | Und: PNA | c/12 | 9 |
| SEQ ID NO: 13 | N'-<u>GAAUACCAAU</u>-C' | Und: PNA | c/10 | 9 |
| SEQ ID NO: 14 | N'-<u>GAAUACCA</u>-C' | Und: PNA | c/8 | 9 |
| SEQ ID NO: 15 | 5'-u$_s$g$_s$a$_s$AUACCAAU$_s$g$_s$c-3' | Up: RNA; lo: LNA; S: phosphorothioate | c/13 | 10 |
| SEQ ID NO: 16 | 5'-u$_s$g$_s$a$_s$A$_s$U$_s$A$_s$C$_s$C$_s$A$_s$A$_s$U$_s$g$_s$c-3' | Up: RNA; lo: LNA; S: phosphorothioate | c/13 | 10 |
| SEQ ID NO: 17 | 5'-u$_s$g$_s$a$_s$A$_s$U$_s$A$_s$C$_s$C$_s$A$_s$A$_s$U$_s$g$_s$c-3' | Up: RNA; lo: OMe-RNA; S: phosphorothioate | c/13 | 10 |
| SEQ ID NO: 18 | 5'-u$_s$g$_s$a$_s$AUACCAAUgcuacgcauacgcacca$_s$c$_s$c$_s$a-3' | Up: RNA; lo: OMe-RNA; S: phosphorothioate | c/31 | 11 |

TABLE 4

| SEQ ID | SEQUENCE | SYMBOL | Strand | Ex. |
|---|---|---|---|---|
| SEQ ID NO: 19 | 5'-T$_s$G$_s$t$_s$c$_s$t$_s$c$_s$t$_s$g$_s$c$_s$c$_s$T$_s$G$_s$G-3' | Up: LNA: lo: DNA: S: phosphorothioate | AS/13 | 12 |
| SEQ ID NO: 20 | 5'-c$_s$c$_s$a$_s$GGCAGAGA$_s$c$_s$a-3' | Up: RNA; lo: OMe-RNA; S: phosphorothioate | c/13 | 12 |
| SEQ ID NO: 21 | 5'-T$_s$T$_s$A$_s$T$_s$t$_s$g$_s$t$_s$c$_s$t$_s$c$_s$t$_s$g$_s$c$_s$c$_s$t$_s$G$_s$G$_s$A$_s$C$_s$T-3' | Up: LNA; lo: DNA; S: phosphorothioate | AS/20 | 12 |
| SEQ ID NO: 22 | 5'-a$_s$g$_s$u$_s$c$_s$c$_s$AGGCAGAGAC$_s$a$_s$a$_s$u$_s$a$_s$a-3' | Up: RNA; lo: OMe-RNA; S: phosphorothioate | c/20 | 12 |
| SEQ ID NO: 23 | 5'-T$_s$A$_s$g$_s$t$_s$c$_s$c$_s$a$_s$g$_s$t$_s$t$_s$C$_s$A$_s$C-3' | Up: LNA: lo: DNA; S: phosphorothioate | AS/13 | 13 |
| SEQ ID NO: 24 | 5'-g$_s$u$_s$g$_s$AACUGGACuauacgcac$_s$c$_s$a-3' | Up: RNA; lo: OMe-RNA; S: phosphorothioate | c/22 | 13 |
| SEQ ID NOs: 25 and 31 | N'-SPGARAFGGGGS-tggtgcgta-C' | Up: AA; Und, lo: PNA | 3$^{rd}$/9 | 13 |
| SEQ ID NO: 26 | 5'-C$_s$C$_s$A$_s$t$_s$t$_s$g$_s$t$_s$c$_s$a$_s$c$_s$a$_s$c$_s$T$_s$C$_s$C-3' | Up: LNA; lo: DNA; S: phosphorothioate | AS/15 | 14 |
| SEQ ID NO: 27 | 5'-g$_s$g$_s$a$_s$GUGUGACCA$_s$u$_s$g$_s$g-3' | Up: RNA; lo: OMe-RNA; S: phosphorothioate | c/15 | 14 (5' Toc) |
| SEQ ID NO: 28 | 5-G$_s$C$_s$a$_s$t$_s$t$_s$g$_s$g$_s$t$_s$a$_s$t$_s$T$_s$C$_s$A-3' | Up: N-methyl amideBNA; lo: DNA, S: phosphorothioate | AS/13 | 15 |

TABLE 4-continued

| SEQ ID | SEQUENCE | SYMBOL | Strand | Ex. |
|---|---|---|---|---|
| SEQ ID NO: 29 | 5'-T$_s$C$_s$C$_s$A$_s$G$_s$c$_s$a$_s$t$_s$t$_s$g$_s$g$_s$t$_s$a$_s$t$_s$t$_s$C$_s$A$_s$G$_s$T$_s$G-3' | Up: LNA; lo: DNA; S: phosphorothioate | AS/20 | CE1 (3'-Chol) |
| SEQ ID NO: 30 | 5'-T$_s$C$_s$C$_s$A$_s$G$_s$c$_s$a$_s$t$_s$t$_s$g$_s$g$_s$t$_s$a$_s$t$_s$t$_s$c$_s$a$_s$g$_s$t$_s$g$_s$t$_s$g$_s$a$_s$t$_s$G$_s$A$_s$C$_s$A$_s$C-3' | Up: LNA; lo: DNA; S: phosphorothioate | AS/29 | CE1 (3'-Chol) |

Comparative Example 1

The stability of an antisense oligonucleotide (ASO) in an antisense method, the activity of suppressing the expression of a target gene in vivo (antisense effect), and the delivery properties and antisense effect in vivo were evaluated for an ASO comprising LNA nucleotides and DNA nucleotides ("LNA/DNA gapmer") to which cholesterol had been directly bound so as to enhance the delivery properties.

Figure 6A:
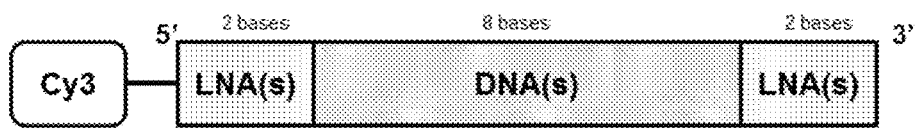
FIG. 6A is a schematic diagram illustrating a nucleic acid having the structure of 5'-LNA-DNA-LNA-3' that is labeled at the 5' terminus with the fluorescent dye Cy3.
Figure 6B:
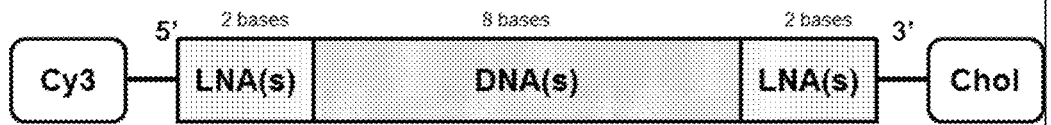
FIG. 6B is a schematic diagram illustrating a nucleic acid having the structure of 5'-LNA-DNA-LNA-3' that is labeled at the 5' terminus with the fluorescent dye Cy3 and is labeled at the 3'-terminus with cholesterol ("Chol").
"(s)" represents a phosphorothioated nucleic acid.

Two ASO's, having the LNA/DNA gapmer structures schematically illustrated in FIGS. 6A-B, were prepared. Cy3-ASO, in which a fluorescent dye Cy3 was covalently bonded to the 5'-terminus of an LNA/DNA gapmer ASO (FIG. 6A), and Cy3-Chol-ASO, in which cholesterol was covalently bonded to the 3'-terminus of the Cy3-ASO (FIG. 6B), were prepared. The target gene of these ASO's is apolipoprotein B (ApoB) gene, and its sequence is shown below. These ASO's were produced by commissioning Gene Design, Inc. with the synthesis.

(SEQ ID NO: 1)
GCattggtatTC (upper case: LNA, lower case: DNA, between nucleic acids: phosphorothioate bond)

Meanwhile, Cy3 and the ASO were bonded to each other by a phosphorothioate bond according to a known technique, and cholesterol and the ASO were bonded to each other through tetraethylene glycol linker.

These ASO's were respectively intravenously injected in an amount of 10 mg/kg through the mouse tail vein, and after one hour, the mice were dissected to extract the livers. The livers thus obtained were fixed with a 4% formalin solution, subsequently the solution was replaced with a 30% sucrose solution, the livers were embedded in OCT Compound, and then sections having a thickness of 10 μm were produced therefrom. Subsequently, the sections were nucleus stained by using DAPI, and then the signal intensities of Cy3 in the sections were observed using a confocal microscope. The results thus obtained are presented in FIGS. 7A-B.

Furthermore, Cy3-ASO and Cy3-Chol-ASO were intravenously injected to three mice each through the tail vein, and after three days, the second administration of ASO was carried out. The amount of ASO administered was set to 10 mg/kg. Furthermore, mice of a negative control group were also prepared by administering PBS only instead of the ASO. The day after the second administration, the mice were perfused with PBS, and then the mice were dissected to extract the livers. 1 ml of a nucleic acid extracting reagent (Isogen, manufactured by Gene Design, Inc.) was added to 80 mg of the liver thus extracted, and mRNA was extracted according to the protocol attached to the reagent. Subsequently, the concentrations of mRNA of these mice were measured, and cDNA was synthesized from a certain amount of mRNA by using SuperScript III (manufactured by Invitrogen, Inc.) according to the protocol attached thereto.

The cDNA thus produced was used as a template, and quantitative RT-PCR was carried out using a TaqMan System (manufactured by Roche Applied Bioscience Corp.). Meanwhile, the primers used in the quantitative RT-PCR were products designed and produced by Life Technologies Corp. based on the various gene numbers. Furthermore, the conditions for temperature and time were as follows: 15 seconds at 95° C., 30 seconds at 60° C., and 1 second at 72° C. were designated as one cycle, and 40 cycles thereof were carried out. Based on the results of the quantitative RT-PCR thus obtained, the amount of expression of mApoB/amount of expression of mGAPDH (internal standard gene) were respectively calculated, and the calculation results for the negative control group and the calculation results for the ASO-administered groups were compared and evaluated by a t-test. The results thus obtained are presented in FIG. 8.

As is obvious from the results presented in FIGS. 7A-B, the LNA/DNA gapmer to which cholesterol had been directly bound was accumulated in the liver in a much larger amount than the LNA/DNA gapmer without cholesterol bound thereto.

Figure 8:
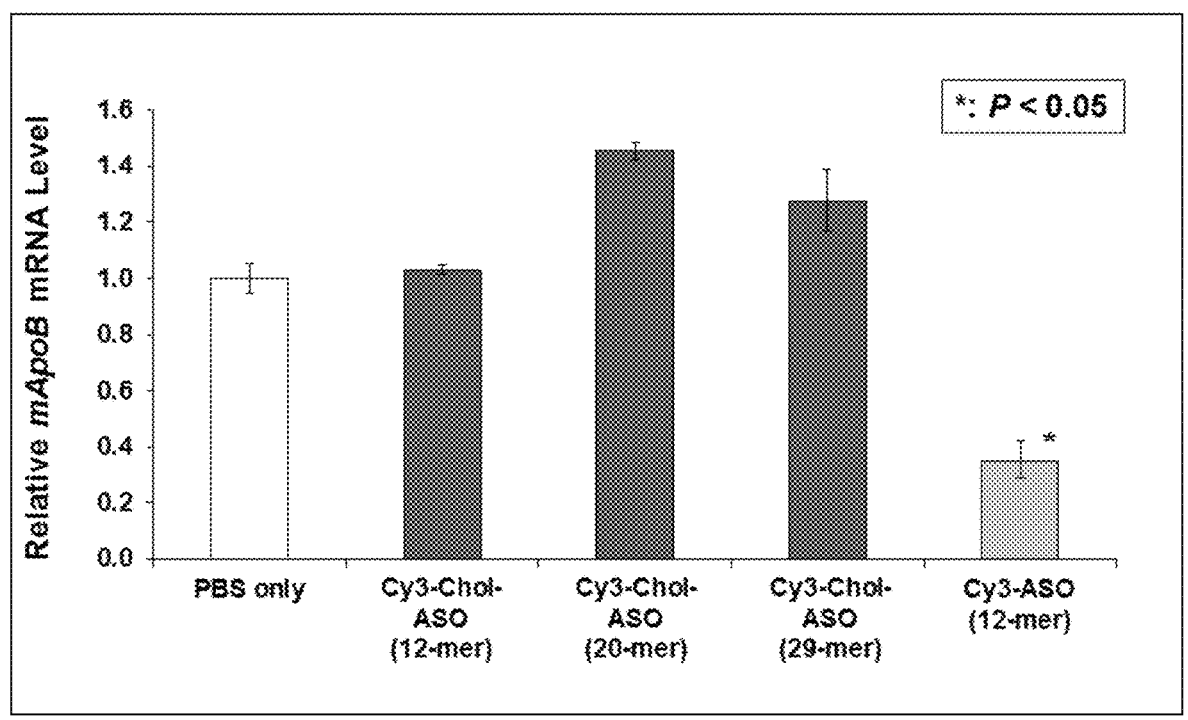
FIG. 8 is a graph illustrating the results obtained by administering to mice "12-mer Cy3-Chol-LNA(ApoB1)" (in accordance with FIG. 6B), "20-mer Cy3-Chol-LNA (ApoB1)," or "29-mer Cy3-Chol-LNA(ApoB1)," or "12-mer Cy3-LNA(ApoB1)" (in accordance with FIG. 6A), all of which have a sequence complementary to the base sequence of ApoB1 gene, and analyzing the amount of expression of ApoB1 gene in the livers of these mice by quantitative PCR.

However, as presented in FIG. 8, it was found that when cholesterol is directly bound to the LNA/DNA gapmer and used, the antisense effect was lost.

Example 1

Figure 9:
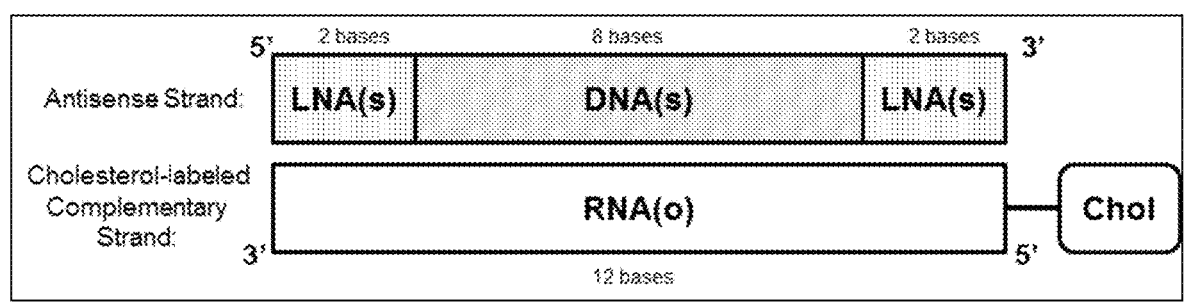
FIG. 9 is a schematic diagram illustrating certain embodiments of a double-stranded nucleic acid. Symbols have the same meanings as those defined in FIGS. 3A-6B.

Since it was found that the antisense effect is impaired when a functional moiety such as cholesterol is directly bound to the LNA/DNA gapmer (antisense strand), the inventors conceived of using a double-stranded nucleic acid complex where the complementary strand to the ASO carries a functional moiety to direct delivery of the ASO. FIG. 9 schematically illustrates one embodiment of such a complex.

For example, in the case of using an RNA strand as the complementary strand to an antisense LNA/DNA gapmer (ASO comprising a LNA and a DNA) and further binding a functional moiety to the RNA, the complex of the ASO and the complementary RNA strand (cRNA) is specifically and efficiently delivered to the target site by the functional moiety bonded to the cRNA. Further, when the complex is delivered into the nucleus of the cell at the target site, since the cRNA is itself an RNA-DNA hetero-oligonucleotide, it is believed that the cRNA is cleaved by RNase H present in the nucleus, thereby exposing the ASO as a single strand. Subsequently, this ASO binds to mRNA of the target gene and forms a new RNA-DNA heteroduplex, wherein the mRNA is decomposed by RNase H to achieve an antisense effect.

That is, the inventors conceived that by conducting cleavage of a cRNA having a functional moiety bonded thereto and decomposition of mRNA of a target gene by using RNase H, a LNA/DNA gapmer (ASO comprising a LNA and a DNA) can be delivered to a target site with high specificity and high efficiency, and the expression of the target gene can be very effectively suppressed without the antisense effect of the ASO being inhibited by the functional moiety.

Then, in order to demonstrate such conception, the inventors first produced a double-stranded DNA of a LNA/DNA gapmer and a cRNA by the method described below, and evaluated the properties.

Figure 10:
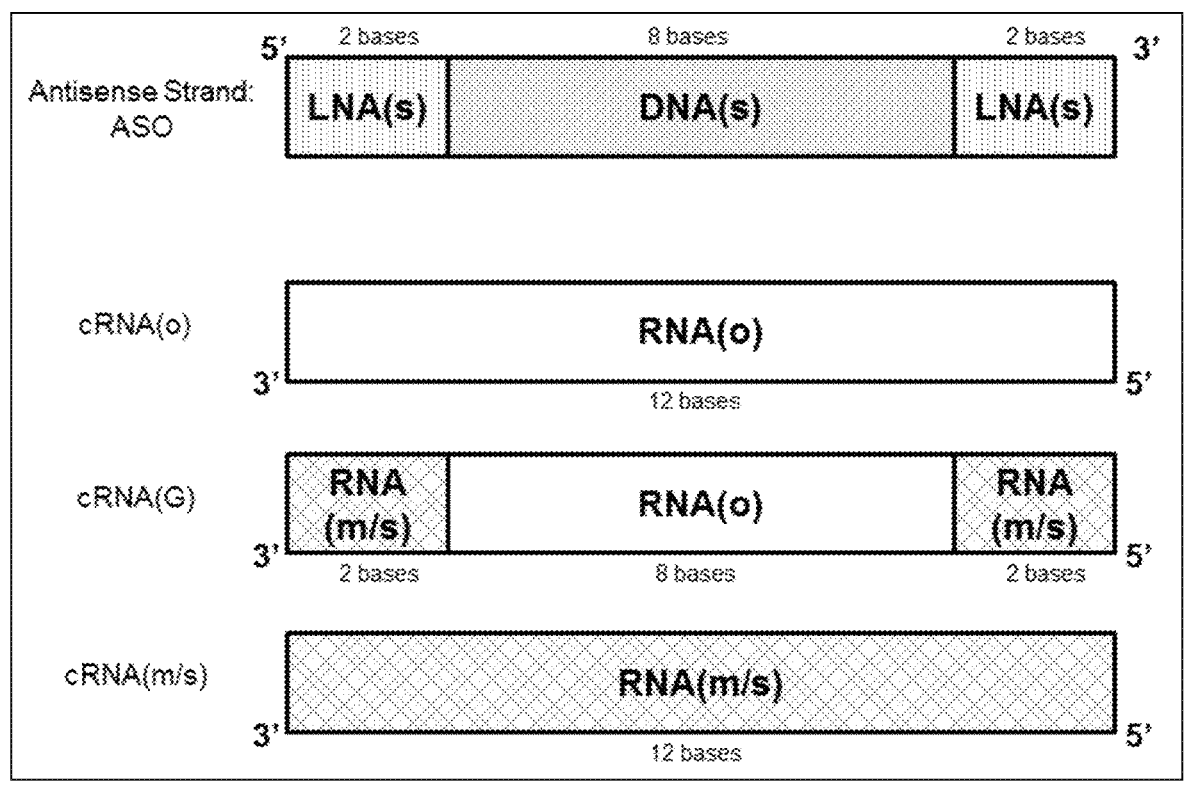
FIG. 10 is a schematic diagram illustrating the antisense strand (ASO) and its complementary strands (cRNA(o), cRNA(G), and cRNA(m/s)), which were used to evaluate the antisense effect of a double-stranded nucleic acid complex according to one embodiment. Symbols have the same meanings as those defined in FIGS. 3A-6B and 9.

As the LNA/DNA gapmer, a Cy3-ASO produced in the same manner as in Comparative Example 1 was used. Also, as the cRNA, three different complementary strand structures were prepared. The three structures are schematically illustrated in FIG. 10. One structure comprises conventional RNA (natural RNA) only (cRNA(o)), in a second structure, two bases each at end of the cRNA strand were chemically modified (2'-O-methylated and phosphorothioated) to have RNase resistance (cRNA(G)), and in the third structure, all the bases in the cRNA strand were chemically modified (2'-O-methylated and phosphorothioated) to be resistant to cleavage by RNase (cRNA(m/s)). The probes were produced on commission by Hokkaido System Science Co., Ltd. The sequences of the cRNA strands were as follows:

cRNA(o):
(SEQ ID NO: 2)
5'-GAAUACCAAUGC-3' cRNA(G):
(SEQ ID NO: 3)
5'-$g_s a_s$AUACCAAU$_s g_s$c-3' cRNA(m/s):
(SEQ ID NO: 4)
5'-$g_s a_s a_s u_s a_s c_s c_s a_s a_s u_s g_s$c-3'
(Upper case: RNA, lower case: 2'-OMe-RNA, s: phosphorothioate bonds between the nucleic acids)

The LNA/DNA gapmer and the respective cRNA's were mixed in equimolar amounts, and the mixtures were heated at 95° C. for 5 minutes and then were kept warm at 37° C. for one hour to thereby anneal these nucleic acid strand and form double-stranded nucleic acid complexes. The annealed nucleic acids were stored at 4° C. or on ice.

Subsequently, the Cy3-ASO's that had been annealed with the respective cRNA's, and Cy3-ASO were applied to 15% acrylamide gel in an amount of 100 pmol each in terms of the amount of LNA, and electrophoresis was carried out at 100 V for one hour. After the electrophoresis, a photograph of the gel was taken directly, and then a photograph was taken under UV light. The results thus obtained are presented in FIGS. 11A-B.

Furthermore, the Cy3-ASO's that had been annealed with the respective cRNA's, and the Cy3-ASO were treated with RNase H, subjected to electrophoresis as described above, and a photograph of the gel was taken under UV illumination. The results thus obtained are presented in FIG. 12.

Figure 11A:
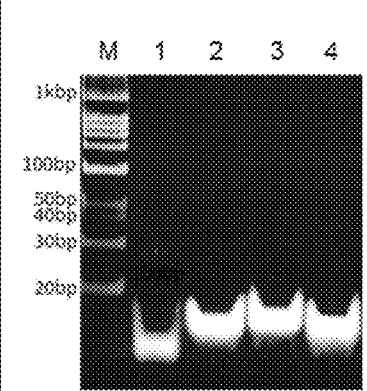
FIGS. 11A-B show photographs illustrating the results obtained by analyzing the presence or absence of annealing of the antisense strand and its complementary strands illustrated in FIG. 10 by electrophoresis. Panel A indicates the results of taking a photograph under UV illumination, and panel B shows a photograph of the gel.
Figure 11B:
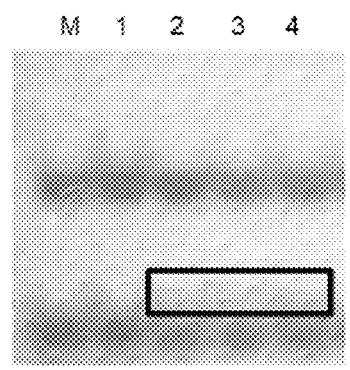

The results presented in FIGS. 11A-B demonstrate that the product obtained by annealing Cy3-ASO and cRNA(o) together, the product obtained by annealing Cy3-ASO and cRNA(G) together, and the product obtained by annealing Cy3-ASO and cRNA(m/s) together all had slower migration rates as compared with Cy3-ASO (Lane 1), which was a single-stranded ASO, confirming that the annealed products respectively formed double-stranded nucleic acids.

Furthermore, although not illustrated in the drawings, a complementary strand comprising DNA (cDNA) and Cy3-ASO were mixed and annealed as described above, and the product was analyzed by electrophoresis; however, the product had the same band height as that of Cy3-ASO. It was confirmed that cDNA and Cy3-ASO cannot form a double-stranded nucleic acid under the conditions employed. Meanwhile, the sequences and modifications of the cDNA's that were evaluated were the same as those of cRNA(o), cRNA (G) and cRNA(m/s), except that uracil was changed to thymine (hereinafter, the same).

Figure 12:
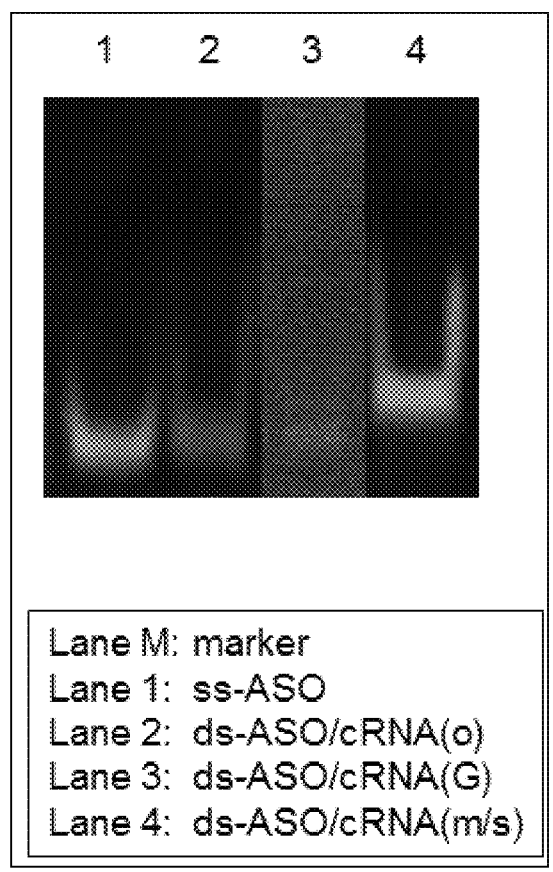
FIG. 12 is a photograph taken under UV illumination illustrating the results obtained by annealing the antisense strand and its complementary strands illustrated in FIG. 10, treating the strands with RNase H, and analyzing the reaction products by electrophoresis.

Also, as is obvious from the results illustrated in FIG. 12, even though a RNase H treatment was applied, the duplex of Cy3-ASO and cRNA(m/s) maintained the double-stranded nucleic acid structure. On the other hand, since treatment of the cRNA(o) and cRNA(G) duplexes yielded a product having the same migration rate as that of Cy3-ASO, it was confirmed that the complementary RNA strand of these duplexes was decomposed by RNase H and thus the single-stranded Cy3-ASO nucleic acids were released from the duplex and could migrate as a single strand.

Subsequently, in addition to the electrophoresis described above, the melting point (Tm) of a double-stranded nucleic acid composed of the LNA/DNA gapmer and cRNA was evaluated by the method described below.

Sample solutions (100 µL) in which the final concentrations were adjusted to 100 mM for sodium chloride, 10 mM for a sodium phosphate buffer solution (pH 7.2), and 2 µM for the respective oligonucleotide strands were placed in a boiling water bath, and the sample solutions were cooled to room temperature over 12 hours and were left to stand for 2 hours at 4° C. Under a nitrogen gas stream, the sample solutions were cooled to 5° C., and after the samples were maintained at 5° C. for 15 minutes, the analysis was commenced. For the melting point analysis, the temperature was increased to 90° C. at a rate of 0.5° C./min, and the absorbance at 260 nm was plotted at an interval of 0.5° C. The Tm values were calculated by a differential method. The measurement was carried out by using Shimadzu UV-1650PC spectrophotometer. The results thus obtained are presented in Table 5.

TABLE 5

| Nucleic Acid | Modification | Tm(° C.) |
|---|---|---|
| cRNA | o | 45.32 |
|  | G | 47.65 |
|  | m/s | 41.17 |
| cDNA | o | 37.51 |
|  | G | 34.33 |
|  | m/s | 26.45 |

As shown by the results presented in Table 5, the melting temperature (Tm) of duplexes formed between the LNA/DNA gapmer and the cDNA strands was lower than the body temperature in all cases. On the contrary, the melting temperature (Tm) of the duplex of LNA/DNA gapmer and cRNA was maintained in the range of 40° C. in all cases, and thus it was found that the relevant double-stranded nucleic acids do not undergo dissociation at room temperature or the body temperature.

Example 2

A complementary strand comprising conventional RNA only (cRNA(o))(SEQ ID NO: 2); a complementary strand in which all the RNA's were subjected to 2'-OMe (2'-O-methylation) modification and phosphorothioate binding (S-conversion) between the nucleic acids (cRNA(m/s))(SEQ ID NO: 4); and a complementary strand in which only the two terminal RNA bases were subjected to 2'-OMe modification and S-conversion between the nucleic acids, and the 8 bases at the center were conventional RNA's (cRNA(G)) (SEQ ID NO: 3) were provided in the same manner as in Example 1. These complementary strands were all annealed with the LNA/DNA gapmer (SEQ ID NO: 1), and thus double-stranded nucleic acids were produced. The target gene of the LNA/DNA gapmer was the rat apolipoprotein B (rApoB) gene. The ASO was produced by commissioning Gene Design, Inc. with the synthesis.

The LNA/DNA gapmer was transfected alone and as part of a double-stranded complex with each of the cRNA strands described above to rat liver cell culture systems (McA-RH7777), by using Lipofectamine 2000 (manufactured by Invitrogen, Inc.) according to the usage protocol provided with the reagent. The concentration of the gapmer that was added to the medium at the time of the transfection was set to 0.4 nM or 10 nM. Furthermore, controls in which no nucleic acid strands were added to cells were also prepared. Subsequently, 24 hours after the transfection, the cells were collected by using Isogen, and mRNA's were collected according to the manufacturer's usage protocol.

The concentrations of these mRNA's were measured, and cDNA's were synthesized from certain amounts of the mRNA's by using SuperScript III according to the manufacturer's protocol. Subsequently, the cDNA's thus produced were used as templates, and quantitative RT-PCR was carried out by using a TaqMan system. Meanwhile, for the primers used in the quantitative RT-PCR, those designed and produced by Life Technologies Corp. based on the various gene numbers. Furthermore, the conditions for temperature and time were as follows: 15 seconds at 95° C., 30 seconds at 60° C., and 1 second at 72° C. were designated as one cycle, and 40 cycles thereof were carried out. Based on the results of the quantitative RT-PCR thus obtained, the amount of expression of rApoB/amount of expression of rGAPDH (internal standard gene) were respectively calculated, and the calculation results for the control group and the calculation results for the nucleic acid-administered groups were compared and evaluated by a t-test. The results thus obtained are presented in FIG. 13. In addition, for the transfections made with 10 nM concentration, the results for the double-stranded nucleic acid complexes were normalized to the results for the LNA/DNA gapmer (ASO) alone and evaluated by the t-test. The results thus obtained are presented in FIG. 14.

Figure 13:
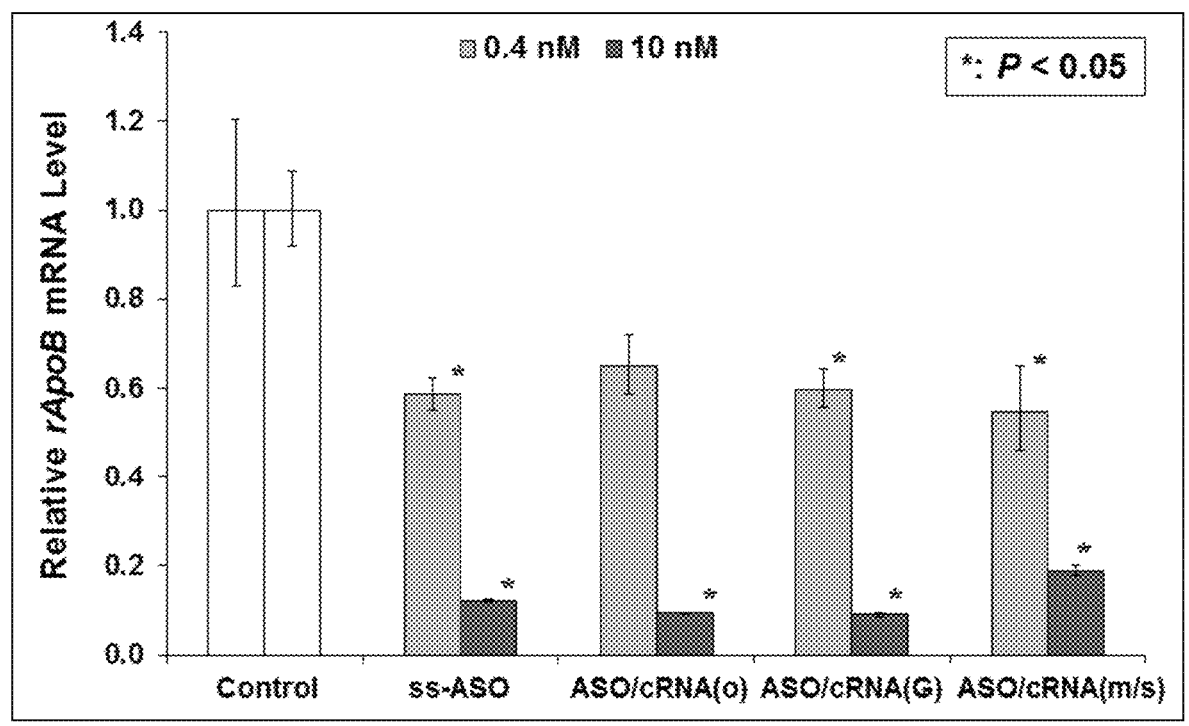
FIG. 13 is a graph illustrating the results obtained by introducing the antisense strand illustrated in FIG. 10 or double-stranded nucleic acid complexes (at concentrations of 0.4 nM or 10 nM) composed of the antisense strand and one of the complementary strands illustrated in FIG. 10, into cells. The amount of expression of ApoB1 gene, whose transcription product is targeted by the antisense strand, in the cells was analyzed by quantitative PCR.
Figure 14:
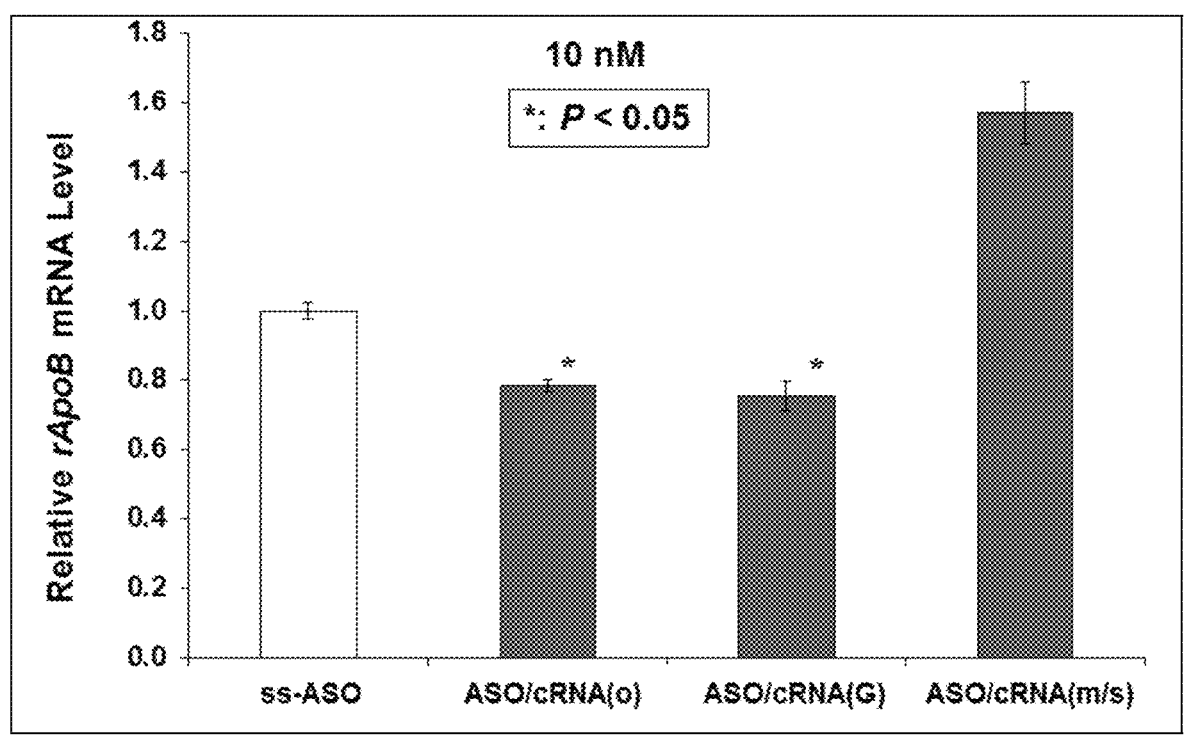
FIG. 14 is a graph illustrating the results obtained by analyzing the amount of expression of ApoB1 gene in cells into which the antisense strand illustrated in FIG. 10 or double-stranded nucleic acid complexes composed of the antisense strand and one of the complementary strands illustrated in FIG. 10, normalized to the amount of expression obtained in the cells where only the antisense strand was introduced.

As shown by the results presented in FIG. 13, the antisense effect of the double-stranded nucleic acid comprising the LNA/DNA gapmer and cRNA(o) (LNA/cRNA(o)) and the double-stranded nucleic acid comprising the LNA/DNA gapmer and cRNA(G) (LNA/cRNA(G)) is similar to that caused by the LNA/DNA gapmer (ss-ASO) when administered at the lower concentration of 0.4 nM. However, as shown in FIG. 14, when administered at the higher concentration of 10 nM, the results suggest that the double-stranded complexes in which the complementary strand is susceptible to cleavage (LNA/cRNA(o) and LNA/cRNA(G)) improve the antisense effect by about 20% compared to the gapmer ASO administered as a single strand.

Therefore, it was found that even if a LNA/DNA gapmer is annealed with a complementary strand comprising RNA to obtain a double-stranded nucleic acid complex, the target gene expression suppressing effect (antisense effect) in the cell was maintained. Furthermore, when a complementary RNA strand susceptible to RNase H was used, the antisense effect in the cell was further increased. Such an increase in the antisense effect is believed to be caused by the cleavage of the complementary strand RNA in the nucleus.

Example 3

Figure 15:
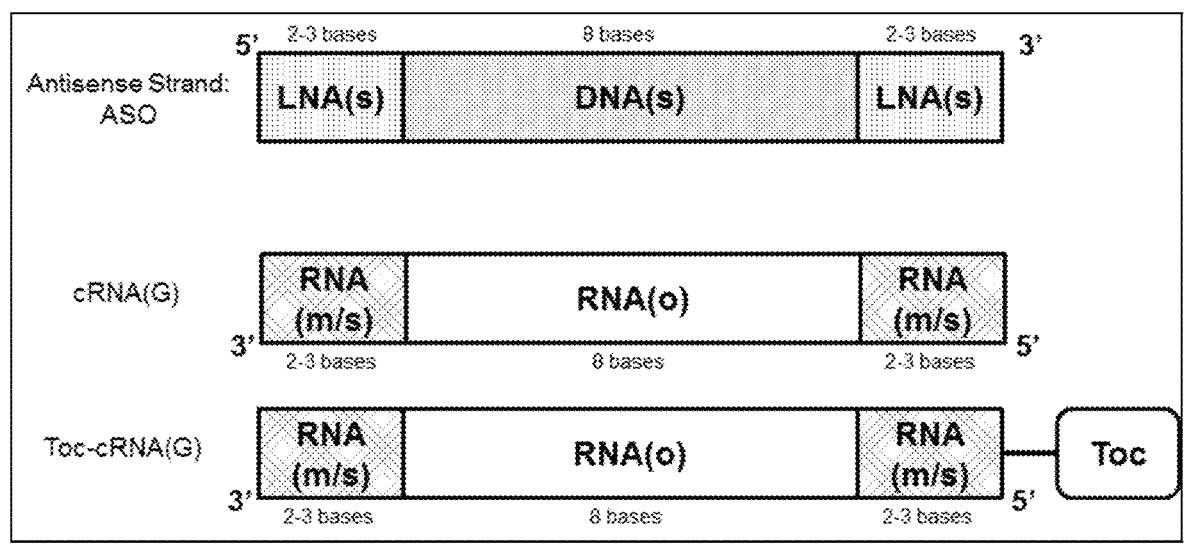
FIG. 15 is a schematic diagram illustrating an antisense strand, a complementary strand (cRNA(G)), and a complementary strand with a tocopherol functional moiety (Toc-cRNA(G)), which were used to evaluate the antisense effect of a double-stranded nucleic acid complex. "Toc" represents tocopherol. Other symbols have the same meanings as those defined in FIGS. 3A-6B, 9, and 10.

Next, as illustrated schematically in FIG. 15, a complementary RNA strand in which tocopherol (Toc) was bound to the 5'-terminus of the cRNA(G) (Toc-cRNA(G)) was produced, and this was annealed with the LNA/DNA gapmer (antisense strand). Thereby, indirect binding of tocopherol to an antisense strand was successfully achieved. The sequence, composition, and strand length of the LNA/DNA gapmers and the complementary strands (cRNA) used in the Examples were as follows.

```
Antisense LNA/DNA gapmer strands
1. ASO 12-mer:
                                    (SEQ ID NO: 1)
5'-GCattggtatTC-3'

2. ASO 13-mer:
                                    (SEQ ID NO: 5)
5'-GCattggtatTCA-3'

3. ASO 14-mer:
                                    (SEQ ID NO: 6)
5'-AGCattggtatTCA-3'
(Upper case: LNA, lower case: DNA, between
nucleic acids: phosphorothioate bond at all sites)

Complementary strands
1. cRNA 12-mer:
                                    (SEQ ID NO: 2)
5'-g_sa_sAUACCAAU_sg_sc-3'

2. cRNA 13-mer:
                                    (SEQ ID NO: 7)
5'-u_sg_sa_sAUACCAAU_sg_sc-3'

3. cRNA 14-mer:
                                    (SEQ ID NO: 8)
5'-u_sg_sa_sAUACCAAU_sg_sc_su-3'
(Upper case: RNA, lower case: 2'-OMe-RNA,
s: phosphorothioate bonds between the nucleic
acids)
```

The binding between tocopherol and the cRNA was carried out according to a known technique, by preparing tocopherol amidite in which the hydroxyl group at the 6-position of the chromane ring of tocopherol was joined to the phosphoramidite, and then the tocopherol amidite was coupled to the 5'-terminus of the RNA by standard coupling methods.

Next, the LNA/DNA gapmer (ss-ASO), the double-stranded nucleic acid complex comprising a LNA/DNA gapmer and cRNA(G) (LNA/cRNA(G)), and the double-stranded nucleic acid complex comprising a LNA/DNA gapmer and Toc-cRNA(G) (LNA/Toc-cRNA(G)), pairing in each complex strands that have the same strand length of 12 bases, 13 bases, or 14 bases, respectively, were intravenously injected to a mouse in an amount of 0.75 mg/kg each through the tail vein. Also, as a negative control group, mice to which only PBS was injected instead of the single-stranded ASO or double-stranded nucleic acid complex were also prepared. Seventy-two hours after the injection, the mice were perfused with PBS, and then the mice were dissected to extract the liver. Subsequently, extraction of mRNA, synthesis of cDNA, and quantitative RT-PCR were carried out by the same methods as the methods described in Comparative Example 1, the amount of expression of mApoB/amount of expression of mGAPDH (internal standard gene) was calculated, and comparisons were made between the group administered with PBS (PBS only) and the groups administered with a nucleic acid. The results thus obtained are presented in FIG. 16.

Figure 16:
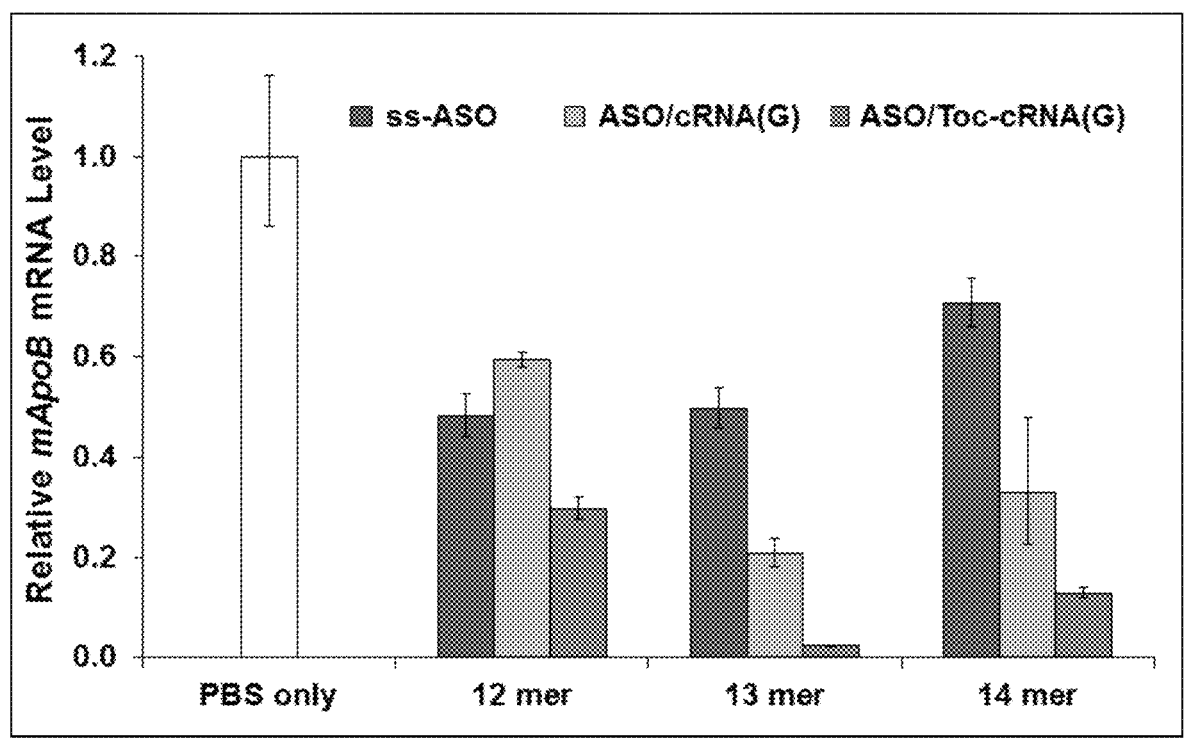
FIG. 16 is a graph illustrating the results obtained by administering the antisense strand illustrated in FIG. 15 or double-stranded nucleic acids composed of the antisense strand and one of the complementary strands illustrated in FIG. 15, to mice, and analyzing the amounts of expression of ApoB1 gene, whose transcription product is targeted by the antisense strand, in the mice.

As illustrated in FIG. 16, it was found that by binding tocopherol to a complementary strand, ASO/Toc-cRNA(G) is delivered to and accumulated in the liver with high specificity and high efficiency, and a marked antisense effect was exhibited as compared with ASO/cRNA(G). As shown, the effect exhibited by the ASO/Toc-cRNA having a strand length of 13 bases was particularly large.

Example 4

The specificity of ASO/Toc-cRNA complex for its target gene was evaluated by the same method as the method described in Example 3. That is, a double-stranded nucleic acid comprising a LNA/DNA gapmer having a strand length of 13 bases and the complementary strand Toc-cRNA(G) (ASO/Toc-cRNA(G)) was prepared, and intravenously injected to a mouse, and by using the liver-derived cDNA obtained from the mouse, the expression of the target gene (mApoB gene) in the liver and endogenous control genes (mTTR gene, mSOD1 gene, and mGAPDH gene) was evaluated by quantitative PCR. Meanwhile, regarding the primers used in the quantitative RT-PCR, primers designed and produced by Life Technologies Corp. based on the various gene numbers were used. The results thus obtained are presented in FIG. 17.

Figure 17:
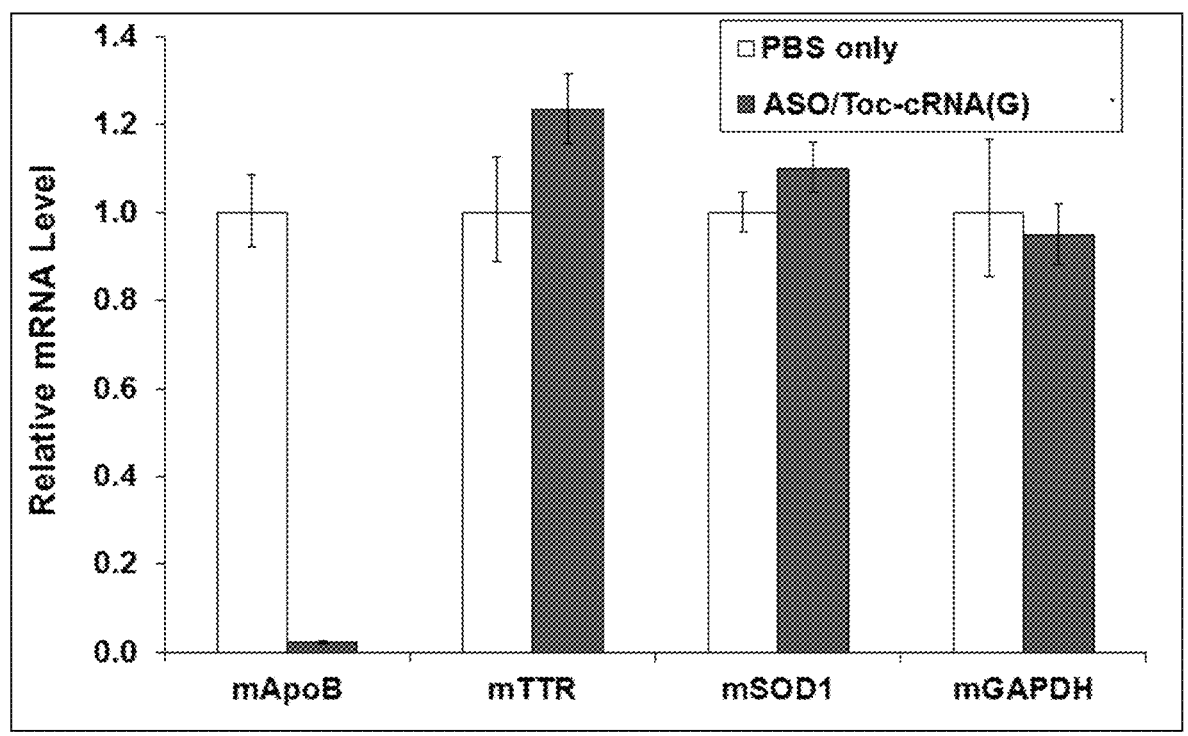
FIG. 17 is a graph illustrating the results obtained by evaluating the specificity of the antisense effect of a double-stranded nucleic acid complex composed of the antisense strand and a complementary strand having tocopherol bound thereto as illustrated in FIG. 15.

As shown by the results graphed in FIG. 17, in the liver of the mouse to which ASO/Toc-cRNA 13-mer was administered, a significant decrease in the expression was observed only in the mApoB gene, which was the gene transcription product targeted by the LNA/DNA gapmer (ASO). Therefore, it was found that the double-stranded nucleic acid complex comprising the LNA/DNA gapmer and Toc-cRNA (G) has a high specificity for the targeted gene.

Example 5

The dose-dependency of the antisense effect by ASO/Toc-cRNA(G) was evaluated by the same method as the method described in Example 3 using the 13-mer strands. That is, ASO/Toc-cRNA(G) 13-mer double-stranded complex was intravenously injected to mice in an amount of 0 mg/kg, 0.02 mg/kg, 0.05 mg/kg, 0.09 mg/kg or 0.75 mg/kg, and by using the liver-derived cDNA obtained from the mice, expression of mApoB gene was evaluated by quantitative PCR. The results thus obtained are presented in FIG. 18.

Figure 18:
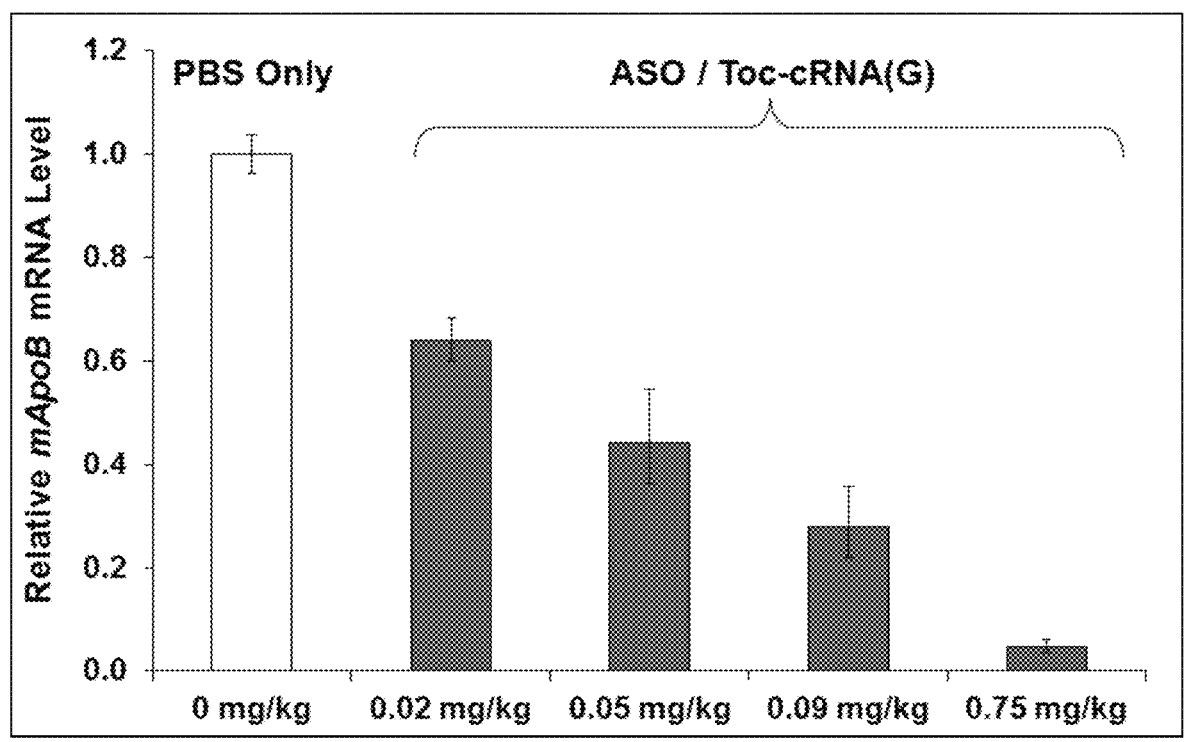
FIG. 18 is a graph illustrating the results obtained by evaluating the dose dependency of the antisense effect of a double-stranded nucleic acid complex composed of the antisense strand and a complementary strand having tocopherol bound thereto as illustrated in FIG. 15.

As shown by the results illustrated in FIG. 18, it was found that the antisense effect of ASO/Toc-cRNA(G) exhibited a dose-dependent effect. Also, it was found from these results that the amount of ASO/Toc-cRNA(G) required to suppress the expression of the target gene by half (ED50) was calculated to be about 0.036 mg/kg, which is a low concentration for achieving 50% suppression.

Example 6

The sustainability of the antisense effect by ASO/cRNA and ASO/Toc-cRNA was evaluated by the same method as the method described in Example 3. That is, a LNA/DNA gapmer (ss-ASO), the double-stranded nucleic acid comprising a LNA/DNA gapmer and cRNA-G (ASO/cRNA (G)), or the double-stranded nucleic acid comprising a LNA/DNA gapmer and Toc-cRNA (ASO/Toc-cRNA(G)) was intravenously injected into a mouse. The strand length of all the nucleic acid strands was 13 bases. Controls were also included in which just PBS solution and no nucleic acids were injected. In a first experiment, after the intravenous injection, liver was extracted after 1 day, after 3 days, after 7 days, after 14 days, and after 28 days, and by using the liver-derived cDNA, the expression of mApoB gene was evaluated by quantitative PCR. The results thus obtained are presented in FIG. 19A. The experiment was repeated using a PBS solution control, single-stranded LNA only, and the double-stranded complex ASO/Toc-cRNA(G), and resulting expression levels of mApoB was evaluated by the same method, after 1 day, 3 days, 7 days, 14 days, 28 days, and 42 days post-injection. The results obtained are presented in FIG. 19B.

Figure 19A:
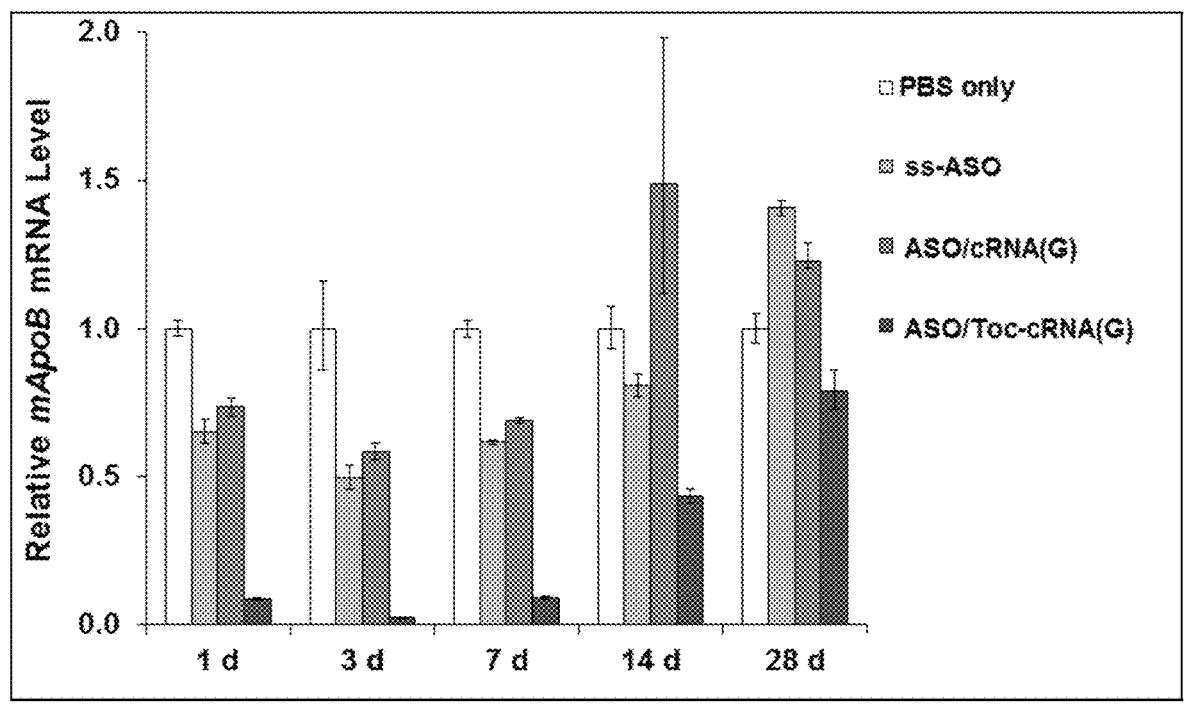
FIG. 19A is a graph illustrating the results obtained by evaluating sustainability of the antisense effect of double-stranded nucleic acid complexes composed of the antisense strand and complementary chains having tocopherol bound thereto as illustrated in FIG. 15. In the diagram, "d" represents the number of days passed after the relevant double-stranded nucleic acid was administered.
Figure 19B:
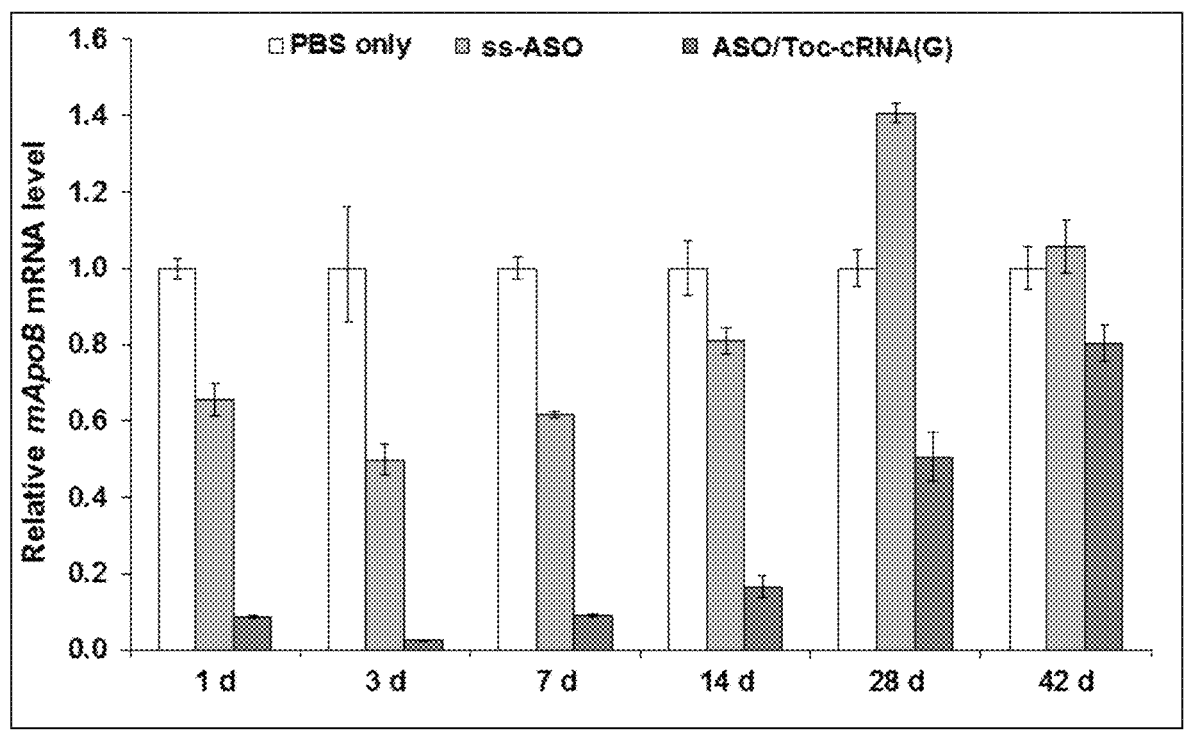
FIG. 19B is a graph illustrating the results obtained by evaluating sustainability of the antisense effect of double-stranded nucleic acid complexes composed of the antisense strand and complementary chains having tocopherol bound thereto as illustrated in FIG. 15. In the diagram, "d" represents the number of days passed after the relevant double-stranded nucleic acid was administered.

As shown by the results illustrated in FIG. 19A, the maximum antisense effect was exhibited on the third day after administration in all of the tested nucleic acids. Furthermore, the same degree of antisense effect as was observed on the first day after administration was exhibited even 7 days after administration. Furthermore, it was shown that the expression of the target gene was suppressed to an extent of 60% even 14 days after administration, and to an extent of 20% even 28 days after administration, suppression levels that are measurably significant compared to the single-stranded ASO. In the second experiment, the same general trend was observed, as shown by FIG. 19B. The maximum antisense effect was observed 3 days post-injection, and the level of suppression observed on the first day was exhibited 7 days post-injection. The suppression 14 and 28 days later was observed to be 80% and 50%, respectively, and a measurable effect was observed even 42 days post-injection. Therefore, it was also found that the double-stranded nucleic acids of some embodiments have high sustainability in connection with the antisense effect.

Example 7

Figure 20A:
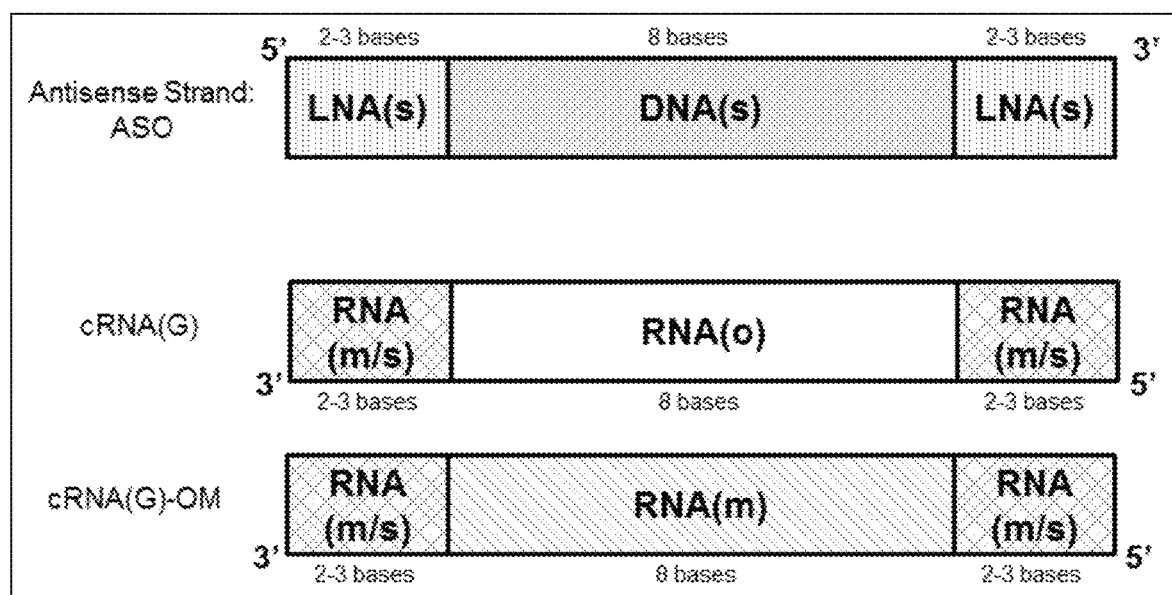
FIG. 20A is a schematic diagram illustrating an antisense oligonucleotide and complementary strands according to certain embodiments.

The antisense effect of the double-stranded nucleic acid complex of another embodiment was evaluated. The composition of the nucleic acid strands compared is schematically illustrated in FIG. 20A. Whereas previous experiments used cRNA(G) (SEQ ID NO: 3), which has a central region of natural RNA bases with 2'-OMe modified, phosphorothioated 5' and 3' wing regions, here, a complementary strand contained the same 5' and 3' wings (two terminal 2'-OMe modified RNA bases and phosphorothioate links), but the central 8 bases were 2'-OMe modified RNA with a natural phosphodiester link between the nucleotides (cRNA(G)-OM)(SEQ ID NO: 9).

That is, the 12-mer LNA/DNA gapmer against mouse apolipoprotein B (mApoB), and 12-mer complementary strands incorporating modified RNA bases to different degrees were designed and produced.

```
Antisense LNA/DNA gapmer strand
ASO 12-mer:
                                      (SEQ ID NO: 1)
       5'-GCattggtatTC-3'
(Upper case: LNA, lower case: DNA,
phosphorothioate bonds between nucleic acids at
all sites)

Complementary strands
       1. cRNA(G):
                                      (SEQ ID NO: 3)
       5'-g_sa_sAUACCAAU_sg_sc-3'

2. cRNA(G)-OM:
                                      (SEQ ID NO: 9)
       5'-g_sa_sauaccaau_sg_sc-3'
(Upper case: RNA, lower case: 2'-OMe-RNA,
s: phosphorothioate bonds between nucleic
acids)
```

Regarding the LNA/DNA gapmer, a product produced by commissioning Gene Design, Inc. was used. Regarding the complementary strands, products produced by commissioning Hokkaido System Science Co., Ltd. were used.

Further, the LNA/DNA gapmer and each of the complementary strands were mixed in equimolar amounts, and the mixture was heated at 95° C. for 5 minutes. Subsequently, the mixture was left to stand at a constant temperature of 37° C. for one hour to anneal the strands. Also, if any product was not to be used immediately, the product was stored at 4° C. thereafter.

Subsequently, the double-stranded nucleic acid comprising LNA 12-mer and cRNA 12-mer (ASO/cRNA(G)), or the double-stranded nucleic acid comprising LNA 12-mer and cRNA(G)-OM 12-mer (ASO/cRNA(G)-OM) was intravenously injected through the tail vein of a mouse in an amount of 0.75 mg/kg. Control mice receiving administrations of PBS only were also prepared. Three days after the intravenous injection, the mice were perfused with PBS, and then the livers were extracted. Subsequently, extraction of mRNA, synthesis of cDNA, and quantitative RT-PCR were carried out by the same methods as the methods described in Comparative Example 1, the amount of expression of mApoB/amount of expression of mGAPDH (internal standard gene) was calculated, and a comparison was made between the group administered with PBS only (PBS only) and the groups administered with a nucleic acid. The results thus obtained are presented in FIG. 20B.

Figure 20B:
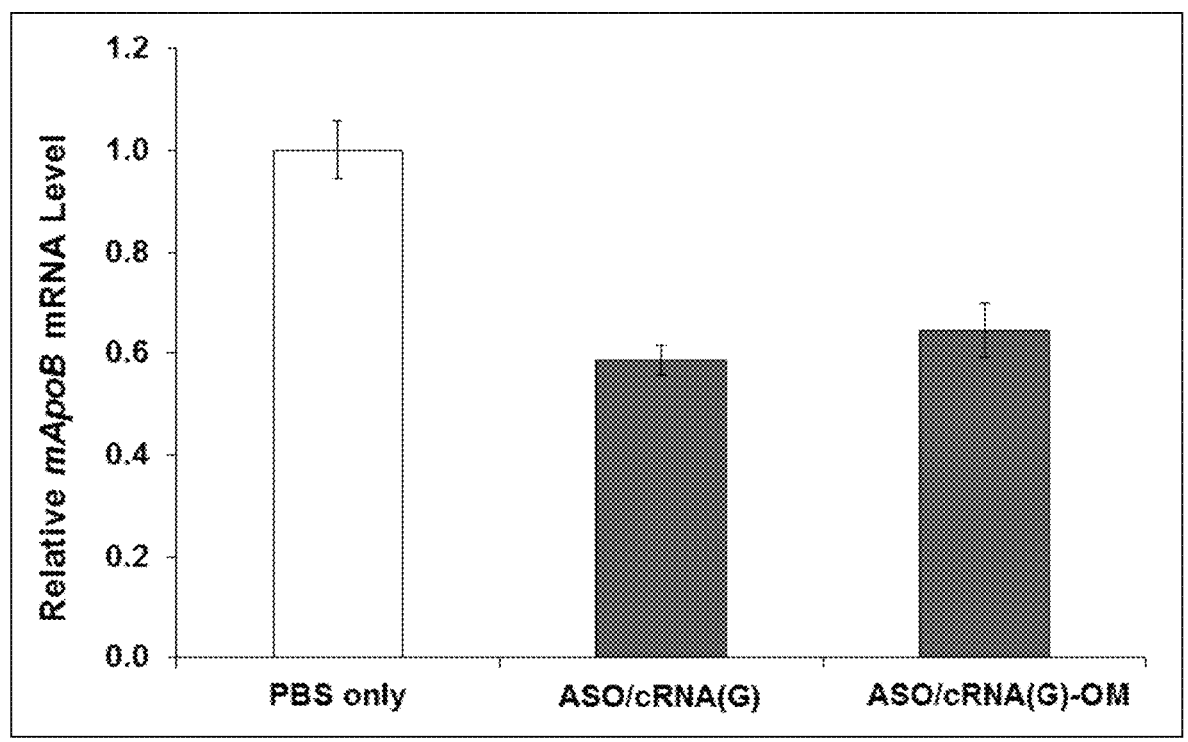
FIG. 20B is a graph comparing the results obtained by evaluating the antisense effect of the double-stranded nucleic acid complex (LNA/cRNA(G)-OM) according to one embodiment of the present invention, which has a complementary strand comprising RNA that is entirely 2'-O-methylated.

As shown by the results illustrated in FIG. 20B, even when cRNA(G)-OM was used instead of cRNA(G) in the double-stranded nucleic acid complex embodiment of the present invention, the antisense effect was not lost.

Generally, when a pharmaceutical product is enterally administered (oral administration, or the like), since the pharmaceutical product is exposed to RNase A in the intestinal tract, it is highly preferable that a nucleic acid drug containing RNA have all the relevant parts of RNA modified by 2'-OMe or the like.

Therefore, since an RNA strand that is entirely modified by 2'-OMe can also be used as a complementary strand for the double-stranded nucleic acid of some embodiments, it was found that the double-stranded nucleic acid of some embodiments can be applied to embodiments of enteral administration.

Example 8

In regard to a double-stranded nucleic acid complex comprising a LNA/DNA gapmer and Toc-cRNA, it was found as discussed above that the double-stranded nucleic acid has a high antisense effect and can be delivered to the liver or the like with high specificity and high efficiency.

As such, it is known that when a lipid such as tocopherol is bound, the delivery properties to the liver or the like are dramatically increased, but the delivery to other organs is on the contrary difficult. Currently, a method for delivery to other organs that is most effectively used is a method of utilizing a kind of target peptide that binds to various proteins on the cell surface of various organs. In some embodiments, it is contemplated to directly bind a peptide as a delivery moiety to a nucleic acid, and thereby utilize a targeting peptide in a double-stranded nucleic acid complex containing a complementary strand comprising RNA such as described above.

In other embodiments, such as demonstrated by the example described below, a peptide nucleic acid (PNA), which can readily be joined to peptide or antibody-based functional moieties, was used as the complementary strand in the double-stranded nucleic acid complex of some embodiments. As shown in the following formula, a PNA does not have phosphate bonds like conventional nucleic acids, but instead had the useful characteristic of having peptide linkages, so that joining a peptide to a PNA strand is made easy. In addition, PNA is characterized by having a high Tm value as in the case of a LNA, so that the double strand is not likely to dissociate, and by having a strong resistance to cleavage by RNase.

[Chem. 2]

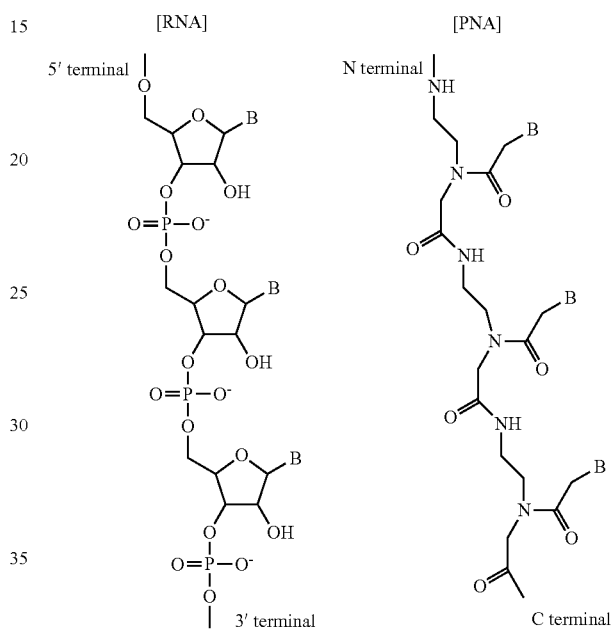

Figure 21A:
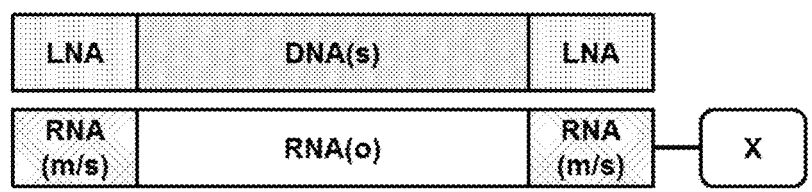
FIGS. 21A-C are schematic diagrams illustrating suitable embodiments of a double-stranded nucleic acid that can be used to incorporate a peptide, protein, or the like as a functional moiety. The symbols in the diagram have the same meanings as those defined in FIGS. 3A-B and FIGS. 4A-B.
Figure 21B:
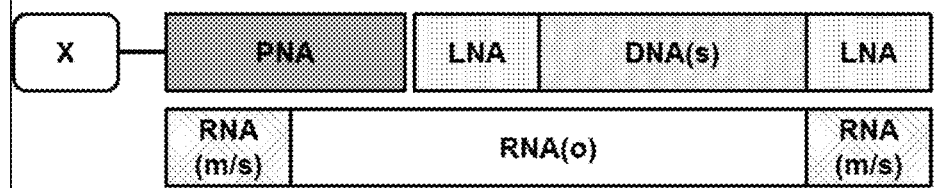
Figure 21C:
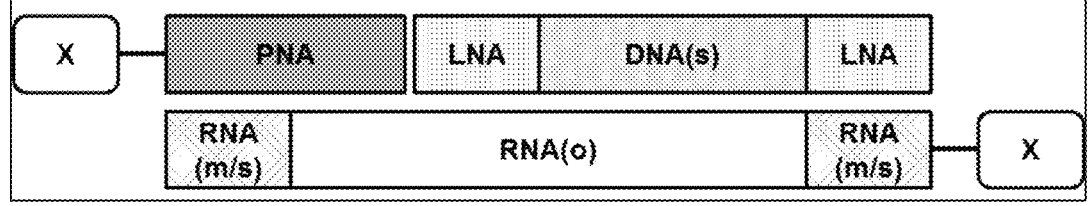

In regard to the demonstration, several embodiments for binding a targeting peptide or the like (peptide-binding strand) to a nucleic acid strand, which is part of the double-stranded nucleic acid complex but where the targeting peptide functional moiety is not directly bound to the LNA/DNA gapmer are contemplated. Examples of such embodiments are shown in FIG. 21A-C. In FIG. 21A, the functional moiety is bound to the complementary RNA strand. In FIG. 21B, three strands are used to form the double-stranded nucleic acid complex. Here, the complementary RNA anneals with both the LNA/DNA antisense strand and a PNA strand. Joining a peptide-based functional moiety to the PNA strands results in a complex carrying a delivery functional moiety, but the moiety is not directly bound to the antisense oligonucleotide. The third strand does not have to be PNA, but could comprise DNA, RNA, and/or nucleotide analogs. Generally, this embodiment provides that a functional moiety can be indirectly associated with the antisense strand by using a complementary strand that is longer than the antisense strand, and preparing a third strand that anneals to the complementary strand in the overhanging portion. Also, as shown in FIG. 21C, the complementary strand can itself be prepared with a functional moiety. The functional moieties shown in FIG. 21C can be independently chosen.

Next, based on this concept, the inventors designed and produced a LNA/DNA gapmer against mouse apolipoprotein B (mApoB), a complementary strand comprising RNA, and a peptide-binding strand as shown below.

```
Antisense LNA/DNA gapmer strand
ASO 12-mer:
                                    (SEQ ID NO: 1)
    5'-GCattggtatTC-3'
(Upper case: LNA, lower case: DNA,
phosphorothioate bonds between nucleic acids
at all sites)

Complementary strand
cRNA 21-mer:
                                    (SEQ ID NO: 10)
    5'-ususcGCACCAGAAUACCAAusgsc-3'
(Upper case: RNA, lower case: 2'-OMe-RNA,
s: phosphorothioate bonds between nucleic acids)

Third (peptide) strand
PNA 9-mer:
                                    (SEQ ID NO: 11)
    N'-TGGTGCGAA-C'
(Underlined: PNA)
```

Regarding the LNA/DNA gapmer, a product produced by commissioning Gene Design, Inc. was used. Regarding the complementary strand, a product produced by commissioning Hokkaido System Science Co., Ltd. was used. Furthermore, regarding the peptide-binding strand, a product produced by commissioning Fasmac Co., Ltd. was used.

The LNA/DNA gapmer, the complementary strand, and the peptide-based strand were mixed in equimolar amounts, and the mixture as heated at 95° C. for 5 minutes. Subsequently, the mixture was left to stand at a constant temperature of 37° C. for one hour to anneal the strands. Also, if the strands were not to be used immediately, the strands were stored at 4° C. thereafter.

Subsequently, ASO 12-mer (ss-ASO) or a double-stranded nucleic acid complex comprising (1) ASO 12-mer, (2) cRNA(G) 21-mer, and (3) PNA 9-mer (ASO, PNA/cRNA(G)) was intravenously injected to a mouse through the tail vein in an amount of 0.75 mg/kg. Furthermore, a mouse to which PBS only was administered was also prepared as a control. Three days after the intravenous injection, the mice were perfused with PBS, and then the livers were extracted. Subsequently, extraction of mRNA, synthesis of cDNA, and quantitative RT-PCR were carried out by the same methods as the methods described in Comparative Example 1, the amount of expression of mApoB/amount of expression of mGAPDH (internal standard gene) was calculated, and a comparison was made between the group administered with PBS only (PBS only) and the groups administered with nucleic acids. The results thus obtained are presented in FIG. 22.

Figure 22:
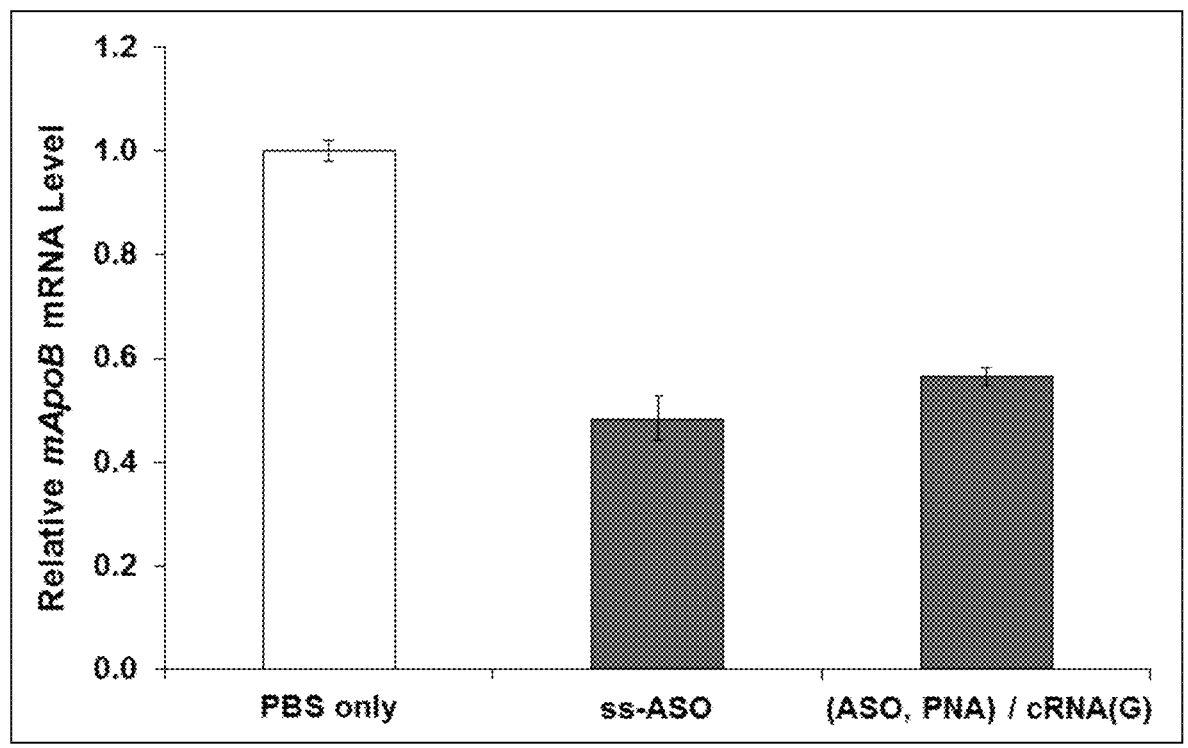

As is obvious from the results illustrated in FIG. 22, the antisense effect of ASO,PNA/cRNA(G) complex was not reduced as compared with the effect of LNA 12-mer.

Example 9

The following example demonstrates that a PNA strand can be used as the complementary strand in the double-stranded nucleic acid complex as an embodiment.

That is, it is contemplated that a PNA strand can be used as the complementary strand, instead of RNA, as illustrated in FIG. 3B. This arrangement also provides an embodiment of a double-stranded nucleic acid complex in which a functional moiety such as a targeting peptide is not directly bound to the antisense strand (e.g., LNA/DNA gapmer) but is indirectly associated with it.

Based on this concept, a LNA/DNA gapmer against mouse apolipoprotein B (mApoB), and a complementary strand comprising PNA were designed and produced as shown below.

```
Antisense LNA/DNA gapmer strand
ASO 12-mer:
                                    (SEQ ID NO: 1)
    5'-GCattggtatTC-3'
(Upper case: LNA, lower case: DNA,
phosphorothioate bonds between nucleic acids
at all sites)

Complementary strands
1. cPNA 12-mer:
                                    (SEQ ID NO: 12)
    N'-GAAUACCAAUGC-C'

2. cPNA 10-mer:
                                    (SEQ ID NO: 13)
    N'-GAAUACCAAU-C'

3. cPNA 8-mer:
                                    (SEQ ID NO: 14)
    N-GAAUACCA-C'
(underlined: PNA)
```

Regarding the LNA/DNA gapmer, a product produced by commissioning Gene Design, Inc. was used. Regarding the complementary strand, a product produced by commissioning Fasmac Co., Ltd. was used.

The LNA/DNA gapmer and each of the complementary strands were mixed in equimolar amounts, and the mixture as heated at 95° C. for 5 minutes. Subsequently, the mixture was left to stand at a constant temperature of 37° C. for one hour to anneal the strands. Also, if the strands were not to be used immediately, the strands were stored at 4° C. thereafter.

Subsequently, ASO 12-mer (ss-ASO), a double-stranded nucleic acid comprising ASO 12-mer and cPNA 12-mer (ASO/cPNA 12-mer), a double-stranded nucleic acid comprising ASO 12-mer and cPNA 10-mer (ASO/cPNA 10-mer), or a double-stranded nucleic acid comprising ASO 12-mer and cPNA 8-mer (ASO/cPNA 8-mer) were intravenously injected to a mouse through the tail vein in an amount of 0.75 mg/kg. Furthermore, a mouse to which PBS only was administered was also prepared as a control. Three days after the intravenous injection, the mice were perfused with PBS, and then the livers were extracted. Subsequently, extraction of mRNA, synthesis of cDNA, and quantitative RT-PCR were carried out by the same methods as the methods described in Comparative Example 1, the amount of expression of mApoB/amount of expression of mGAPDH (internal standard gene) was calculated, and a comparison was made between the group administered with PBS only (PBS only) and the groups administered with nucleic acids. The results thus obtained are presented in FIG. 23.

Figure 23:
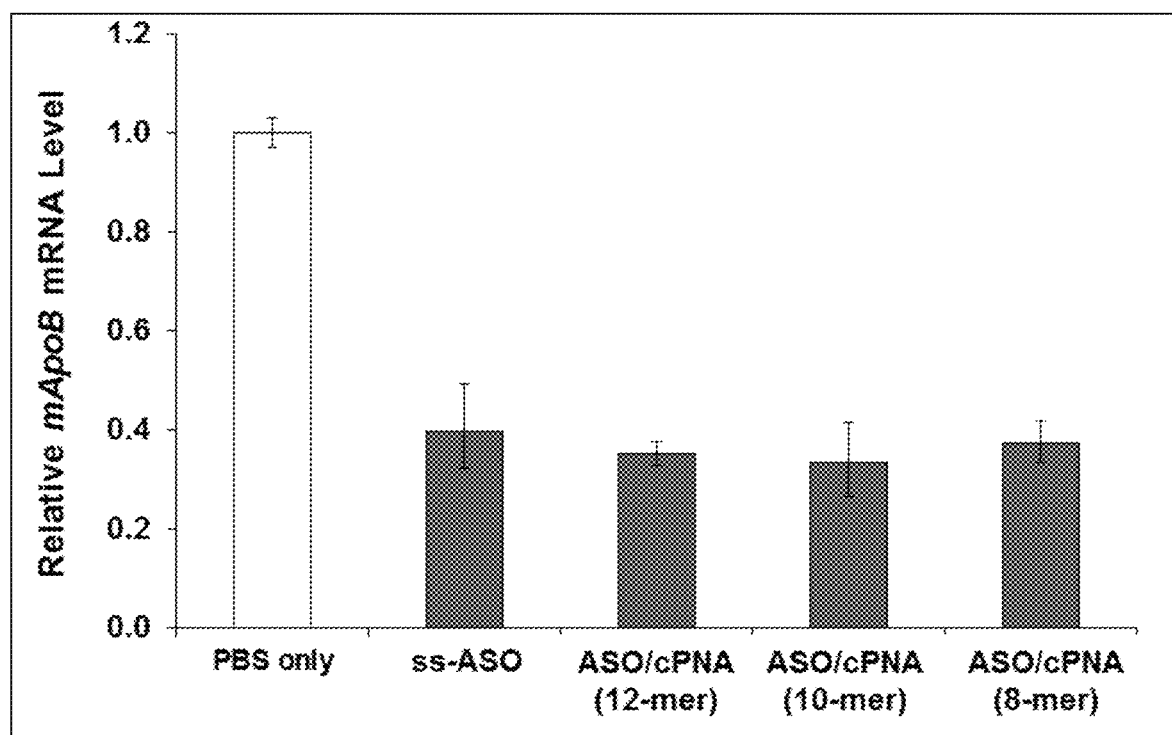
FIG. 23 is a graph illustrating the results obtained by evaluating the antisense effect of double-stranded nucleic acid complexes composed of an antisense strand and a complementary strand comprising PNA.

As shown by the results illustrated in FIG. 23, the antisense effect of any of the ASO/cPNA complexes was at least as strong as the effect observed for the ss-ASO 12-mer.

Example 10

Figure 24:
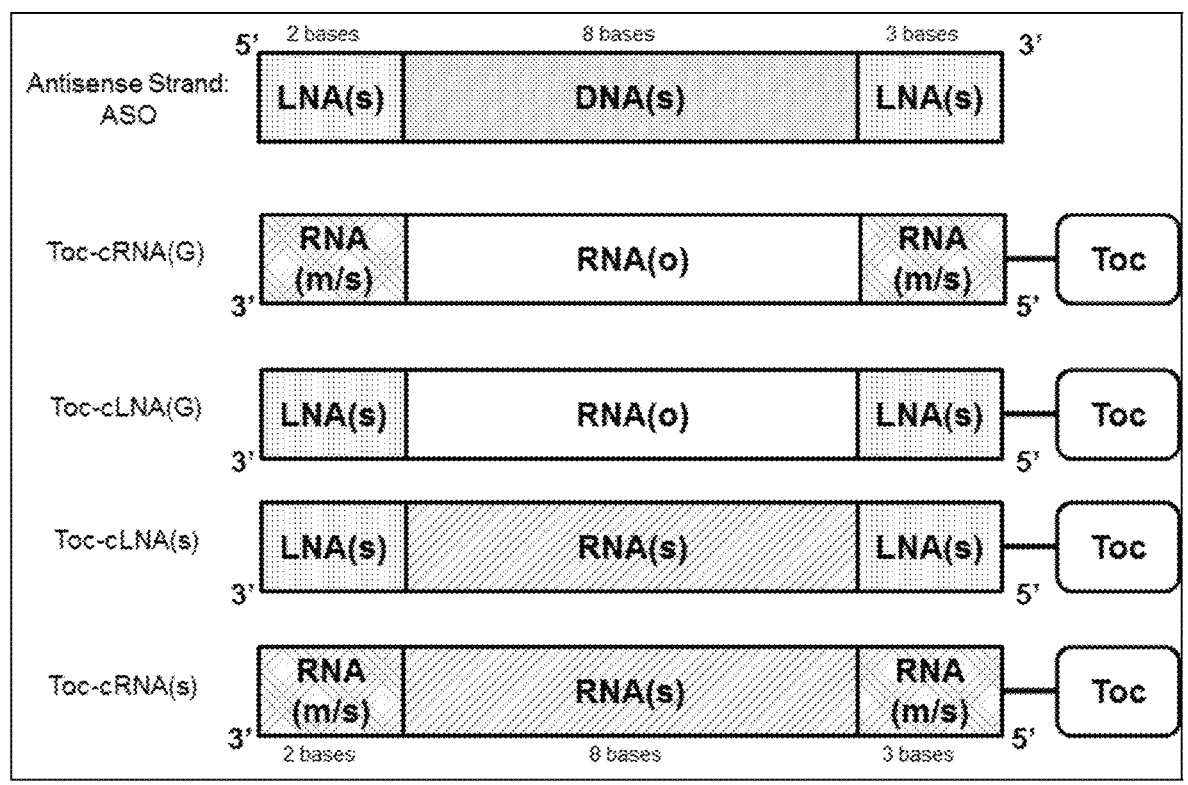
FIG. 24 is a schematic diagram illustrating an antisense oligonucleotide and complementary strands according to certain embodiments.

This example demonstrated that various structures for the complementary strand that comprise "RNA nucleotides and optionally nucleotide analogs" can be used in the double-stranded nucleic acid complex and will yield an antisense effect. Four types of complementary strand structures were designed and prepared. The structures are schematically illustrated in FIG. 24. As the figure shows, two types of 5' and 3' wing regions were combined with two types of central regions. The wing regions comprise either 2'-OMe modified RNA with phosphorothioate links, or the nucleotide analog LNA, with phosphorothioate links. The central region comprises either natural phosphodiester-linked RNA, or phosphorothioate-linked RNA.

The following 13-mer nucleic strands were produced and tested:

```
Antisense LNA/DNA gapmer strand
ASO 13-mer:
                                    (SEQ ID NO: 5)
    5'-GCattggtatTCA-3'
(Upper case: LNA, lower case: DNA,
phosphorothioate bonds between nucleic acids
at all sites)

Complementary strands
1. Toc-cRNA(G):
                                    (SEQ ID NO: 7)
    5'-u,g,a,AUACCAAU,g,c-3'

2. Toc-cLNA(G):
                                    (SEQ ID NO: 15)
    5'-u,g,a,AUACCAAU,g,c-3'

3. Toc-cLNA(s):
                                    (SEQ ID NO: 16)
    5'-u,g,a,A,U,A,C,C,A,A,U,g,c-3'

4. Toc-cRNA(s):
                                    (SEQ ID NO: 17)
    5'-u,g,a,A,U,A,C,C,A,A,U,g,c-3'
(Upper case: RNA, lower case: 2'-OMe-RNA,
underlined lower case: LNA, s: phosphorothioate
bonds between nucleic acids)
```

The LNA/DNA gapmer and each of the complementary strands were mixed in equal molar amounts and annealed as described above in Example 7. Next, the annealed double-stranded nucleic acid complexes were intravenously injected through the tail vein of a mouse in an amount of 0.75 mg/kg. A control mouse was also prepared by injecting PBS solution through the tail vein. Three days after the injection, the mice were perfused with PBS, the livers extracted, and subsequently mRNA extraction, cDNA synthesis, and quantitative RT-PCR was carried out as described in Comparative Example 1. The relative mApoB expression level compared to mGAPDH (internal standard gene) was calculated, and the results are presented in FIGS. 25A-B.

Figure 25A:
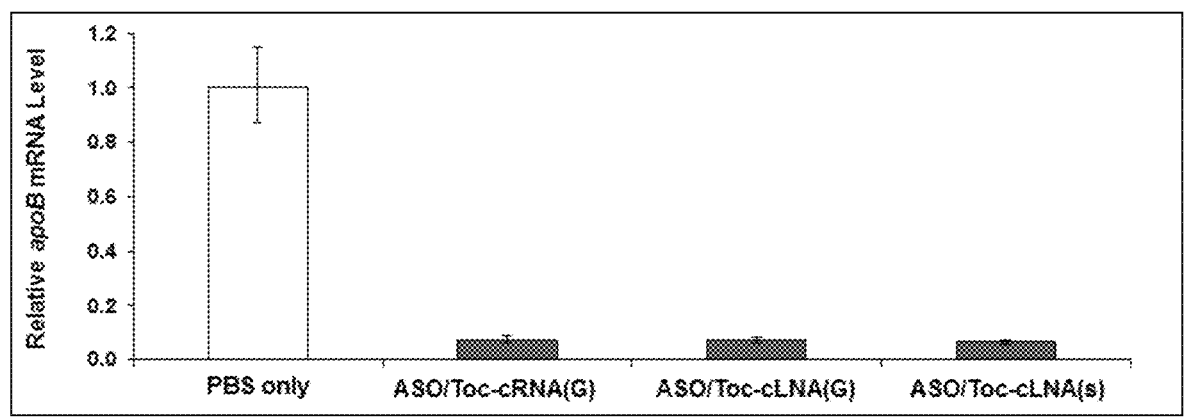
FIG. 25A is a graph illustrating the results obtained for double-stranded nucleic acid complexes prepared with the strands shown in FIG. 24.
Figure 25B:
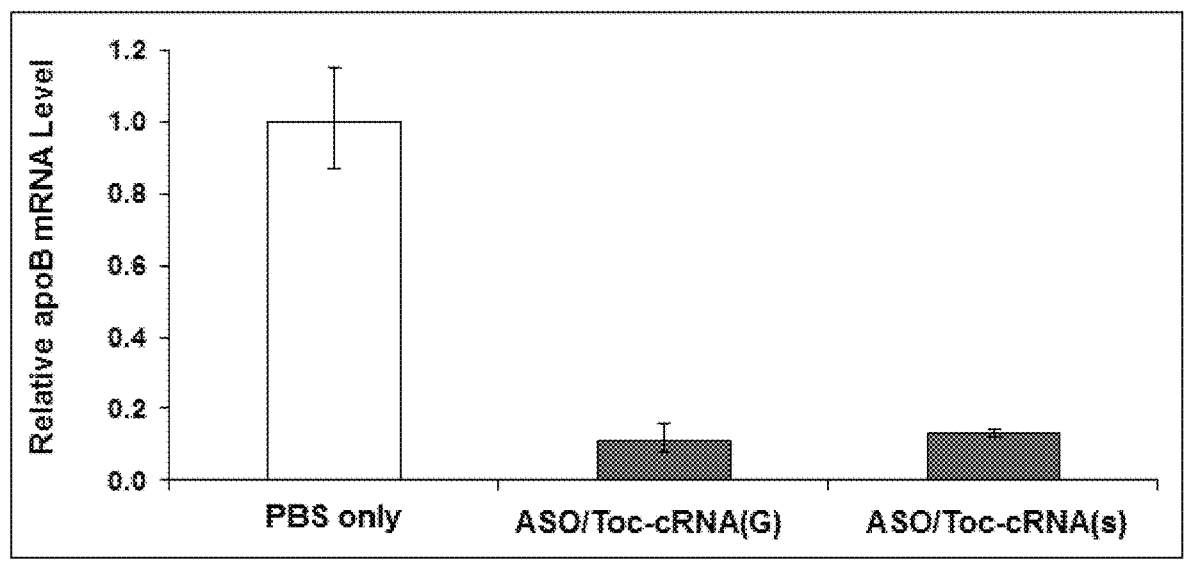
FIG. 25B is a graph illustrating the results obtained for double-stranded nucleic acid complexes prepared with the strands shown in FIG. 24.

As shown by FIG. 25A, comparing the results of Toc-cRNA(G) with Toc-cLNA(G), the 5' and 3' wing regions of the complementary strand can be prepared using bridged nucleic acids as well as RNA, and a similarly large antisense effect can be obtained. The data further show that for either of these types of wing regions, the central RNA portion of the nucleic acid strand can phosphorothioated, and the antisense effect remains as large as that observed with natural RNA in the central portion of the strand. Compare Toc-cLNA(s) and Toc-cRNA(s) in relation to the effect observed for Toc-cRNA(G), in FIGS. 25A and 25B, respectively.

As discussed in conjunction with Example 7, this example further shows other embodiments in which the nuclease resistance of the complementary strand can be increased without lose of the antisense effect. Specifically, the full length of the strand can be phosphorothioated and yet where central region comprises phosphorothioate-modified RNA, the antisense strand can still be released and suppress level of the mRNA transcript.

Example 11

This example demonstrated that even if the first and second strands (antisense and complementary strands) have different lengths the antisense effect is still obtained. Here, a 13-mer LNA/DNA gapmer was annealed with a 31-mer complementary RNA-based strand and tested for suppression of expression of ApoB gene in mice. Furthermore, the 31-mer was prepared with a 5' wing comprising three 2'-OMe modified, phosphorothioated RNA nucleotides, a 3' wing comprising twenty 2'-OMe modified, phosphorothioated RNA nucleotides, and a central region comprising eight RNA nucleotides that have a phosphorothioate link. The activity of the 13-mer/31-mer complex was compared with the activity of a 13-mer/13-mer complex.

```
Antisense LNA/DNA gapmer strand
LNA 13-mer:
                                    (SEQ ID NO: 5)
    5'-GCattggtatTCA-3'
(Upper case: LNA, lower case: DNA,
phosphorothioate bonds between nucleic acids
at all sites)

Complementary strands
1. 13-mer Toc-cRNA(G):
                                    (SEQ ID NO: 7)
    5'-u,g,a,AUACCAAU,g,c-3'

2. 31-mer Toc-cRNA(s):
                                    (SEQ ID NO: 18)
    5'-u,g,a,AUACCAAUgcuacgcauacgcacca,c,c,a-3'
(Upper case: RNA, lower case: 2'-OMe-RNA,
s: phosphorothioate bonds between nucleic acids)
```

The LNA/DNA gapmer and each of the complementary strands were mixed in equal molar amounts and annealed as described above in Example 7. Next, the annealed double-stranded nucleic acid complexes were intravenously injected through the tail vein of a mouse in an amount of 0.75 mg/kg. A control mouse was also prepared by injecting PBS solution through the tail vein. Three days after the injection, the mice were perfused with PBS, the livers extracted, and subsequently mRNA extraction, cDNA synthesis, and quantitative RT-PCR was carried out as described in Comparative Example 1. The relative mApoB expression level compared to mGAPDH (internal standard gene) was calculated, and the results are presented in FIG. 26.

Figure 26:
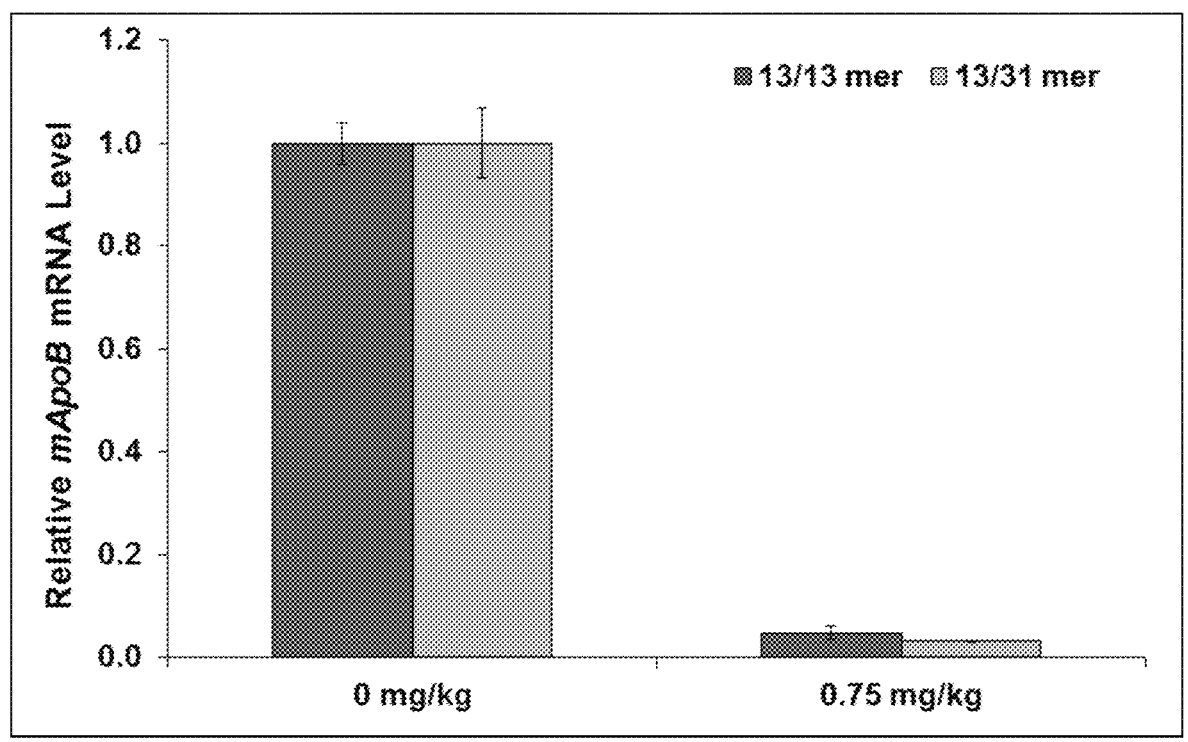
FIG. 26 is a graph illustrating the results obtained in Example 11 for suppression of expression using double-stranded nucleic acid complexes.

As shown by FIG. 26, comparing the suppression achieved with double-stranded complexes having a 31-mer Toc-cRNA(s) complementary strand versus those having a 13-mer Toc-cLNA(G) complementary strand shows that a similarly large antisense effect was obtained. The data further show that the central RNA portion of the nucleic acid strand can phosphorothioated and the antisense effect remains as large as that observed with natural RNA in the central portion of the strand, even if the complementary strands also differ in length.

Example 12

To demonstrate the sequence-specificity and the universal applicability of the antisense effect provided by the double-stranded nucleic acids complexes disclosed herein, antisense probes targeting the transcription product of a different gene, human transthyretin (hTTR) were prepared. The experiments were performed using transgenic mice, altered to contain hTTR. (The mice thus contain both hTTR and mTTR.) The antisense and complementary strands were prepared in two lengths, as 13-mer and 20-mer strands, and they were tested as the 13-mer/13-mer and 20-mer/20-mer double-stranded complexes. Also, the complementary strand was prepared with a 5'-tocopherol functional moiety to direct the complex to the liver. Furthermore, because hTTR expression ultimately yields a protein observable in the blood, the serum concentration of the expressed protein was analyzed, and was found to decrease following injection of the double-stranded nucleic acid complex. The sequence and composition of the various strands designed, produced, and tested are shown below.

```
Antisense LNA/DNA gapmer strands
1. ASO 13-mer:
                                    (SEQ ID NO: 19)
    5'-TGtctctgccTGG-3'

2. ASO 20-mer:
                                    (SEQ ID NO: 21)
    5'-TTATTgtctctgcctGGACT-3'
(Upper case: LNA, lower case: DNA,
phosphorothioate bonds between nucleic acids
at all sites)

Complementary strands
1. 13-mer Toc-cRNA(G):
                                    (SEQ ID NO: 20)
    5'-cscsasGGCAGAGAscsa-3'

2. 20-mer Toc-cRNA(G):
                                    (SEQ ID NO: 22)
    5'-asgsuscscsAGGCAGAGACsasasusasa-3'
(Upper case: RNA, lower case: 2'-OMe-RNA,
s: phosphorothioate bonds between nucleic acids)
```

The 13-mer antisense and complementary strands and the 20-mer antisense and complementary strands, respectively, were mixed in equal molar amounts and annealed as described above in Example 7. Next, 13-mer single stranded antisense strand and the 13-mer annealed double-stranded nucleic acid complex were intravenously injected through the tail vein of a transgenic mouse in an amount of 0.75 mg/kg. Similarly, the 20-mer antisense single and 20-mer double-stranded complex were injected in an amount of 6 mg/kg. Control mice were also prepared by injecting PBS solution through the tail vein. Three days after the injection, the mice were perfused with PBS, the livers extracted, and subsequently mRNA extraction, cDNA synthesis, and quantitative RT-PCR was carried out as described in Comparative Example 1. The relative hTTR expression levels compared to mGAPDH (internal standard gene) were calculated, and the results are presented in FIGS. 27A and 27B for the 13-mer and 20-mer strands, respectively.

hTTR that is synthesized in the liver is secreted into the blood. Thus, if antisense probes can be delivered to the liver and are effective in suppressing the expression of hTTR, then the result of the suppression should be the lowering of the blood serum concentration of the protein. Blood serum concentration levels were measured before the injection treatment with the 13-mer nucleic acid strands and again three days post-injection at a commercial lab. The serum concentrations observed are presented in FIG. 28.

Figure 27A:
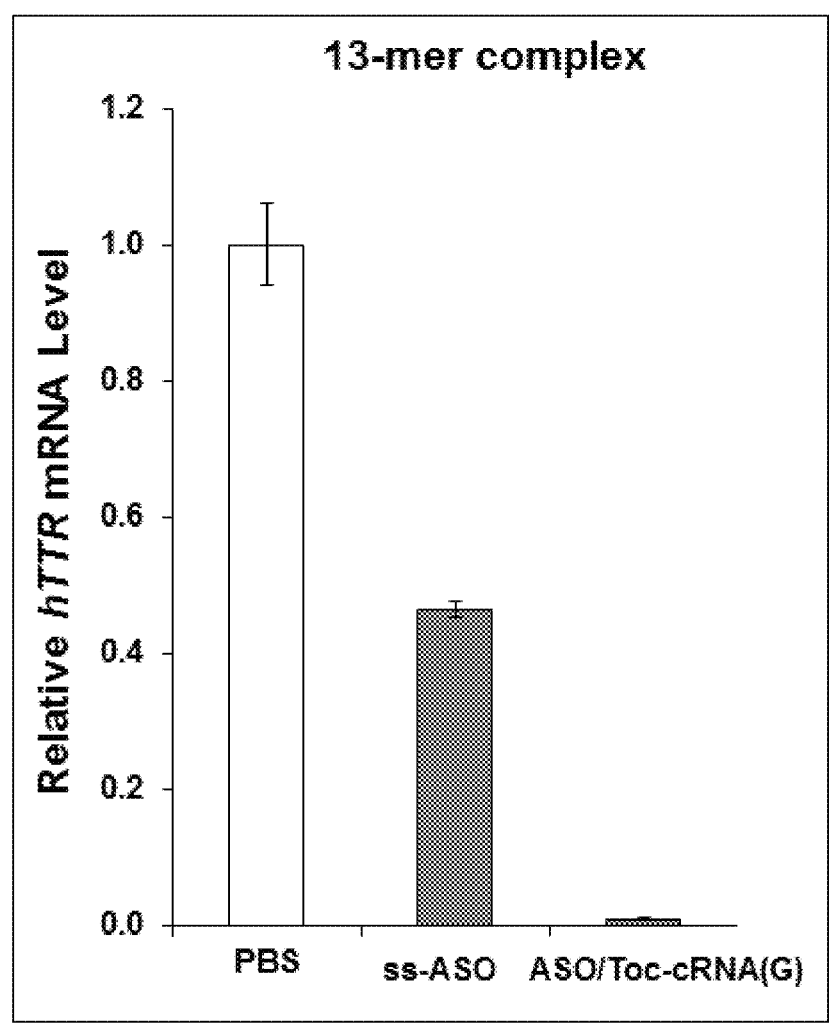
FIG. 27A is a graph illustrating the results obtained in Example 12 evaluating the suppression of expression of hTTR with double-stranded nucleic acid complexes of different length.
Figure 27B:
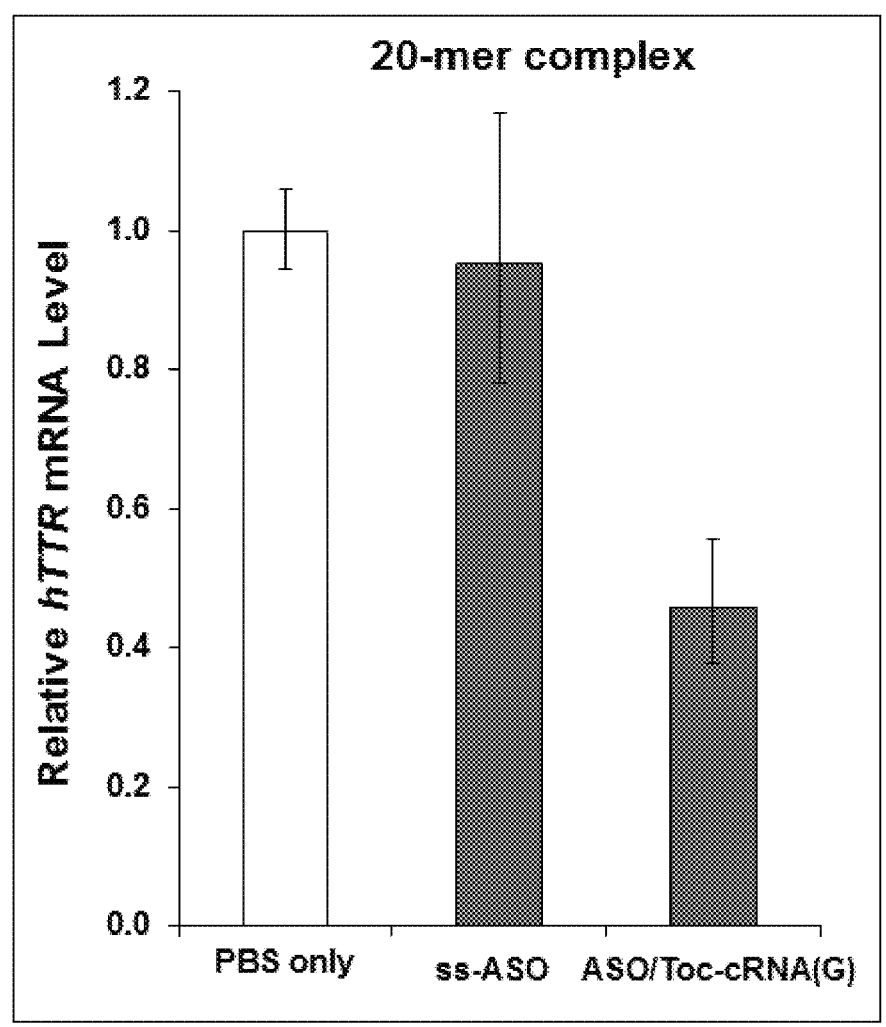
FIG. 27B is a graph illustrating the results obtained in Example 12 evaluating the suppression of expression of hTTR with double-stranded nucleic acid complexes of different length.

As shown by FIG. 27A, the 13-mer double-stranded complex was effective in suppressing the mRNA transcript by more than 95%. In comparison, the single-stranded ASO only yielded a suppression of about 50%. The 20-mer complex also yielded a similar level of suppression of about 50%, whereas the single-stranded 20-mer had essentially no suppression, as illustrated in FIG. 27B. This falloff in the ability to suppress expression is commonly observed as the oligonucleotide increases in length. However, the longer oligonucleotides also are more selective and thus may be more safe. The efficacy of a treatment can be tailored by adjusting, for example, the dosage amount, dosing regimen, and the length, sequence, and composition of the antisense strand. However, as shown by these examples, delivering the antisense strand as a double-stranded nucleic acid complex according to the various embodiments of the present invention yields a significantly greater degree of suppression than when the same antisense strand is delivered as a single strand.

Figure 28:
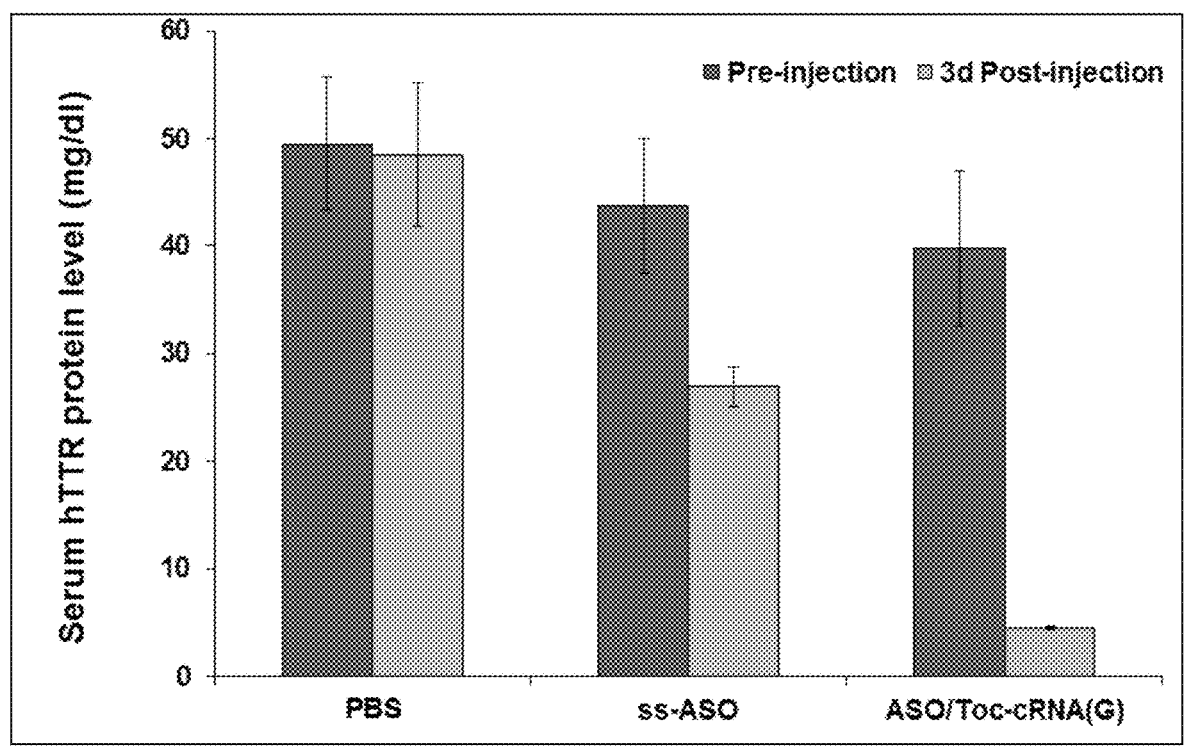
FIG. 28 is a graph illustrating the results obtained in Example 12 evaluating the serum protein level for a protein targeted by a double-stranded nucleic acid complex before and after treatment.

The pre- and post-treatment serum concentration levels are shown in FIG. 28, and the results show a significant reduction in hTTR caused by the 13-mer double-stranded complex from ~40 mg/dl to <5 mg/dl, compared with the single-stranded 13-mer (~44 mg/dl to ~28 mg/dl) and the PBS control (approximately no change).

Example 13

This example demonstrated the delivery of a double-stranded nucleic acid complex to cells of the nervous system using a peptide as the delivery functional moiety. A double-stranded complex comprising three strands, an antisense strand, a complementary strand, and a PNA strand, having the general structure illustrated in FIG. 21B was used. A dodecapeptide, DRG1, was joined to the N-terminal of a 9-mer PNA strand to act as a delivery agent to localize the complex in dorsal root ganglia (DRG) cells. This 9-mer PNA was annealed with a 13-mer antisense strand and a 22-mer complementary strand, which are described below, to form the double-stranded complex used in the experiment. The gene targeted by the antisense strand was TRPV1.

```
Antisense LNA/DNA gapmer strand
ASO 13-mer:
                                    (SEQ ID NO: 23)
    5'-TAgtccagttCAC-3'
(Upper case: LNA; lower case: DNA;
phosphorothioate bonds between nucleic acids
at all sites)

Complementary strand
cRNA(G) 22-mer:
                                    (SEQ ID NO: 24)
    5'-gsusgsAACUGGACuauacgcacscsa-3'
(Upper case: RNA; lower case: 2'-OMe-RNA;
s: phosphorothioate bonds between nucleic acids)

Third (peptide) strand
pep-PNA 9-mer:
                                (SEQ ID NOs: 25 and 31)
    N'-SPGARAFGGGGS-tggtgcgta-C'
(Upper case: amino acid; Underlined, lower
case: PNA)
```

The LNA/DNA gapmer, the complementary strand, and the peptide-PNA strand were mixed in equimolar amounts, and the mixture as heated at 95° C. for 5 minutes. Subsequently, the mixture was left to stand at a constant temperature of 37° C. for one hour to anneal the three strands ("ts-TRPV1"). Also, if the strands were not to be used immediately, the strands were stored at 4° C. Also, a double-stranded complex comprising just the antisense strand and the complementary strand ("ds-TRPV1") was prepared the same way.

Mice were obtained from Sankyo Lab (Tokyo, Japan), kept within a pathogen-free animal facility and provided food and water ad libitum. Eight-week old female ICR mice weighing on average 27 g received 2.66 ug intra-thecal injections of PBS, ds-TRPV1, or ts-TRPV1. Animal procedures were performed by a physician licensed for animal experimentation, in accordance with ethical and safety protocols approved by the Animal Experiment Committee of Tokyo Medical and Dental University. Intra-thecal injection was administered following induction of anaesthesia via intra-peritoneal injection of chloral hydrate (0.5 mg/g body weight) and ketamine hydrochloride (0.05 mg/g body weight). All mice were placed in the prone position and underwent partial laminectomy of the second and third lumbar vertebrae (L2-L3). Once exposed, the dura mater between these vertebrae was punctured using s 27-gauge needle; subsequently, a PE-10 catheter connected to a 10 uL Hamilton syringe was inserted caudally into the subarachnoid space to approximately the level of L5 and a 10 uL volume was steadily administered over a 1-minute period. After the removal of the catheter, the fascia and skin were sutured with 4-O-nylon thread and treated with antibiotic solution. The animals were then positioned in the head-up position and allowed to recover on a heated pad.

Histological analysis was performed as follows. Mice were euthanized 2 days after injection via 3 mg chloral hydrate intra-peritoneal injection and transcardial fixation with PFA (4% paraformaldehyde in PBS) following PBS perfusion. DRG (unilteral L6) were harvested. The DRG thus obtained were fixed with a 4% formalin solution, subsequently the solution was replaced with a 30% sucrose solution, the livers were embedded in OCT Compound, and then sections having a thickness of 10 µm were produced therefrom. Subsequently, the sections were nucleus stained by using DAPI, and then the signal intensities of Cy3 in the sections were observed using a confocal microscope. The confocal imaging analysis is shown in FIG. 29.

Relative expression level analysis of TRPV1 was performed as follows. Mice were sacrificed 7 days after injection via induction of anaesthesia and transcardial PBS perfusion. Three unilateral DRG were harvested from each mouse: lumbar spinal DRG (LSD) L4, L5, and L6. Thereafter, mRNA extraction, cDNA synthesis, and quantitative RT-PCR was carried out as described in Comparative Example 1. The relative mTRPV1 expression levels compared to mGAPDH (internal standard gene) were calculated, and the results are presented in FIG. 30.

Figure 29:
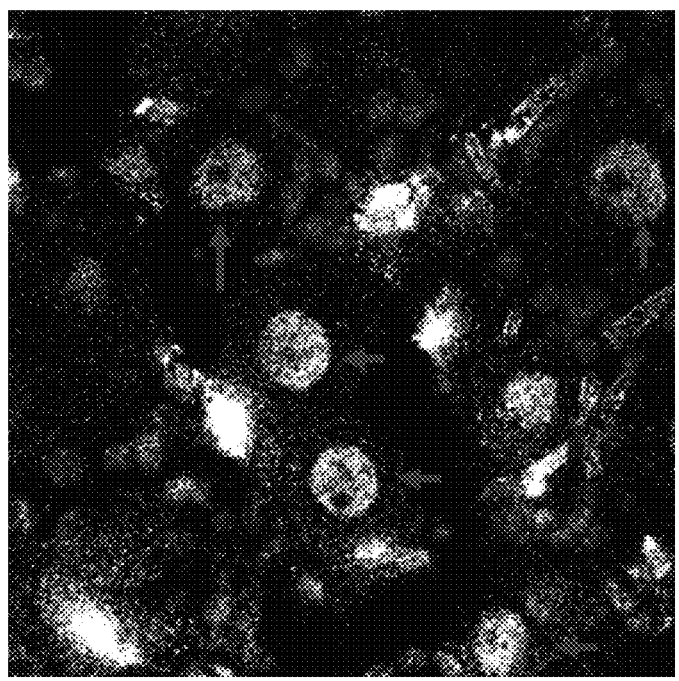
FIG. 29 is a fluorescent image showing the results obtained in Example 13 showing localization of a double-stranded nucleic acid complex comprised of three strands.

The histological analysis, shown in FIG. 29, reveals that the Cy3-labeled antisense strand localized to the nucleus of DRG cells. This is evidenced by the coincident fluorescent signals of the nuclear stain the fluorescent label on the antisense strand. Again, this experiment demonstrated that the double-stranded complex comprising three strands remained intact and the delivery moiety on the third strand directed the complex, and thereby the antisense strand, to the cell of interest.

Figure 30:
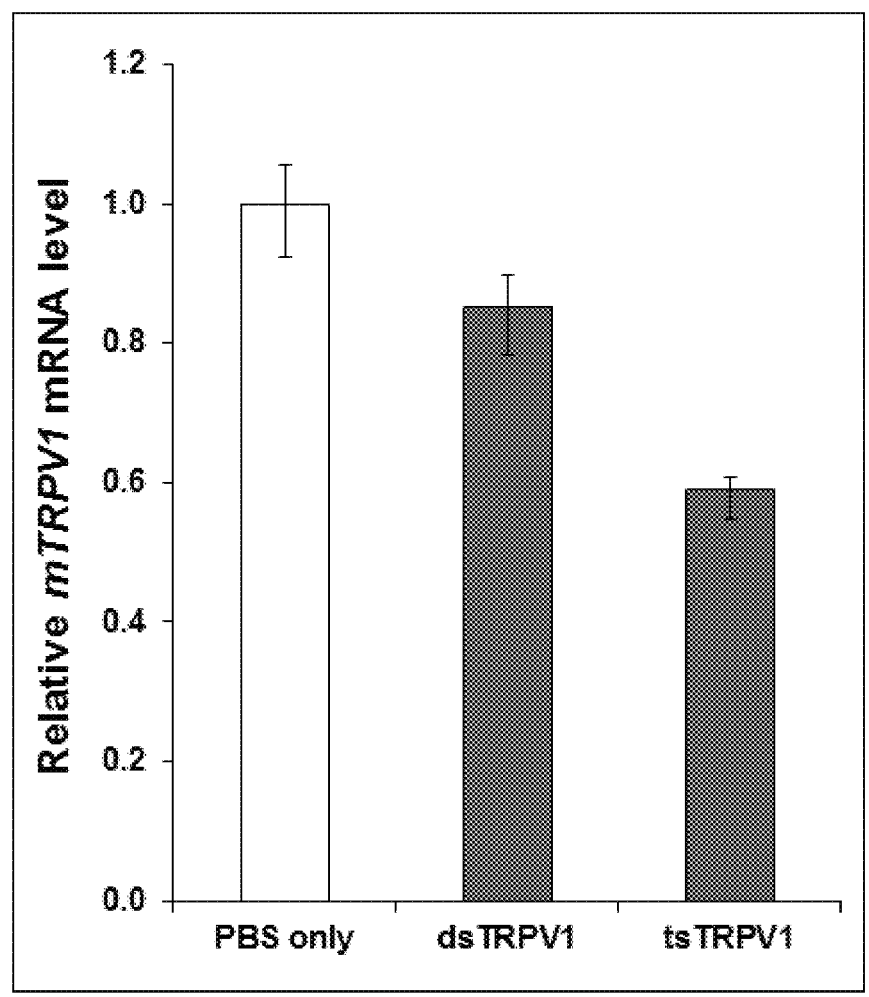
FIG. 30 is a graph illustrating the results of Example 13 showing suppression of expression caused by a double-stranded nucleic acid complex comprised of three strands.

The antisense effect is observed, as shown in FIG. 30 by the suppression of the expression of mTRPV1. The complex, ts-PRPV1, which contains the peptide-PNA strand and thus can guide the complex to DRG cells, demonstrated a suppression of about 40%. In contrast, the ds-TRPV1 complex, which lacked the peptide-PNA strand suppressed the gene expression, but only by about 20%. This example again demonstrated the ability to deliver an antisense strand to a specific cell type using complexes comprising three strands. Furthermore, this example illustrates the use of a peptide to guide the delivery, and achieves this in a cell type (DRG) and organ different from that illustrated in other examples (nervous system instead of the liver).

Example 14

This example demonstrated an antisense effect by the double-stranded nucleic acid complex against non-protein encoding RNA transcript products, namely, against an miRNA. In a mouse liver, miR-122, an miRNA, is known to be expressed. A 15-mer anti-miR strand was designed and prepared with a 5' wing and a 3' wing comprising three nucleotides analogs (bridged nucleic acid, LNA), and a 9 base central region comprising DNA, wherein all the links were phosphorothioated. A complementary strand with 5' and 3' wings comprising 2'-OMe, phosphorothioated RNA and a central region comprising natural RNA was prepared.

```
Anti-miR LNA/DNA gapmer strand
ASO 15-mer:
                                      (SEQ ID NO: 26)
        5'-CCAttgtcacacTCC-3'
(Upper case: LNA; lower case: DNA;
phosphorothioate bonds between nucleic acids
at all sites)

Complementary strand
        Toc-cRNA(G) 15-mer:
                                      (SEQ ID NO: 27)
        5'-Toc-gₛgₛaₛGUGUGACCAₛuₛgₛg-3'
(Upper case: RNA; lower case: 2'-OMe-RNA;
s: phosphorothioate bonds between nucleic acids)
```

The anti-miR LNA/DNA gapmer and the complementary strand were mixed in equal molar amounts and annealed as described above in Example 7. Next, the single-stranded anti-miR strand and the annealed double-stranded nucleic acid complexes were intravenously injected through the tail vein of a mouse in an amount of 0.75 mg/kg. A control mouse was also prepared by injecting PBS solution through the tail vein. Three days after the injection, the mice were perfused with PBS, the livers extracted, and subsequently mRNA extraction, cDNA synthesis, and quantitative RT-PCR was carried out as described in Comparative Example 1. The relative mApoB expression level compared to mGAPDH (internal standard gene) was calculated, and the results are presented in FIG. 31.

Figure 31:
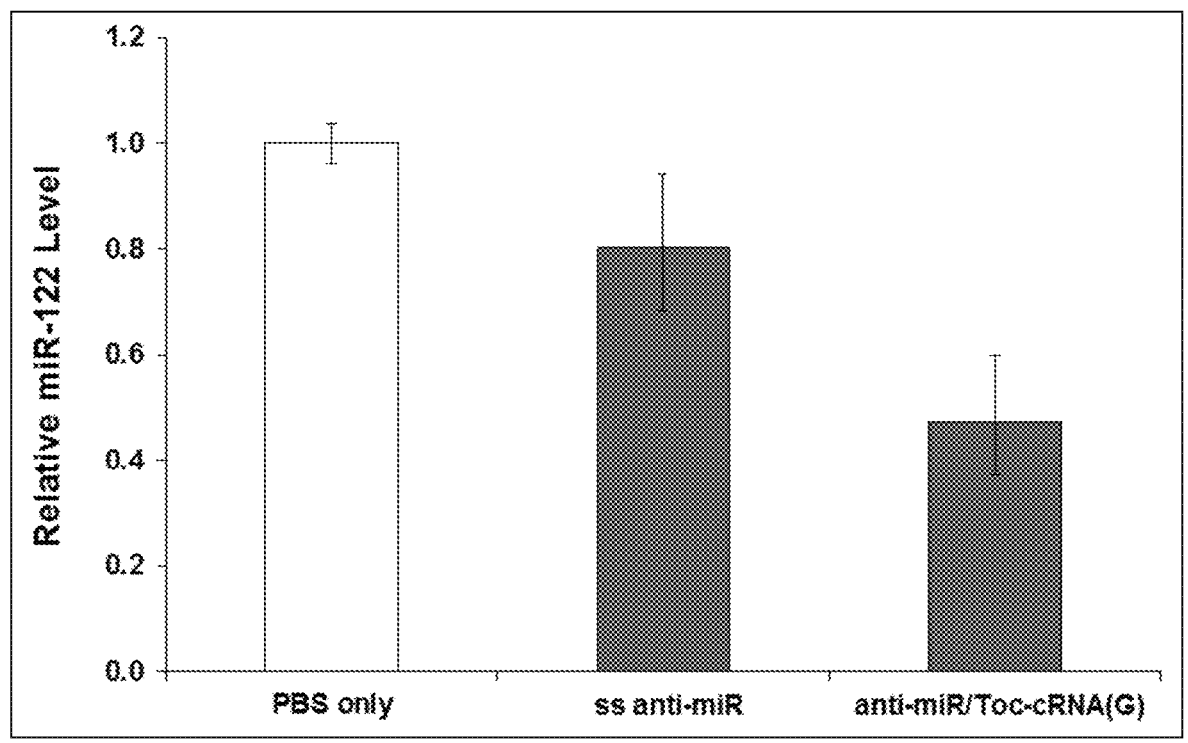
FIG. 31 is a graph illustrating the results of Example 14 showing suppression of the level of an miRNA.

As shown by FIG. 31, the double-stranded complex provides nearly a 50% reduction in the level of miR-122, whereas the single stranded anti-miR oligonucleotide provided just a ~20% reduction. It is also noteworthy that the typical methods for reducing miRNA levels use a mixmer type probe structure, and the probe needs to be delivered at a dose of ~10 mg/kg to achieve a 50% reduction (ED50). As illustrated, the double-stranded complex according to some embodiments that is presented in this example achieves ED50 at a considerably lower dosage amount.

Example 15

This example used an antisense strand comprising "amideBNA" amido-bridged nucleic acids to achieve an antisense effect. Amido-bridged nucleic acids (also referred to as "AmNAs") are analogs of LNAs that have a cyclic amide bridge (4'-C(O)—N(R)-2'; R=H, Me) joining the 2' and 4'-carbons of the sugar ring. The synthesis of AmNAs, their incorporation into oligonucleotides and the properties thereof, such as binding affinity and nuclease resistance, were recently disclosed by A. Yahara et al., in ChemBioChem 2012, 13, 2513-2516, the disclosure of which is incorporated by reference. As disclosed by Yahara et al., AmNAs exhibit excellent binding affinities toward complementary strands and a high degree of nuclease resistance, thus making them suitable for use in antisense oligonucleotides. A 13-mer antisense strand was designed and prepared with a 5' wing and a 3' wing comprising, respectively, two and three nucleotides analogs (amideBNA, AmNA), and an 8 base central region comprising DNA, wherein all the links were phosphorothioated. A complementary strand with 5' and 3' wings comprising 2'-OMe, phosphorothioated RNA and a central region comprising natural RNA was prepared.

```
Antisense amideBNA(AmNA)/DNA gapmer strand
ASO 13-mer:
                                (SEQ ID NO: 28)
   5'-GCattggtatTCA-3'
(Upper case: N-methyl amideBNA(AmNA), lower case:
DNA, phosphorothioate bonds between nucleic acids
at all sites)

Complementary strand
1. 13-mer Toc-cRNA(G):
                                (SEQ ID NO: 7)
   5'-u_sg_sa_sAUACCAAU_sg_sc-3'
(Upper case: RNA, lower case: 2'-OMe-RNA,
s: phosphorothioate bonds between nucleic acids)
```

The antisense amidoBNA/DNA gapmer (ASO) and the complementary strand were mixed in equal molar amounts and annealed as described above in Example 7. Next, the single-stranded ASO and the annealed double-stranded nucleic acid complex were intravenously injected through the tail vein of a mouse in various amounts (ss-ASO: 0.75 mg/kg; 2.25 mg/kg; Toc-ASO/cRNA(G): 0.33 mg/kg; 1.0 mg/kg). A control mouse was also prepared by injecting PBS solution through the tail vein. Seven days or fourteen days after the injection, the mice were perfused with PBS, the livers extracted, and subsequently mRNA extraction, cDNA synthesis, and quantitative RT-PCR was carried out as described in Comparative Example 1. The relative mApoB expression level compared to mGAPDH (internal standard gene) was calculated, and the results are presented in FIG. 32.

Figure 32:
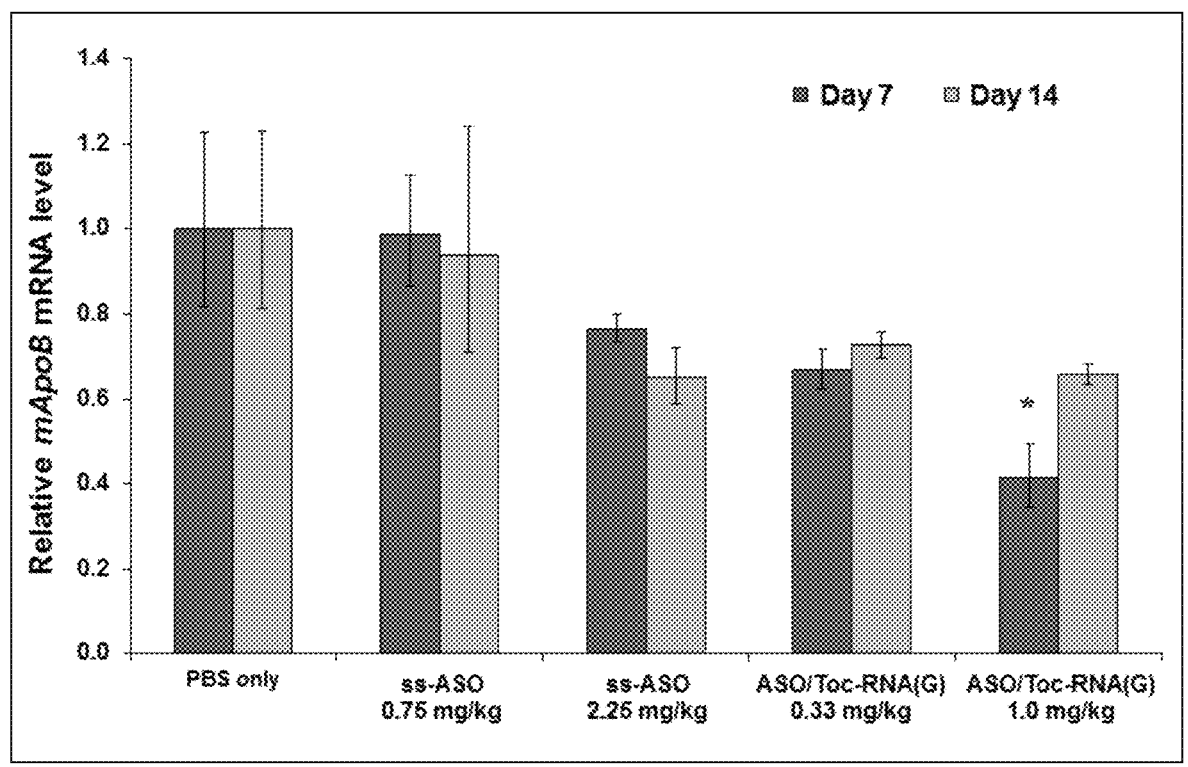
FIG. 32 is a graph illustrating the results obtained in Example 15 demonstrating suppression of expression using a double-stranded nucleic acid complex containing an ASO that includes amideBNA (AmNA) nucleotide analog.

As shown by FIG. 32, the double-stranded nucleic acid complex that incorporates amideBNA (AmNA) into the 5' wing and 3' wing regions of the first nucleic acid (antisense oligonucleotide) generates an antisense effect in vivo. The graphs shows that even when the double-stranded complex is injected into mice in lower amounts than the single-stranded ASO a greater degree of suppression is achieved with the double-stranded complex. For example, the ASO/Toc-cRNA(G) complex injected at 1.0 mg/kg yielded a suppression by approximately 55%, which was significantly lower than the result of just 20% suppression with ss-ASO at 2.25 mg/kg dose when measured 7 days post-injection. As demonstrated by this embodiment, a greater degree of suppression of expression is achieved with less reagent by practicing the method and using the double-stranded complex disclosed herein.

Example 16

This example used a double-stranded nucleic acid complex (Toc-dsASO) comprising the following first strand and second strand.

```
,1 First strand (ASO)
                                (SEQ ID NO: 32)
   5'-*TCagtcatgactTC-3
(Upper case: LNA, Lower case: DNA,
phosphorothioate bonds between nucleic acids
at all sites)

Second strand (Toc-cRNA)
                                (SEQ ID NO: 33)
   5'-Toc-G^A^AGUCAUGACU^G^A-3'
(Upper case: RNA, ^: Phosphorothioate bond, under
line: 2'-O-methyl RNA, Toc: alpha-tocopherol)
```

Then, three-week-old female ICR mice were used. the present inventors intravenously injected three mice with the Toc-dsASO (50 mg per g body weight) or phosphate-buffered saline(PBS) for each group. Three days after the injection, all of the mice were euthanized, and liver, heart muscle, skeletal muscle, lung, fat, adrenal grand, kidney, choroid plexus, lumbar dorsal root ganglion and cervical dorsal root ganglion were harvested for analysis. Cerebral microvacular fraction was separated from whole brain tissue by sucrose gradient method for the same analysis. Total RNA was extracted from the harvested tissues, and the present inventors assessed them by quantitative RT-PCR (qRT-PCR). the present inventors measured scavenger receptor class B, member 1(SRB1) as the target gene, and glyceraldehyd-3-phosphate dehydrogenase (Gapdh) gene as an internal control. The results thus obtained are presented in FIG. 33A.

In addition, three-week-old female ICR mice weighing 10 g were used. The present inventors intravenously injected three mice with the Toc-dsASO (50 mg, 25 mg, 12.5 mg and 6.25 mg per g body weight) or single strand antisense oligonucleotide (the ASO; 50 mg, 25 mg, 12.5 mg and 6.25 mg per g body weight) or PBS each. Three days after injection, all of the mice were euthanized, and each tissue was harvested for analysis. Total RNA was extracted from the harvested tissues, and we assessed them by qRT-PCR. The present inventors measured SRB1 as the target gene, and Gapdh gene as an internal control. The results thus obtained are presented in FIGS. 33B-33F.

Figure 33A:
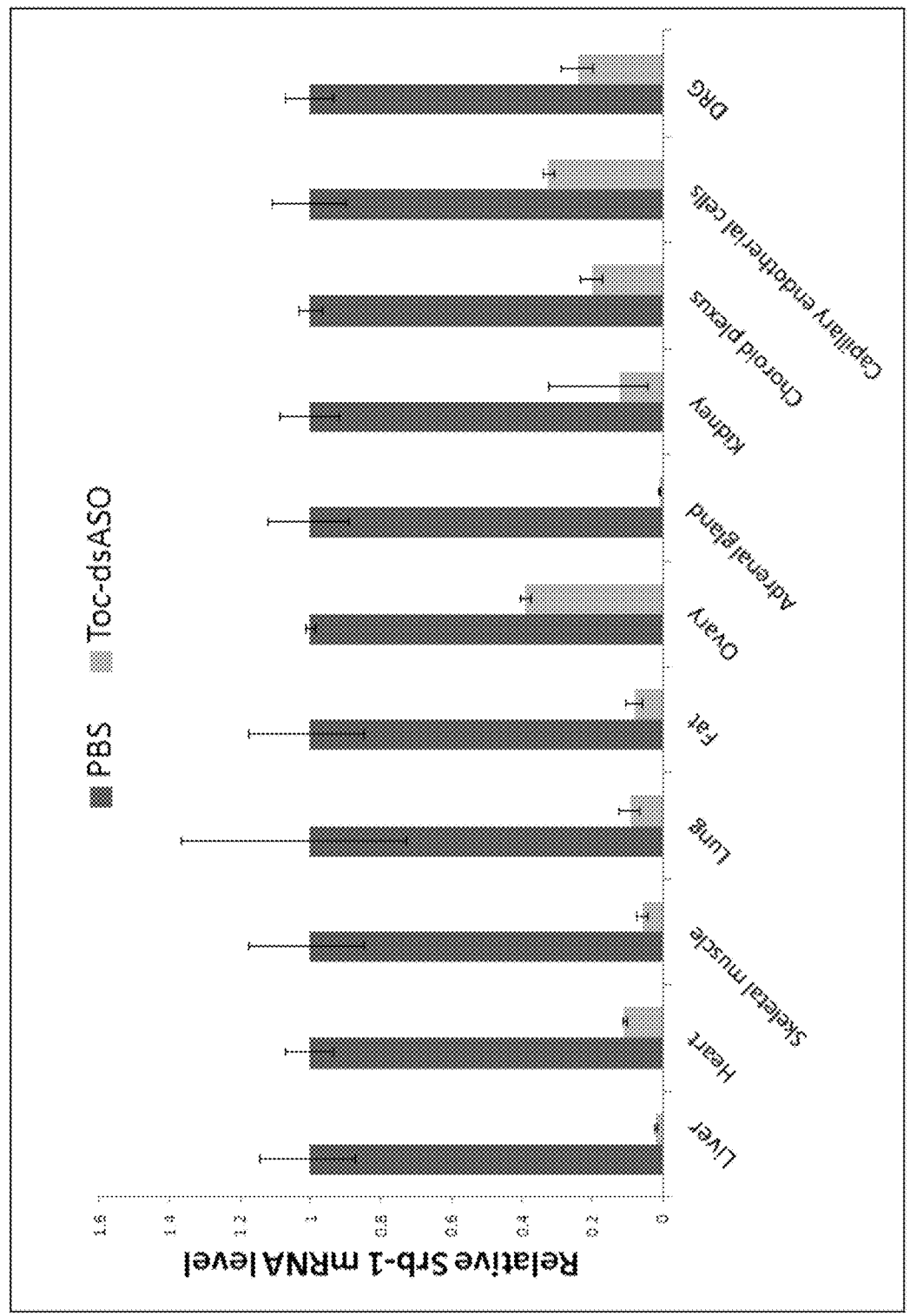
FIG. 33A is a graph showing suppression of expression caused by intravenously injecting mice with a double-stranded nucleic acid complex (a Toc-dsASO; 50 mg per g body weight) or PBS.

As is obvious from the results presented in FIG. 33A, qRT-PCR analysis showed that the expression of SRB1 in the the Toc-dsASO (50 mg per g body weight) group was reduced by 98% in the liver, by 89% in the heart muscle, by 95% in the skeletal muscle, by 91% in the lung, by 92% in the fat, by 99% in the adrenal grand, by 88% in the kidney, by 61% in the ovary, by 80% in the choroid plexus, and by 76% in the lumbar dorsal root ganglion relative to PBS control group.

Figure 33B:
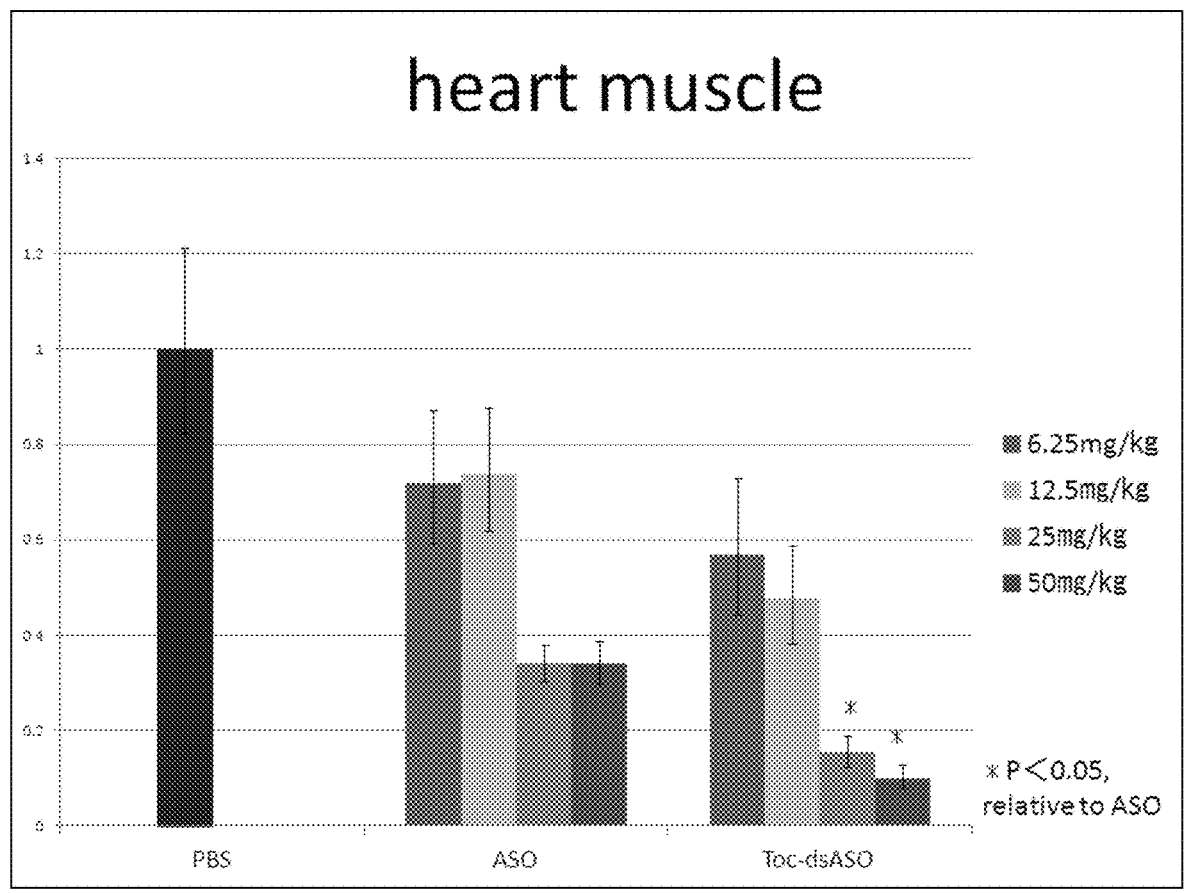
FIG. 33B is a graph showing suppression of expression in heart muscles, caused by intravenously injecting mice with the Toc-dsASO (50 mg, 25 mg, 12.5 mg and 6.25 mg per g body weight) or a single strand antisense oligonucleotide (an ASO; 50 mg, 25 mg, 12.5 mg and 6.25 mg per g body weight) or PBS.
Figure 33C:
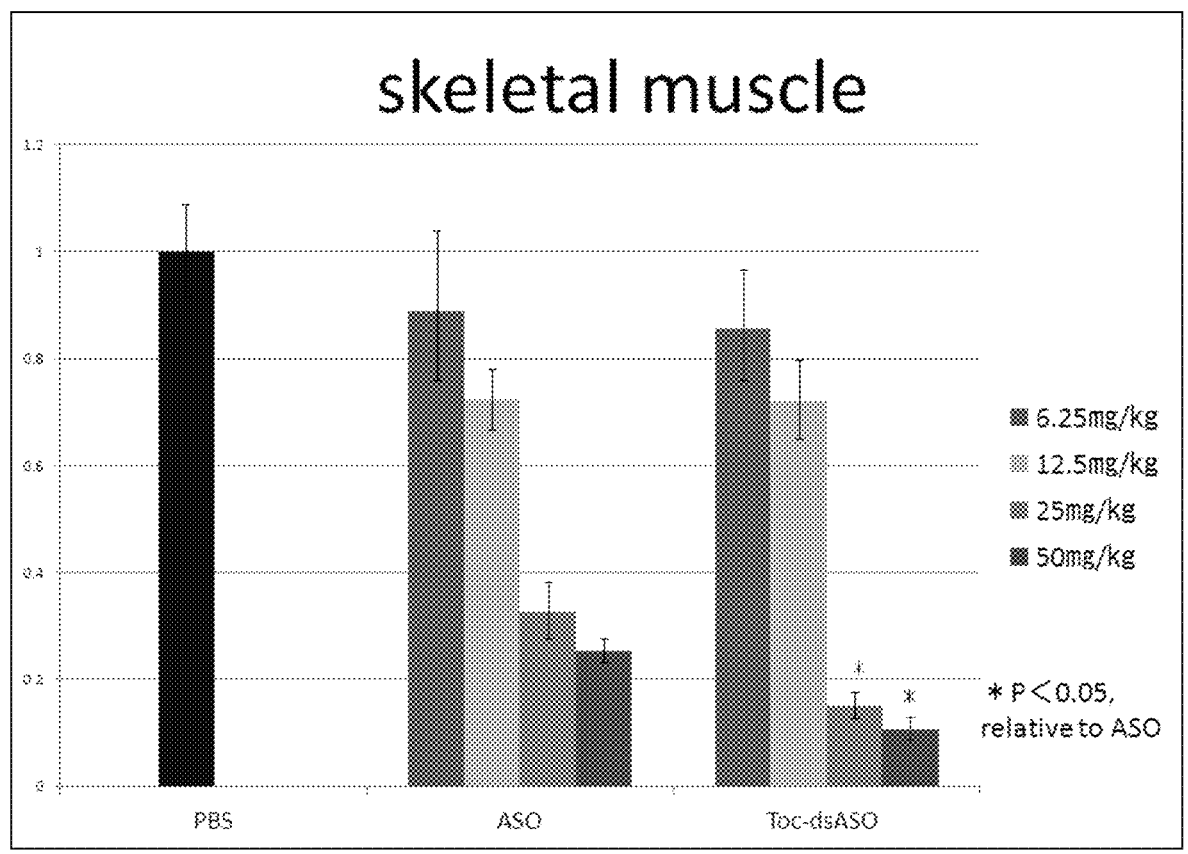
FIG. 33C is a graph showing suppression of expression in skeletal muscles, caused by intravenously injecting mice with the Toc-dsASO (50 mg, 25 mg, 12.5 mg and 6.25 mg per g body weight) or the ASO (50 mg, 25 mg, 12.5 mg and 6.25 mg per g body weight) or PBS.
Figure 33D:
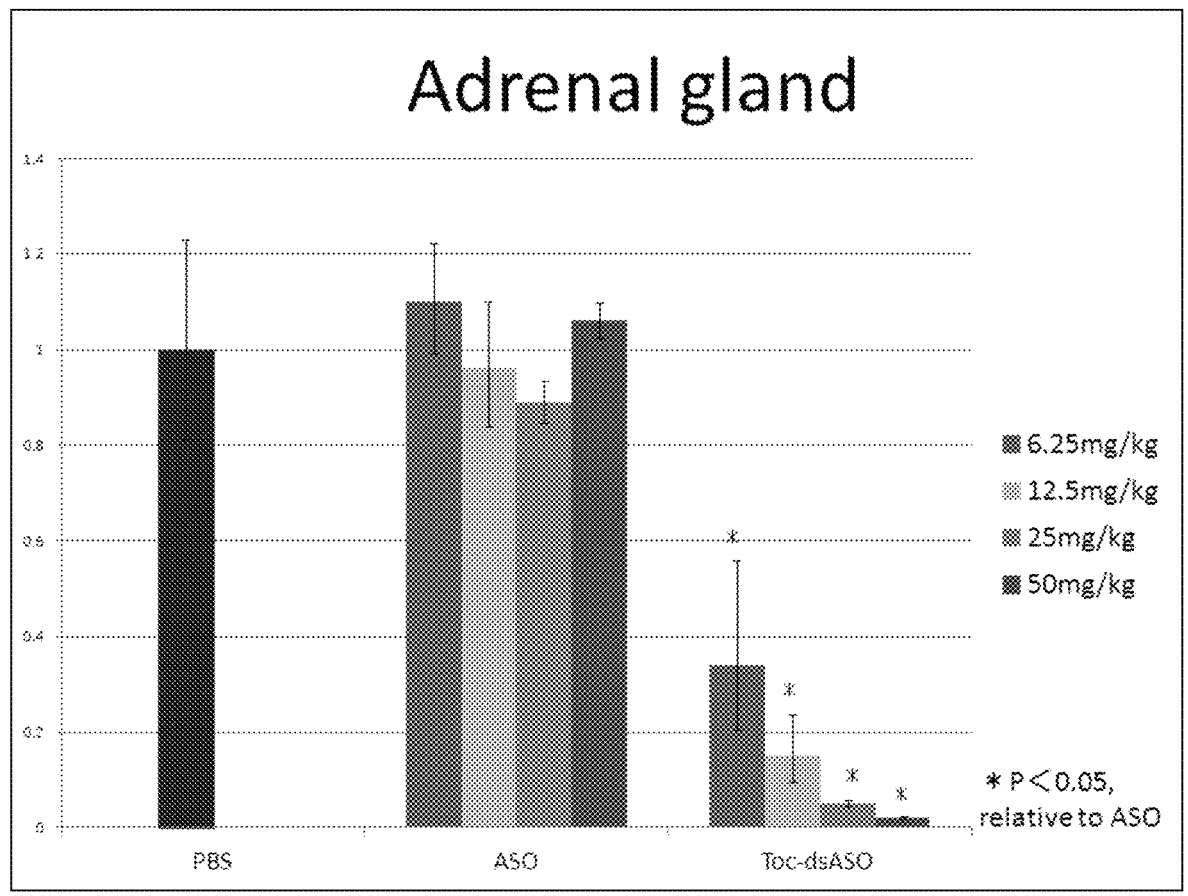
FIG. 33D is a graph showing suppression of expression in Adrenal glands, caused by intravenously injecting mice with the Toc-dsASO (50 mg, 25 mg, 12.5 mg and 6.25 mg per g body weight) or the ASO (50 mg, 25 mg, 12.5 mg and 6.25 mg per g body weight) or PBS.
Figure 33E:
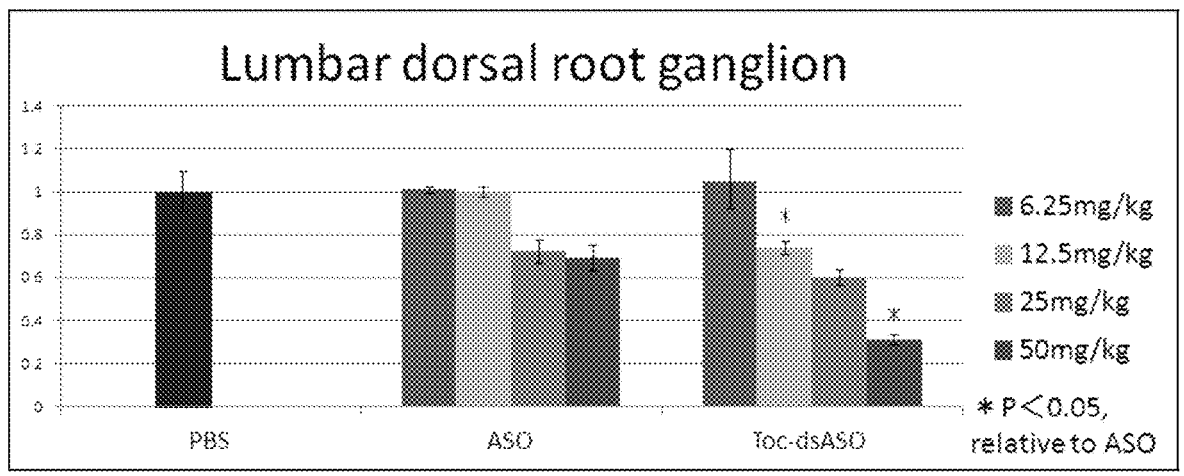
FIG. 33E is a graph showing suppression of expression in lumbar dorsal root ganglions, caused by intravenously injecting mice with the Toc-dsASO (50 mg, 25 mg, 12.5 mg and 6.25 mg per g body weight) or the ASO (50 mg, 25 mg, 12.5 mg and 6.25 mg per g body weight) or PBS.
Figure 33F:
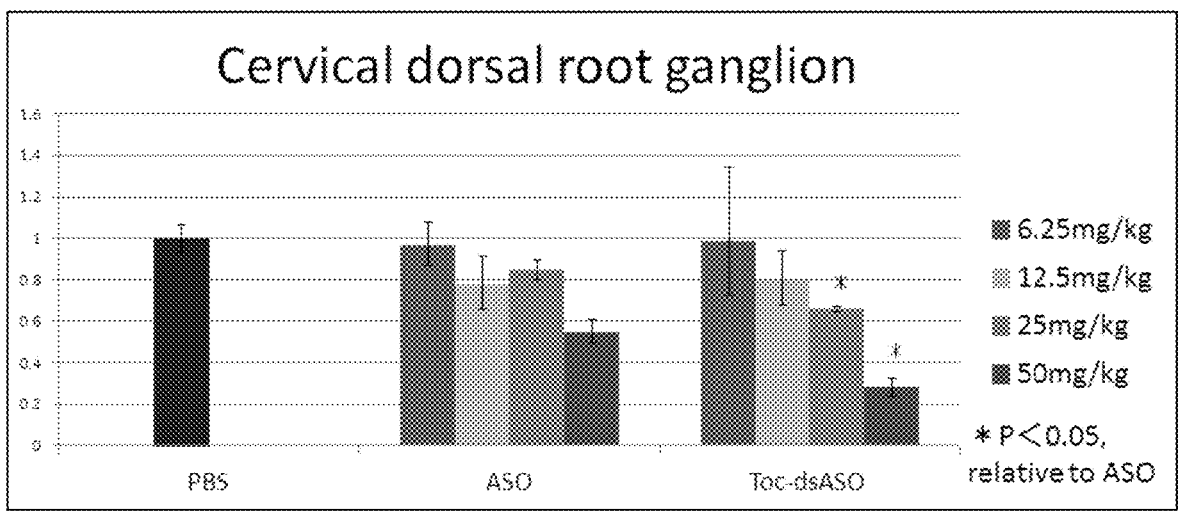
FIG. 33F is a graph showing suppression of expression in cervical dorsal root ganglions, caused by intravenously injecting mice with the Toc-dsASO (50 mg, 25 mg, 12.5 mg and 6.25 mg per g body weight) or the ASO (50 mg, 25 mg, 12.5 mg and 6.25 mg per g body weight) or PBS.

Furthermore, regarding the heart muscle, qRT-PCR analysis showed that the reduction of SRB1 in mice with the Toc-dsASO injection was more significant than that with the ASO injection in the doses of 25 and 50 mg/kg (See FIG. 33B). Regarding the skeletal muscle, qRT-PCR analysis showed that the reduction of SRB1 in mice with the Toc-dsASO injection was more significant than that with the ASO injection in the doses of 25 and 50 mg/kg (See FIG. 33C). Regarding the adrenal grand, qRT-PCR analysis showed that SRB1 expression was decreased in dose-dependent manner in mice with the Toc-dsASO injection, in contrast, there was no significant reduction of SRB1 in mice with the ASO injection (See FIG. 33D). Regarding the lumbar dorsal root ganglion, qRT-PCR analysis showed that the reduction of SRB1 in mice with the Toc-dsASO injection was more significant than that with the ASO injection in the doses of 12.5 and 50 mg/kg (See FIG. 33E). Regarding the cervical dorsal root ganglion, qRT-PCR analysis showed that the reduction of SRB1 in mice with the Toc-dsASO injection was more significant than that with the ASO injection in the doses of 25 and 50 mg/kg (See FIG. 33F).

As discussed above, using a double-stranded nucleic acid complex according to embodiments of the present invention, in some embodiments an antisense nucleic acid can be delivered to a particular organ (cells) with high specificity and high efficiency, and the expression of a target gene or the level of a transcription product can be very effectively suppressed by the antisense nucleic acid. Furthermore, since various molecules such as lipids (for example, tocopherol and cholesterol), sugars (for example, glucose and sucrose), proteins, peptides, and antibodies can be applied to the double-stranded nucleic acid of some embodiments as functional moieties for the delivery to particular organs, the double-stranded nucleic acid complex of some embodiments can be targeted to various organs, tissues and cells. Also, since the antisense effect is not reduced even if the double-stranded nucleic acid of some embodiments is subjected to modification for imparting resistance to RNase or the like, the double-stranded nucleic acid of some embodiments can also be used in embodiments of enteral administration.

Therefore, the double-stranded nucleic acid of some embodiments can provide high efficacy even when administered at a low concentration, and is also excellent from the viewpoint of reducing adverse side effects by suppressing the distribution of antisense nucleic acids in organs other than the target organ. Therefore, the double-stranded nucleic acid is useful as a pharmaceutical composition or the like for treating and preventing diseases that are associated with increased expression of target genes, such as metabolic diseases, tumors, and infections and/or increased level of a transcription product.

What is claimed is:

1. A pharmaceutical composition for reducing the level of a transcription product in a cell comprising:
   a double-stranded nucleic acid complex comprising a first nucleic acid strand, a second nucleic acid strand which has a sequence complementary to the first nucleic acid strand, wherein:
   (i) the first nucleic acid strand hybridizes to the transcription product, and is (a) a nucleic acid strand which comprises at least 4 consecutive DNA nucleotides or modified DNA nucleotides that are recognized by RNase H when the strand is hybridized to the transcription product and the total number of nucleotides is 12 to 25; and
   (ii) the second nucleic acid strand is a nucleic acid strand which comprises (a) at least 4 consecutive RNA nucleotides, and (b) one or more modified nucleotides, nucleotide analogs and/or modified nucleotide analogs located 5' to the at least 4 consecutive RNA nucleotides, and/or (c) one or more modified nucleotides, nucleotide analogs and/or modified nucleotide analogs located 3' to the at least 4 consecutive RNA nucleotides and the total number of nucleotides is 12 to 31.

2. The pharmaceutical composition according to claim 1, wherein the first nucleic acid strand is further comprises (b) a 5' wing region which comprises one or more nucleotide analogs or modified nucleotide analogs located 5' to the at least 4 consecutive DNA nucleotides or modified DNA nucleotides that are recognized by RNase H; and/or (c) a 3' wing region which comprises one or more nucleotide analogs or modified nucleotide analogs located 3' to the at least 4 consecutive DNA nucleotides or modified DNA nucleotides that are recognized by RNase H.

3. The pharmaceutical composition according to claim 1, wherein the double stranded nucleic acid complex further comprises a third nucleic acid strand annealed to the second nucleic acid strand.

4. The pharmaceutical composition according to claim 3, wherein the third nucleic acid strand (i) comprises nucleotides and optionally nucleotide analogs and total number of the nucleotides and nucleotide analogs which are optionally comprised is 8 to 100, (ii) comprises at least 4 consecutive nucleotides that are recognized by RNase H when the strand is hybridized to a second transcription product, and (iii) hybridizes to the second transcription product.

5. The pharmaceutical composition according to claim 3, wherein the third nucleic acid strand hybridizes to a transcription product that is identical to the transcription product to which the first nucleic acid strand hybridizes.

6. The pharmaceutical composition according to claim 3, wherein the third nucleic acid strand hybridizes to a transcription product different from the transcription product to which the first nucleic acid strand hybridizes.

7. The pharmaceutical composition according to claim 1, wherein the second nucleic acid strand further comprises a functional moiety having a function selected from a labeling function, a purification function, and a targeted delivery function.

8. The pharmaceutical composition according to claim 1, wherein the nucleotide analogs in the first nucleic acid strand are bridged nucleotides.

9. The pharmaceutical composition according to claim 1, wherein at least one of the nucleotides and the nucleotide analogs in the first nucleic acid strand is phosphorothioated.

10. The pharmaceutical composition according to claim 7, wherein the functional moiety is a molecule selected from the group consisting of a lipid, a glycolipid, a glyceride, a sugar, a peptide, and a protein.

11. The pharmaceutical composition according to claim 7, wherein the functional moiety is a lipid selected from the group consisting of a fatty acid, a lipid-soluble vitamin, a glycolipid, and a glyceride.

12. The pharmaceutical composition according to claim 7, wherein the functional moiety is a molecule selected from the group consisting of cholesterol, a tocopherol, a tocotrienol, glucose, sucrose, acylcarintine, acyl-CoA, and an antibody.

13. The pharmaceutical composition according to claim 1, wherein at least one of the nucleotide analogs is a molecule selected from the group consisting of a hexitol nucleic acid (HNA), a cyclohexane nucleic acid (CeNA), a peptide nucleic acid (PNA), a glycol nucleic acid (GNA), a threose nucleic acid (TNA), a morpholino nucleic acid, a tricyclo-DNA (tcDNA), a 2'-O-methylated nucleic acid, a 2'-MOE (2'-O-methoxyethyl) lated nucleic acid, a 2'-AP (2'-O-aminopropyl) lated nucleic acid, a 2'-fluorinated nucleic acid, a 2'-F-arabinonucleic acid (2'-FANA), and a bridged nucleic acid (BNA).

14. The pharmaceutical composition according to claim 8, wherein the BNA is a molecule selected from the group consisting of α-L-methyleneoxy (4'-CH$_{2\text{-}O\text{-}2'}$) BNA, β-D-methyleneoxy (4'-CH$_{2\text{-}O\text{-}2'}$) BNA, ethyleneoxy (4'-CH$_{2\text{-}2\text{-}O\text{-}2'}$) BNA, β-D-thio (4'-CH$_{2\text{-}S\text{-}2'}$) BNA, aminooxy (4'-CH$_{2\text{-}O\text{-}N(R3)}$-2') BNA, oxyamino (4'-CH$_{2'N(R3)}$--O-2') BNA, 2', 4'-BNA-COC, 3'-amino-2', 4'-BNA, 5'-methyl BNA, 4'-CH(CH$_3$)--O-2'-BNA, 4'-CH(CH$_{2OCH3}$)--O-2'-BNA, amide (4'-C(O)--N(H)-2') BNA, and amide (4'-C(O)--N(Me)-2') BNA.

* * * * *

SEQUENCE LISTING

```
<160> NUMBER OF SEQ ID NOS: 33

<210> SEQ ID NO 1
<211> LENGTH: 12
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(12)
<223> OTHER INFORMATION: Phosphorothioate bonds between nucleic acids
<220> FEATURE:
<221> NAME/KEY: modified_base
<222> LOCATION: (11)..(12)
<223> OTHER INFORMATION: LNA

<400> SEQUENCE: 1
gcattggtat tc                                                         12

<210> SEQ ID NO 2
<211> LENGTH: 12
<212> TYPE: RNA
<213> ORGANISM: Artificial Sequence
<220> FEATURE:
<223> OTHER INFORMATION: Artificially synthesized oligonucleotide
      sequence

<400> SEQUENCE: 2
gaauaccaau gc                                                         12

<210> SEQ ID NO 3
<211> LENGTH: 12
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: OMe-RNA
<220> FEATURE:
<221> NAME/KEY: modified_base
<222> LOCATION: (1)..(3)
<223> OTHER INFORMATION: Phosphorothioate bonds between nucleic acids
<220> FEATURE:
<221> NAME/KEY: modified_base
<222> LOCATION: (10)..(12)
<223> OTHER INFORMATION: Phosphorothioate bonds between nucleic acids
<220> FEATURE:
<221> NAME/KEY: modified_base
<222> LOCATION: (11)..(12)
<223> OTHER INFORMATION: OMe-RNA
```

-continued

<400> SEQUENCE: 3
gaauaccaau gc                                                          12

<210> SEQ ID NO 4
<211> LENGTH: 12
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(12)
<223> OTHER INFORMATION: OMe-RNA
<220> FEATURE:
<221> NAME/KEY: modified_base
<222> LOCATION: (1)..(12)
<223> OTHER INFORMATION: Phosphorothioate bonds between nucleic acids

<400> SEQUENCE: 4
gaauaccaau gc                                                          12

<210> SEQ ID NO 5
<211> LENGTH: 13
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: Phosphorothioate bonds between nucleic acids
<220> FEATURE:
<221> NAME/KEY: modified_base
<222> LOCATION: (11)..(13)
<223> OTHER INFORMATION: LNA

<400> SEQUENCE: 5
gcattggtat tca                                                         13

<210> SEQ ID NO 6
<211> LENGTH: 14
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: LNA
<220> FEATURE:
<221> NAME/KEY: modified_base
<222> LOCATION: (1)..(14)
<223> OTHER INFORMATION: Phosphorothioate bonds between nucleic acids
<220> FEATURE:
<221> NAME/KEY: modified_base
<222> LOCATION: (12)..(14)
<223> OTHER INFORMATION: LNA

<400> SEQUENCE: 6
agcattggta ttca                                                        14

<210> SEQ ID NO 7
<211> LENGTH: 13

```
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: OMe-RNA
<220> FEATURE:
<221> NAME/KEY: modified_base
<222> LOCATION: (1)..(4)
<223> OTHER INFORMATION: Phosphorothioate bonds between nucleic acids
<220> FEATURE:
<221> NAME/KEY: modified_base
<222> LOCATION: (11)..(13)
<223> OTHER INFORMATION: Phosphorothioate bonds between nucleic acids
<220> FEATURE:
<221> NAME/KEY: modified_base
<222> LOCATION: (12)..(13)
<223> OTHER INFORMATION: OMe-RNA

<400> SEQUENCE: 7
ugaauaccaa ugc                                                        13

<210> SEQ ID NO 8
<211> LENGTH: 14
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: OMe-RNA
<220> FEATURE:
<221> NAME/KEY: modified_base
<222> LOCATION: (1)..(4)
<223> OTHER INFORMATION: Phosphorothioate bonds between nucleic acids
<220> FEATURE:
<221> NAME/KEY: modified_base
<222> LOCATION: (11)..(14)
<223> OTHER INFORMATION: Phosphorothioate bonds between nucleic acids
<220> FEATURE:
<221> NAME/KEY: modified_base
<222> LOCATION: (12)..(14)
<223> OTHER INFORMATION: OMe-RNA

<400> SEQUENCE: 8
ugaauaccaa ugcu                                                       14

<210> SEQ ID NO 9
<211> LENGTH: 12
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(12)
<223> OTHER INFORMATION: OMe-RNA
<220> FEATURE:
<221> NAME/KEY: modified_base
<222> LOCATION: (1)..(3)
<223> OTHER INFORMATION: Phosphorothioate bonds between nucleic acids
<220> FEATURE:
<221> NAME/KEY: modified_base
<222> LOCATION: (10)..(12)
<223> OTHER INFORMATION: Phosphorothioate bonds between nucleic acids

<400> SEQUENCE: 9
gaauaccaau gc                                                         12
```

```
<210> SEQ ID NO 10
<211> LENGTH: 21
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: OMe-RNA
<220> FEATURE:
<221> NAME/KEY: modified_base
<222> LOCATION: (1)..(3)
<223> OTHER INFORMATION: Phosphorothioate bonds between nucleic acids
<220> FEATURE:
<221> NAME/KEY: modified_base
<222> LOCATION: (19)..(21)
<223> OTHER INFORMATION: OMe-RNA
<220> FEATURE:
<221> NAME/KEY: modified_base
<222> LOCATION: (19)..(21)
<223> OTHER INFORMATION: Phosphorothioate bonds between nucleic acids

<400> SEQUENCE: 10
uucgcaccag aauaccaaug c                                              21

<210> SEQ ID NO 11
<211> LENGTH: 9
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(9)
<223> OTHER INFORMATION: PNA

<400> SEQUENCE: 11 tggtgcgaa                                                             9

<210> SEQ ID NO 12
<211> LENGTH: 12
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(12)
<223> OTHER INFORMATION: PNA

<400> SEQUENCE: 12
gaauaccaau gc                                                        12

<210> SEQ ID NO 13
<211> LENGTH: 10
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(10)
<223> OTHER INFORMATION: PNA

<400> SEQUENCE: 13
```
gaauaccaau                                                                  10

<210> SEQ ID NO 14
<211> LENGTH: 8
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(8)
<223> OTHER INFORMATION: PNA

<400> SEQUENCE: 14 gaauacca                                                                    8

<210> SEQ ID NO 15
<211> LENGTH: 13
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: LNA
<220> FEATURE:
<221> NAME/KEY: modified_base
<222> LOCATION: (1)..(4)
<223> OTHER INFORMATION: Phosphorothioate bonds between nucleic acids
<220> FEATURE:
<221> NAME/KEY: modified_base
<222> LOCATION: (11)..(13)
<223> OTHER INFORMATION: Phosphorothioate bonds between nucleic acids
<220> FEATURE:
<221> NAME/KEY: modified_base
<222> LOCATION: (12)..(13)
<223> OTHER INFORMATION: LNA

<400> SEQUENCE: 15
ugaauaccaa ugc                                                              13

<210> SEQ ID NO 16
<211> LENGTH: 13
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: LNA
<220> FEATURE:
<221> NAME/KEY: modified_base
<222> LOCATION: (1)..(13)
<223> OTHER INFORMATION: Phosphorothioate bonds between nucleic acids
<220> FEATURE:
<221> NAME/KEY: modified_base
<222> LOCATION: (12)..(13)
<223> OTHER INFORMATION: LNA

<400> SEQUENCE: 16
ugaauaccaa ugc                                                              13

<210> SEQ ID NO 17
<211> LENGTH: 13
<212> TYPE: RNA
<213> ORGANISM: Artificial Sequence
<220> FEATURE:

```
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: OMe-RNA
<220> FEATURE:
<221> NAME/KEY: modified_base
<222> LOCATION: (1)..(13)
<223> OTHER INFORMATION: Phosphorothioate bonds between nucleic acids
<220> FEATURE:
<221> NAME/KEY: modified_base
<222> LOCATION: (12)..(13)
<223> OTHER INFORMATION: OMe-RNA

<400> SEQUENCE: 17
ugaauaccaa ugc                                                         13

<210> SEQ ID NO 18
<211> LENGTH: 31
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: OMe-RNA
<220> FEATURE:
<221> NAME/KEY: modified_base
<222> LOCATION: (1)..(4)
<223> OTHER INFORMATION: Phosphorothioate bonds between nucleic acids
<220> FEATURE:
<221> NAME/KEY: modified_base
<222> LOCATION: (12)..(31)
<223> OTHER INFORMATION: OMe-RNA
<220> FEATURE:
<221> NAME/KEY: modified_base
<222> LOCATION: (28)..(31)
<223> OTHER INFORMATION: Phosphorothioate bonds between nucleic acids

<400> SEQUENCE: 18
ugaauaccaa ugcuacgcau acgcaccacc a                                     31

<210> SEQ ID NO 19
<211> LENGTH: 13
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: Phosphorothioate bonds between nucleic acids
<220> FEATURE:
<221> NAME/KEY: modified_base
<222> LOCATION: (11)..(13)
<223> OTHER INFORMATION: LNA

<400> SEQUENCE: 19
tgtctctgcc tgg                                                         13

<210> SEQ ID NO 20
<211> LENGTH: 13
<212> TYPE: RNA
<213> ORGANISM: Artificial Sequence
<220> FEATURE:
```

```
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: OMe-RNA
<220> FEATURE:
<221> NAME/KEY: modified_base
<222> LOCATION: (1)..(4)
<223> OTHER INFORMATION: Phosphorothioate bonds between nucleic acids
<220> FEATURE:
<221> NAME/KEY: modified_base
<222> LOCATION: (11)..(13)
<223> OTHER INFORMATION: Phosphorothioate bonds between nucleic acids
<220> FEATURE:
<221> NAME/KEY: modified_base
<222> LOCATION: (12)..(13)
<223> OTHER INFORMATION: OMe-RNA

<400> SEQUENCE: 20
ccaggcagag aca                                                         13

<210> SEQ ID NO 21
<211> LENGTH: 20
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(5)
<223> OTHER INFORMATION: LNA
<220> FEATURE:
<221> NAME/KEY: modified_base
<222> LOCATION: (1)..(20)
<223> OTHER INFORMATION: Phosphorothioate bonds between nucleic acids
<220> FEATURE:
<221> NAME/KEY: modified_base
<222> LOCATION: (16)..(20)
<223> OTHER INFORMATION: LNA

<400> SEQUENCE: 21
ttattgtctc tgcctggact                                                  20

<210> SEQ ID NO 22
<211> LENGTH: 20
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(5)
<223> OTHER INFORMATION: OMe-RNA
<220> FEATURE:
<221> NAME/KEY: modified_base
<222> LOCATION: (1)..(6)
<223> OTHER INFORMATION: Phosphorothioate bonds between nucleic acids
<220> FEATURE:
<221> NAME/KEY: modified_base
<222> LOCATION: (15)..(20)
<223> OTHER INFORMATION: Phosphorothioate bonds between nucleic acids
<220> FEATURE:
<221> NAME/KEY: modified_base
<222> LOCATION: (16)..(20)
<223> OTHER INFORMATION: OMe-RNA

<400> SEQUENCE: 22
aguccaggca gagacaauaa                                                  20

<210> SEQ ID NO 23
```

<211> LENGTH: 13
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: Phosphorothioate bonds between nucleic acids
<220> FEATURE:
<221> NAME/KEY: modified_base
<222> LOCATION: (11)..(13)
<223> OTHER INFORMATION: LNA

<400> SEQUENCE: 23
tagtccagtt cac                                                     13

<210> SEQ ID NO 24
<211> LENGTH: 22
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: OMe-RNA
<220> FEATURE:
<221> NAME/KEY: modified_base
<222> LOCATION: (1)..(4)
<223> OTHER INFORMATION: Phosphorothioate bonds between nucleic acids
<220> FEATURE:
<221> NAME/KEY: modified_base
<222> LOCATION: (12)..(22)
<223> OTHER INFORMATION: OMe-RNA
<220> FEATURE:
<221> NAME/KEY: modified_base
<222> LOCATION: (20)..(22)
<223> OTHER INFORMATION: Phosphorothioate bonds between nucleic acids

<400> SEQUENCE: 24
gugaacugga cuauacgcac ca                                           22

<210> SEQ ID NO 25
<211> LENGTH: 12
<212> TYPE: PRT
<213> ORGANISM: Artificial Sequence
<220> FEATURE:
<223> OTHER INFORMATION: Artificially synthesized polypeptide sequence

<400> SEQUENCE: 25

Ser Pro Gly Ala Arg Ala Phe Gly Gly Gly Gly Ser
1               5                   10

<210> SEQ ID NO 26
<211> LENGTH: 15
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: LNA
<220> FEATURE:
<221> NAME/KEY: modified_base

```
<222> LOCATION: (1)..(15)
<223> OTHER INFORMATION: Phosphorothioate bonds between nucleic acids
<220> FEATURE:
<221> NAME/KEY: modified_base
<222> LOCATION: (13)..(15)
<223> OTHER INFORMATION: LNA

<400> SEQUENCE: 26
ccattgtcac actcc                                                    15

<210> SEQ ID NO 27
<211> LENGTH: 15
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: OMe-RNA
<220> FEATURE:
<221> NAME/KEY: modified_base
<222> LOCATION: (1)..(4)
<223> OTHER INFORMATION: Phosphorothioate bonds between nucleic acids
<220> FEATURE:
<221> NAME/KEY: modified_base
<222> LOCATION: (12)..(15)
<223> OTHER INFORMATION: Phosphorothioate bonds between nucleic acids
<220> FEATURE:
<221> NAME/KEY: modified_base
<222> LOCATION: (13)..(15)
<223> OTHER INFORMATION: OMe-RNA

<400> SEQUENCE: 27
ggagugugac caugg                                                    15

<210> SEQ ID NO 28
<211> LENGTH: 13
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: N-methyl amideBNA
<220> FEATURE:
<221> NAME/KEY: modified_base
<222> LOCATION: (1)..(13)
<223> OTHER INFORMATION: Phosphorothioate bonds between nucleic acids
<220> FEATURE:
<221> NAME/KEY: modified_base
<222> LOCATION: (11)..(13)
<223> OTHER INFORMATION: N-methyl amideBNA

<400> SEQUENCE: 28
gcattggtat tca                                                      13

<210> SEQ ID NO 29
<211> LENGTH: 20
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(5)
<223> OTHER INFORMATION: LNA
<220> FEATURE:
<221> NAME/KEY: modified_base
```

```
<222> LOCATION: (1)..(20)
<223> OTHER INFORMATION: Phosphorothioate bonds between nucleic acids
<220> FEATURE:
<221> NAME/KEY: modified_base
<222> LOCATION: (16)..(20)
<223> OTHER INFORMATION: LNA

<400> SEQUENCE: 29
tccagcattg gtattcagtg                                                    20

<210> SEQ ID NO 30
<211> LENGTH: 29
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(5)
<223> OTHER INFORMATION: LNA
<220> FEATURE:
<221> NAME/KEY: modified_base
<222> LOCATION: (1)..(29)
<223> OTHER INFORMATION: Phosphorothioate bonds between nucleic acids
<220> FEATURE:
<221> NAME/KEY: modified_base
<222> LOCATION: (25)..(29)
<223> OTHER INFORMATION: LNA

<400> SEQUENCE: 30
tccagcattg gtattcagtg tgatgacac                                          29

<210> SEQ ID NO 31
<211> LENGTH: 9
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(9)
<223> OTHER INFORMATION: PNA

<400> SEQUENCE: 31 tggtgcgta                                                                 9

<210> SEQ ID NO 32
<211> LENGTH: 14
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(14)
<223> OTHER INFORMATION: Phosphorothioate bonds between nucleic acids
<220> FEATURE:
<221> NAME/KEY: modified_base
<222> LOCATION: (13)..(14)
<223> OTHER INFORMATION: LNA

<400> SEQUENCE: 32
tcagtcatga cttc                                                          14
```

```
<210> SEQ ID NO 33
<211> LENGTH: 14
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: OMe-RNA
<220> FEATURE:
<221> NAME/KEY: modified_base
<222> LOCATION: (1)..(3)
<223> OTHER INFORMATION: Phosphorothioate bonds between nucleic acids
<220> FEATURE:
<221> NAME/KEY: modified_base
<222> LOCATION: (12)..(14)
<223> OTHER INFORMATION: Phosphorothioate bonds between nucleic acids
<220> FEATURE:
<221> NAME/KEY: modified_base
<222> LOCATION: (13)..(14)
<223> OTHER INFORMATION: OMe-RNA

<400> SEQUENCE: 33
gaagucauga cuga                                                         14
```